(12) United States Patent
Holtz et al.

(10) Patent No.: US 10,842,555 B2
(45) Date of Patent: Nov. 24, 2020

(54) CATHETER FOR TREATING TISSUE WITH NON-THERMAL ABLATION

(75) Inventors: Michael C. Holtz, Elk River, MN (US); Stephen K. Sundquist, Minnetonka, MN (US); Benjamin R. Fruland, Plymouth, MN (US); Tom A. Nelson, Elk River, MN (US); Kai Kroll, Plymouth, MN (US)

(73) Assignee: Prostacare Pty Ltd, Sydney (AU)

(*) Notice: Subject to any disclaimer, the term of this patent is extended or adjusted under 35 U.S.C. 154(b) by 419 days.

(21) Appl. No.: 12/544,127

(22) Filed: Aug. 19, 2009

(65) Prior Publication Data
US 2010/0049192 A1 Feb. 25, 2010

Related U.S. Application Data

(60) Provisional application No. 61/090,600, filed on Aug. 20, 2008, provisional application No. 61/090,519, (Continued)

(51) Int. Cl.
*A61B 18/14* (2006.01)
*A61B 34/00* (2016.01)
(Continued)

(52) U.S. Cl.
CPC ...... *A61B 18/1492* (2013.01); *A61B 18/1206* (2013.01); *A61B 18/16* (2013.01);
(Continued)

(58) Field of Classification Search
CPC ............... A61B 18/1492; A61B 18/08; A61B 2218/002; A61B 2018/1475;
(Continued)

(56) References Cited

U.S. PATENT DOCUMENTS 3,698,394 A   10/1972   Piper et al.
3,933,616 A   1/1976   Beer
(Continued)

FOREIGN PATENT DOCUMENTS

EP   1080731 A2   3/2001
EP   2 326 273   6/2011
(Continued)

OTHER PUBLICATIONS

PCT International Search Report, dated Oct. 22, 2009.
(Continued)

*Primary Examiner* — Thomas A Giuliani
(74) *Attorney, Agent, or Firm* — Patterson Thuente Pedersen, P.A.

(57) ABSTRACT

Systems and methods for non-thermal ablation of tissue are provided. A non-implantable minimally invasive system for treatment of tissue in a body via direct current ablation is provided. A catheter for use in such system is further provided. The catheter includes a tubular body having a proximal end, a distal end, and a tip positioned at the distal end. The tubular body is semi-flexible, bi-directionally torqueable, and chemically resistant. The tubular body includes a plurality of routing holes provided between the proximal end and the distal end for facilitating deployment of electrodes from the tubular body. The tubular body further comprises an inner sheath generally at an interior portion and an outer sheath generally at an exterior portion and being chemically resistant.

38 Claims, 78 Drawing Sheets

Related U.S. Application Data filed on Aug. 20, 2008, provisional application No. 61/090,594, filed on Aug. 20, 2008, provisional application No. 61/090,589, filed on Aug. 20, 2008.

(51) Int. Cl.

| | | |
|---|---|---|
| *A61B 18/12* | (2006.01) | |
| *A61B 18/16* | (2006.01) | |
| *A61B 18/18* | (2006.01) | |
| *A61N 1/36* | (2006.01) | |
| *A61B 5/055* | (2006.01) | |
| *A61B 8/08* | (2006.01) | |
| *A61B 18/00* | (2006.01) | |
| *A61B 90/00* | (2016.01) | |

(52) U.S. Cl.
CPC .......... *A61B 18/1815* (2013.01); *A61B 34/25* (2016.02); *A61N 1/36071* (2013.01); *A61B 5/055* (2013.01); *A61B 8/08* (2013.01); *A61B 2018/0022* (2013.01); *A61B 2018/00083* (2013.01); *A61B 2018/00148* (2013.01); *A61B 2018/00285* (2013.01); *A61B 2018/00547* (2013.01); *A61B 2018/00577* (2013.01); *A61B 2018/00702* (2013.01); *A61B 2018/00755* (2013.01); *A61B 2018/00767* (2013.01); *A61B 2018/00791* (2013.01); *A61B 2018/00875* (2013.01); *A61B 2018/00982* (2013.01); *A61B 2018/00988* (2013.01); *A61B 2018/1266* (2013.01); *A61B 2018/143* (2013.01); *A61B 2018/1467* (2013.01); *A61B 2018/1475* (2013.01); *A61B 2018/1861* (2013.01); *A61B 2090/378* (2016.02); *A61B 2218/002* (2013.01)

(58) Field of Classification Search
CPC .... A61B 2018/1472; A61B 2018/1425; A61B 2018/1427; A61B 2018/143; A61B 2018/00285; A61B 2018/1467; A61B 2018/00029; A61B 2018/00035; A61B 2018/1266; A61B 2018/00547; A61B 2018/00273; A61B 2018/00279; A61B 2018/00291
USPC ......... 606/27–29, 32; 607/98–100, 115, 143; 604/113
See application file for complete search history.

(56) References Cited

U.S. PATENT DOCUMENTS

| | | |
|---|---|---|
| 4,003,379 A | 1/1977 | Ellinwood, Jr. |
| 4,026,304 A | 5/1977 | Levy |
| 4,289,135 A | 9/1981 | Nordenstrom et al. |
| 4,572,214 A | 2/1986 | Nordenstrom et al. |
| 4,639,244 A | 1/1987 | Rizk et al. |
| 4,679,561 A | 7/1987 | Doss |
| 4,682,596 A | 7/1987 | Bales et al. |
| 4,721,123 A | 1/1988 | Cosentino et al. |
| 4,919,138 A | 4/1990 | Nordenstrom |
| 4,974,595 A | 12/1990 | Nordenstrom |
| 5,002,558 A | 3/1991 | Klein et al. |
| 5,026,371 A | 6/1991 | Rydell et al. |
| 5,058,605 A | 10/1991 | Slovak |
| 5,084,154 A | 1/1992 | Wakizoe et al. |
| 5,098,843 A | 3/1992 | Calvin |
| 5,281,218 A | 1/1994 | Imran |
| 5,304,214 A | 4/1994 | DeFord et al. |
| 5,314,451 A | 5/1994 | Mulier |
| 5,314,457 A | 5/1994 | Jeutter et al. |
| 5,370,675 A | 12/1994 | Edwards et al. |
| 5,431,625 A | 7/1995 | Fabian et al. |
| 5,458,627 A | 10/1995 | Baranowski |
| 5,482,054 A | 1/1996 | Slater et al. |
| 5,501,662 A | 3/1996 | Hofmann |
| 5,507,724 A | 4/1996 | Hofmann et al. |
| 5,529,574 A | 6/1996 | Frackelton |
| 5,536,240 A | 7/1996 | Edwards et al. |
| 5,536,267 A | 7/1996 | Edwards et al. |
| 5,558,673 A | 9/1996 | Edwards et al. |
| 5,584,872 A | 12/1996 | LaFontaine et al. |
| 5,611,350 A | 3/1997 | John |
| 5,630,426 A | 5/1997 | Eggers et al. |
| 5,672,153 A | 9/1997 | Lax et al. |
| 5,674,267 A | 10/1997 | Mir et al. |
| 5,680,860 A | 10/1997 | Imran |
| 5,701,895 A | 12/1997 | Prutchi et al. |
| 5,718,686 A | 2/1998 | Davis |
| 5,807,306 A | 9/1998 | Shapland et al. |
| 5,810,764 A | 9/1998 | Eggers et al. |
| 5,820,548 A | 10/1998 | Sieben et al. |
| 5,868,741 A | 2/1999 | Chia et al. |
| 5,869,326 A | 2/1999 | Hofmann |
| 5,919,187 A | 7/1999 | Guglielmi et al. |
| 5,931,858 A | 8/1999 | Mackey |
| 5,983,131 A | 11/1999 | Weaver et al. |
| 5,985,305 A | 11/1999 | Peery et al. |
| 5,993,434 A | 11/1999 | Dev et al. |
| 6,009,345 A | 12/1999 | Hofmann |
| 6,016,452 A | 1/2000 | Kasevich |
| 6,021,347 A | 2/2000 | Herbst et al. |
| 6,023,638 A | 2/2000 | Swanson |
| 6,049,733 A | 4/2000 | Phipps et al. |
| 6,051,017 A | 4/2000 | Loeb et al. |
| 6,162,219 A | 12/2000 | Nilsson et al. |
| 6,165,206 A | 12/2000 | Tu |
| 6,169,924 B1 | 1/2001 | Meloy et al. |
| 6,171,787 B1 | 1/2001 | Wiley |
| 6,174,309 B1 | 1/2001 | Wrublewski et al. |
| 6,179,833 B1 | 1/2001 | Taylor |
| 6,238,393 B1 | 5/2001 | Mulier et al. |
| 6,245,068 B1 | 6/2001 | Olson et al. |
| 6,269,270 B1 | 7/2001 | Boveja |
| 6,273,886 B1 | 8/2001 | Edwards |
| 6,278,895 B1 | 8/2001 | Bernard |
| 6,366,808 B1 | 4/2002 | Schroeppel et al. |
| 6,379,353 B1 * | 4/2002 | Nichols .............. A61B 18/1477 606/41 |
| 6,387,075 B1 * | 5/2002 | Stivland et al. .......... 604/96.01 |
| 6,391,026 B1 | 5/2002 | Hung et al. |
| 6,402,745 B1 | 6/2002 | Wilk |
| 6,419,673 B1 | 7/2002 | Edwards et al. |
| 6,464,699 B1 | 10/2002 | Swanson |
| 6,591,133 B1 | 7/2003 | Joshi |
| 6,595,989 B1 | 7/2003 | Schaer |
| 6,599,274 B1 | 7/2003 | Kucharczyk et al. |
| 6,600,953 B2 | 7/2003 | Flesler et al. |
| 6,607,528 B1 | 8/2003 | Quick et al. |
| 6,626,899 B2 | 9/2003 | Houser et al. |
| 6,638,273 B1 | 10/2003 | Farley et al. |
| 6,638,275 B1 | 10/2003 | McGaffigan et al. |
| 6,708,066 B2 | 3/2004 | Herbst et al. |
| 6,713,291 B2 | 3/2004 | King et al. |
| 6,733,485 B1 | 5/2004 | Whitehurst et al. |
| 6,738,663 B2 | 5/2004 | Schroeppel et al. |
| 6,901,296 B1 | 5/2005 | Whitehurst et al. |
| 6,952,615 B2 * | 10/2005 | Satake .......................... 607/102 |
| 7,079,890 B2 | 7/2006 | Ahn et al. |
| 7,412,285 B2 | 8/2008 | Schroeppel et al. |
| 7,556,624 B2 * | 7/2009 | Laufer et al. ................. 604/514 |
| 7,720,549 B2 | 5/2010 | Schroeppel et al. |
| 7,742,811 B2 | 6/2010 | Schroeppel et al. |
| 7,837,670 B2 | 11/2010 | Barath |
| 8,014,854 B2 | 9/2011 | Schroeppel et al. |
| 8,024,048 B2 | 9/2011 | Schroeppel et al. |
| 9,211,155 B2 | 12/2015 | Fruland et al. |
| 9,597,145 B2 | 3/2017 | Nelson et al. |
| 10,004,551 B2 | 6/2018 | Burnett |
| 10,085,800 B2 | 10/2018 | Nelson et al. |
| 10,575,899 B2 | 3/2020 | Fruland et al. |
| 2001/0001314 A1 | 5/2001 | Davison et al. |
| 2001/0021868 A1 | 9/2001 | Herbst et al. |

(56) References Cited

U.S. PATENT DOCUMENTS

| | | | |
|---|---|---|---|
| 2001/0034518 | A1 | 10/2001 | Edwards et al. |
| 2002/0002329 | A1 | 1/2002 | Avitall |
| 2002/0026188 | A1 | 2/2002 | Balbierz et al. |
| 2002/0077676 | A1 | 6/2002 | Schroeppel et al. |
| 2002/0111618 | A1* | 8/2002 | Stewart .............. A61B 18/1492 606/41 |
| 2002/0115957 | A1 | 8/2002 | Sun et al. |
| 2002/0183735 | A1* | 12/2002 | Edwards et al. ................ 606/32 |
| 2003/0130711 | A1 | 7/2003 | Pearson et al. |
| 2003/0191504 | A1 | 10/2003 | Meadows et al. |
| 2003/0212394 | A1 | 11/2003 | Pearson et al. |
| 2004/0010290 | A1 | 1/2004 | Schroeppel et al. |
| 2004/0030334 | A1 | 2/2004 | Quick et al. |
| 2004/0059326 | A1* | 3/2004 | Flores .............................. 606/41 |
| 2004/0172089 | A1 | 9/2004 | Whitehurst et al. |
| 2004/0254618 | A1 | 12/2004 | Schroeppel et al. |
| 2005/0004438 | A1 | 1/2005 | Ward et al. |
| 2005/0004507 | A1 | 1/2005 | Schroeppel et al. |
| 2005/0010203 | A1 | 1/2005 | Edwards et al. |
| 2005/0054994 | A1 | 3/2005 | Cioanta et al. |
| 2005/0080409 | A1* | 4/2005 | Young ................ A61B 18/1482 606/41 |
| 2005/0131508 | A1* | 6/2005 | Garabedian ........ A61B 18/1477 607/122 |
| 2005/0159742 | A1 | 7/2005 | Lesh |
| 2005/0182449 | A1 | 8/2005 | Auge et al. |
| 2005/0197657 | A1 | 9/2005 | Goth et al. |
| 2005/0222623 | A1 | 10/2005 | Kroll et al. |
| 2005/0222646 | A1 | 10/2005 | Kroll et al. |
| 2005/0228373 | A1 | 10/2005 | Kelly et al. |
| 2005/0245923 | A1 | 11/2005 | Christopherson et al. |
| 2005/0283125 | A1* | 12/2005 | Barkhahn et al. ............ 604/272 |
| 2005/0288730 | A1* | 12/2005 | Deem et al. ..................... 607/42 |
| 2006/0025756 | A1 | 2/2006 | Francischelli et al. |
| 2006/0095032 | A1 | 5/2006 | Jackson et al. |
| 2006/0235286 | A1 | 10/2006 | Stone et al. |
| 2006/0259027 | A1 | 11/2006 | Kwan et al. |
| 2007/0016067 | A1 | 1/2007 | Webster, III et al. |
| 2007/0073391 | A1 | 3/2007 | Bourang et al. |
| 2007/0179491 | A1 | 8/2007 | Kratoksa et al. |
| 2007/0191925 | A1 | 8/2007 | Dorn |
| 2007/0255207 | A1* | 11/2007 | Hangai et al. ............. 604/96.01 |
| 2007/0260234 | A1 | 11/2007 | McCullagh et al. |
| 2008/0021275 | A1 | 1/2008 | Tearney et al. |
| 2008/0021445 | A1* | 1/2008 | Elmouelhi et al. ............. 606/41 |
| 2008/0027379 | A1* | 1/2008 | Wilkins ................... 604/103.08 |
| 2008/0071262 | A1* | 3/2008 | Azure .............................. 606/34 |
| 2008/0132885 | A1 | 6/2008 | Rubinsky et al. |
| 2008/0161804 | A1* | 7/2008 | Rioux ................ A61B 18/1477 606/41 |
| 2008/0243116 | A1 | 10/2008 | Anderson |
| 2009/0024075 | A1 | 1/2009 | Schroeppel et al. |
| 2010/0049031 | A1 | 2/2010 | Fruland et al. |
| 2010/0049188 | A1 | 2/2010 | Nelson et al. |
| 2010/0049192 | A1 | 2/2010 | Holtz et al. |
| 2010/0168777 | A1 | 7/2010 | Stangenes et al. |
| 2011/0106072 | A1 | 5/2011 | Sundquist et al. |
| 2011/0166569 | A1 | 7/2011 | Whayne et al. |
| 2011/0208022 | A1 | 8/2011 | Brawer et al. |
| 2012/0203307 | A1 | 8/2012 | Schroeppel et al. |
| 2014/0005676 | A1 | 1/2014 | Shelton, IV et al. |
| 2016/0184039 | A1 | 6/2016 | Shelton, IV et al. |
| 2016/0206370 | A1 | 7/2016 | Fruland et al. |
| 2017/0231693 | A1 | 8/2017 | Nelson et al. |
| 2020/0022748 | A1 | 1/2020 | Kroll et al. |

FOREIGN PATENT DOCUMENTS

| | | |
|---|---|---|
| EP | 2 326 274 | 6/2011 |
| WO | WO 1997/036632 A1 | 10/1997 |
| WO | WO 98/47562 A1 | 10/1998 |
| WO | WO 01/52931 A1 | 7/2001 |
| WO | WO 01/62336 A1 | 8/2001 |
| WO | WO 02/98501 A2 | 12/2002 |
| WO | WO 2005/086683 A2 | 9/2005 |
| WO | WO 06/042117 A2 | 4/2006 |
| WO | WO 08/083407 A1 | 7/2008 |
| WO | WO 2010/022275 A1 | 2/2010 |
| WO | WO 2010/022278 A1 | 2/2010 |
| WO | WO 2010/081730 A1 | 7/2010 |

OTHER PUBLICATIONS

PCT International Preliminary Report on Patentability, dated Feb. 22, 2011.
PCT Written Opinion, dated Feb. 22, 2011.
Application and File history for U.S. Appl. No. 12/544,112, filed Aug. 19, 2009. Inventors: Fruland et al.
EP09808837.0, EP Search Opinion, dated Apr. 11, 2012.
Reis A, Henninger T. Zerstorung maligner Wachstumsenergie durch anodische Oxydation. Kim Wochenschrift 1951; _: 39.
Nordenstrom B. Preliminary clinical trials of electrophoretic ionization in the treatment of malignant tumors. IRCS Med Sc 1978; 6: 537.
Schauble MK, Mutaz HB, Gallick HD. Inbitition of experimental tumor growth in hamsters by small direct currents. Arch Pathol Lab Med 1977; 101: 294.
Srinivasan S, Gahen Jr. GL, Stoner GE. Electrochemistry in the biomedical sciences. In: Bloom H, Gutmann F (eds): Electrochemistry the last thirty and the next thirty years. New York: Plenum Press, 1977.
Nordenstrom BEW. Biologically closed electric circuits: clinical, experimental and theoretical evidence for an additional circulatory system. Stockholm: Nordic Medical Publications, 1983.
Nordenstrom B. Biologically closed electric circuits: activation of vascular interstitial closed electric circuits for treatment of inoperable cancer. Journal of Bioelectricity 1984; 3(162): 137-153.
Lao, Y., Ge, T., Zheng, X., Zhang, J. Hua, Y., Mao, S., Feng, X. Electrochemical therapy for intermediate and advanced liver cancer: a report of 50 cases. Eur J Surg 1994; Suppl 574: 51-53.
Mir LM, Orlowski S, Belehradek Jr J, Paoletti C. Electrochemotherapy potentiation of antitumour effect of bleomycin by local electric pulses. Eur J Cancer 1991; 27:68-72.
Wolf B, Kraus M, and Sieben U, "Potential of microsensor-based feedback bioactuators for biophysical cancer treatment," Biosensors and Bioelectronics, vol. 12, No. 4, pp. 301-309, 1997.
Kirsch DL, Lerner FN. Electromedicine: the other side of physiology. In: Innovations in pain management: a practical guide for clinicians. Winter Park, FL: GR Press, 1995.
Li K, Xin Y, Gu Y, Xu B, Fan D. Ni B. Effects of direct current on dog liver: possible mechanisms for tumor electrochemical treatment . Bioelectromagnetics 1997; 18: 2-7.
Berendson J. Simonsson D. Electrochemical aspects of treatment of tissue with direct current. Eur J Surg 1994: Suppl 574: 111-115.
Song Y, Li C, Li Y, Song Q. Chang B, Song L. Liu C. Wang T. Electrochemical therapy in the treatment of malignant tumors on the body surface. Eur J Surg 1994; Suppl 574: 41-43.
Matsushima Y, Takahashi E, Hagiwara K, Konaka C, Miura H, Kato H, Koshiishi Y. Clinical and experimental studies of anti-tumoural effects of electrochemical therapy (ECT) alone or in combination with chemotherapy. Eur J Surg 1994; Suppl 574: 59-67.
Xin Y, Xue F, Ge B, Zhao F, Shi B, Zhang W. Electrochemical treatment of lung cancer. Bioelectromagnetics 1997; 18: 8-13.
Nordenstrom BEW. Electrochemical treatment of cancer. I: variable response to anodic and cathodic fields. Am J Clin Oncol (CCT) 1989; 12(6): 530-536.
Nordenstrom BEW. Survey of mechanisms in electrochemical treatment (ECT) of cancer. Eur J Surg 1994: Suppl 574: 93-109.
Chen B, Xie Z, Zhu F. Experimental study on electrochemical treatment of cancer in mice. Eur J Surg 1994; Suppl 574: 75-77.
Chou C, McDougall JA, Ahn C, Vora N. Electrochemical treatment of mouse and rat fibrosarcomas with direct current. Bioelectromagnetics 1997; 18: 14-24.
Nordenstrom BEW, Eksborg, S., Beving, H. Electrochemical treatment of cancer. II: effect of electrophoretic influence on adriamycin. Am J Clin Oncol (CCT)1990; 13(1): 75-88.

(56) References Cited

OTHER PUBLICATIONS

Xin, Y. Organisation and spread of electrochemical therapy (ECT) in China. Eur J Surg 1994; Suppl 577: 25-30.

Quan, K. Analysis of the clinical effectiveness of 144 cases of soft tissue and superficial malignant tumors treated with electrochemical therapy. Eur J Surg 1994; Suppl 574: 37-40.

Wang, H. Electrochemical therapy of 74 cases of liver cancer. Eur J Surg 1994; Suppl 574: 55-57.

Song, L., Liu, C., Zhang, B., Wang, T., Song, Y., Li, Y. Electrochemical therapy (ECT) for thyroid adenoma during acupuncture anaesthesia: analysis of 46 patients. Eur J Surg 1994; Suppl 574: 79-81.

Yokoyama, M., Itaoka, T., Nakajima, H., Ikeda, T., Ishikura, T., Nitta, S. [The use of direct current in the local destruction of cancer tissues]. Gan To Kagaku Ryoho Apr. 1989; 16(4 Pt 2-2): 1412-1417.

Okino, M. and Mohri, H. Effects of high voltage electrical impulse and an anti-cancer drug on growing tumors. Japanese Journal of Cancer Research, vol. 78, pp. 1319-1321, 1987.

Orlowski, S., Belehradek, J.J., Paoletti,C. And Mir, L.M. "Transient electropermeabilization of cells in culture increase of the cytotoxicity of anti-cancer drugs", Biochem, vol. 37, No. 24, pp. 4727-4733, 1988.

Belahradek, J.J., Orlowski, S., Raimiriz, L.H., Pron, G., Poddevin, B. and Mir, L.M., "Electropermeabilization of cells and tissues assessed by the qualitative and quantitative electroloading of bleomycin", Biochem. Biophys. Acta, vol. 1190, pp. 155-163, 1994.

Hofmann, G.A., Dev. S.B., Dimmer, S. and Nanda, G.S., "Electroporation Therapy: A new approach to the treatment of head and neck cancer, IEEE Transactions on Biomedical Engineering", vol. 46, No. 6, pp. 752-759, 1999.

Schecter, DC. "Containment of Tumors Through Electricity." PACE 1979. vol. 2, pp. 100-114.

Sersa, et al. Improvement of Combined modality therapy with cisplatin and radiation using electroporation of tumors. Int J. Radiation Oncology Biol. Phys. vol. 46, No. 4:1037-1041. (2000).

Hofmann, Dev, Nanda, and Rabussay. electroporation therapy of solid tumors. Critical Reviews in therapeutic Drug Carrier Systems 16(6):523-569 (1999).

Samuelsson, Harnek, Ewers, Jonsson. Electrochemical and megavolt treatment of rat tumors. Eur J Surg Suppl 574:69-70. (1994).

Habal and Schauble. An implantable DC power unit for control of experimental tumor growth in hamsters. Medical Instrumentation 7 No. 5: 305-306. (1973).

Semrov and Miklacic. Calculation of the electrical parameters inn electrochemistry of solid tumors in mice. Comp Biol Med 28:439-448. (2000).

Turler, Schaefer, et al. Local treatment of hepatic metastases with low level direct electrical current: experimental results. Scand J Gastroenterol. 3:322-328. (2000).

http://www.genetronics, retrieved Jul. 29, 2003.

Electro-Cancer Treatment, http://www.st-georg.com/ect.html, retrieved Oct. 25, 1999.

M. Belehradek, C. Domenge, B. Luboinski, S. Orlowski, J. Belehradek, Jr., L.M. Mir. Abstract of Electrochemotherapy, A new antitumor treatment. First clinical phase I-II trial. Cancer Dec. 15, 1993; 72(12):3694-700.

K. Brandisky, I. Daskalov. Abstract of Electrical Field and Current Distributions in Electrochemotherapy, Bioelectrochemistry and Bioenergetics Feb. 1999; 48(1):201-8.

M. Cemazar, G. Sersa and D. Miklavcic. Electrochemotherapy with Cisplatin in the Treatment of Tumor Cells Resistant to Cisplatin, Anticancer Research 18: 4463-4466 (1998).

S.L. David, D.R. Absolom, C.R. Smith, J. Gains, and M.A. Herbert. Effect of Low Level Direct Current on In Vivo Tumor Growth in Hamsters, Cancer Research 45, 5625-5631, Nov. 1985.

D. Liu, Y.L. Xin, B. Ge, F. Zhao, H.C. Zhso. Experimental Studies on Electrolytic Dosage of ECT for Dog's Oesophageal Injury and Clinical Effects of ECT for Oesopohageal Anastomotic Opening Stenosis and Oesophageal Carcinoma, European Journal of Surgery 1994; Suppl 574: 71-72.

R.A. Gatenby. Abstract of Mathematical Models of Tumour Invasion Mediated by Transformation-Induced Alteration of Microenvironment pH, Symposium 240: The Tumour Microenvironment: Causes and Consequences of Hypoxia and Acidity, p. 2-3, held at the Novartis Foundation, London, 240 Oct. 10-12, 2000.

L.F. Glass, N. A. Fenske, M. Jaroszeski, R. Perrott, D.T. Harvey, D.S. Reintgen, R. Heller. Abstract of Bleomycin-Mediated Electrochemotherapy of Basal Cell Carcinoma, Journal of the American Academy of Dermatology Jan. 1996; 34(1):82-6.

H. Gong, G. Liu. Effect of Electrochemical Therapy on Immune Functions of Normal and Tumour-Bearing Mice, European Journal of Surgery, Suppl 1994; (574): 73-74.

S.A. Grossman, P.S. Staats, Abstract of Current Management of Pain in Patients with Cancer. Oncology (Huntingt) Mar. 1994; 8(3):93-107.

M.B. Habal. Abstract of Effect of Applied DC Currents on Experimental Tumor Growth in Rats, Journal of Biomedical Materials Research, vol. 14, 789-801 (1980).

M.A. Hamza, P.F. White, H.E. Ahmed, E.A. Ghoname. Abstract of Effect of the Frequency of Transcutaneous Electrical Nerve Stimulation on the Postoperative Opioid Analgesic Requirement and Recovery Profile, Anesthesiology Nov. 1999;91(5):1232-8.

C. Hauton, M. Charbonnier, L. Cara and J.P. Salles, A New Type of Liposome for Electrochemical Treatment of Cancer: The Lipogelosomes, European Journal of Surgery 1994; Suppl 574: 117-119.

C.E. Humphrey, E.H. Seal. Biophysical Approach toward Tumor Regression in Mice, Science, vol. 130, 1959.

M. Kraus and B. Wolf. Implications of Acidic Tumor Microenvironment for Neoplastic Growth and Cancer Treatment: A Computer Analysis, Tumor Biology 1996; 17: 133-154.

M. Kraus and B. Wolf. Physicochemical Microenvironment as Key Regulator for Tumor Microevolution, Invasion, and Immune Response: Targets for Endocytotechnological Approaches in Cancer Treatment, Endocytobiosis & Cell Research, 12, 133-156 (1998).

Miklavcic, D. An, J. Belehradek, Jr., L.M. Mir. Abstract of Host's Immune Response in Electrotherapy of Murine Tumors by Direct Current, European Cytokine Network Sep. 1997;8(3):275-9.

D.M. Morris, M.D., A.A. Marino, Ph. D., and E. Gonzalez, M.D. Electrochemical Modification of Tumor Growth in Mice, Journal of Surgical Research 53, 306-309 (1992).

E. Nilsson. Modelling of the Electrochemical Treatment of Tumours. Dissertation, Department of Chemical Engineering and Technology, Applied Electrochemistry, Royal Institute of Technology, Stockholm 2000.

T. Nishi, S.B. Dev., K. Yoshizato, J. Kuratsu, Y. Ushio. Abstract of Treatment of Cancer Using Pulsed Electric Field in Combination With Chemotherapeutic Agents or Genes, Human Cell Mar. 1997;10(1):81-6.

G.D. O'Clock, Ph. D. (E.E.), P.E. The Effects of In Vitro Electrical Stimulation on Eukaryotic Cells: Suppression of Malignant Cell Proliferation, Journal of Orthomolecular Medicine, vol. 12, No. 3, 1997.

W.R. Panje, M.P. Hier, G.R. Garman, E. Harrell, A. Goldman, I. Bloch. Abstract of Electroporation Therapy of Head and Neck Cancer, Annals of Otology, Rhinology and Laryngology Sep. 1998; 107(9 Pt 1): 779-85.

A. Plesnicar, G. Sersa, L. Vodovnik, J. Jancar, L. Zaletel-Kragelj and S. Plesnicar. Electric Treatment of Human Melanoma Skin Lesions with Low Level Direct Electric Current: An Assessment of Clinical Experience Following a Preliminary Study in Five Patients, European Journal of Surgery 1994; Suppl 574:45-49.

N. Raghunand. Abstract of pH and Chemotherapy, Symposium 240: The Tumour Microenvironment: Causes and Consequences of Hypoxia and Acidity, p. 5-6, held at the Novartis Foundation, London, 240 Oct. 10-12, 2000.

L.H. Ramirez, S. Orlowski, D. An, G. Bindoula, R. Dzodic, P. Ardouin, C. Bognel, J. Belehradek Jr., J-N Munck, and L.M. Mir. Electrochemotherapy on Liver Tumours in Rabbits, British Journal of Cancer (1998) 77(12). 2104-2111.

M.K. Schauble, M.B. Habal. Electropotentials of Tumor Tissues. Journal of Surgical Research 9: 9, 1969.

S. Seguchi, S. Kawauchi, Y. Morimoto, T. Arai, H. Asanuma, M. Hayakawa, M. Kikuchi. Abstract of Critical Parameters in the

(56) References Cited

OTHER PUBLICATIONS

Cytotoxicity of Photodynamic Therapy Using a Pulsed Laser. Lasers Med Sci 2002, 17(4):265-71.
G. Sersa, M. Cemazar, D. Miklavcic and D. J. Chaplin, Tumor Blood Flow Modifying Effect of Electrochemotherapy with Bleomycin, Anticancer Research 19: 4017-4022 (1999).
B.N. Singh and C. Dwivedi. Antitumor Drug Delivery by Tissue Electroporation, Anti-Cancer Drugs 1999, 10, pp. 139-146.
T.V. Taylor, P. Engler, B.R. Pullan and S. Holt. Ablation of Neoplasia by Direct Current, British Journal of Cancer (1994), 70, 342-345.
A.L. Vandenbogaerde, E.M. Delaey, A.M. Vantieghem, B.E. Himpens, W.J. Merlevede, P.A. de Witte, Abstract of Cytotoxicity and Antiproliferative Effect of Hypericin and Derivatives After Photosensitization. Photochem Photobiol Jan. 1998;67(1):119-25.
P. Vaupel, D.K. Kelleher, M. Hockel. Abstract of Oxygen Status of Malignant tumors: Pathogenesis of Hypoxia and Significance for Tumor Therapy. Semin Oncol Apr. 2001; 28(2 Suppl 8):29-35.
L. Vodovnik, D. Miklavcic, G. Sersa. Modified Cell Proliferation Due to Electrical Currents, Medical and Biological Engineering and Computing, 1992, 30, CE21-CE28.
H. von Euler, Electrochemical Treatment of Tumours, Doctoral Thesis, Swedish University of Agricultural Sciences, Uppsala 2002.
J.C. Weaver. Electroporation: A General Phenomenon for Manipulating Cells and Tissues. J Cell Biochem 1993; 51 No. 4: 426-435.
M. Wojcicki, R. Kostyrka, B. Kaczmarek, J. Kordowski, M. Romanowski, M. Kaminski, J. Klonek, S. Zielinski. Abstract of Electrochemical Therapy in Palliative Treatment of Malignant Dysphagia: A Pilot Study, Hepatogastroenterology Jan.-Feb. 1999;46(25):278-84.
B. Wolf, M. Brischwein, W. Baumann, R. Ehret, T. Henning, M. Lehmann, A. Schwinde. Microsensor-Aided Measurements of Cellular Signalling and Metabolism on Tumor Cells, Tumor Biology 1998; 19:374-383.
Y.L. Xin, F.Z. Xue, F.G. Zhao. Effectiveness of Electrochemical Therapy in the Treatment of Lung Cancers of Middle and Late Stage, Chinese Medical Journal 1997 110(5): 379-383.
Y. Yen, J.R. Li, B.S. Zhou, F. Rojas, J. Yu and C.K. Chou. Electrochemical Treatment of Human KB Cells In Vitro, Bioelectromagnetics 20:34-41 (1999).
Y.L. Xin, D. Liu. Electrostatic Therapy (EST) of Lung Cancer and Pulmonary Metastasis: Report of 15 Cases. European Journal of Surgery 1994; Suppl 574: 91-92.
X.Z. Lin, C.M. Jen, C.K. Choud, D.S. Chou, M.J. Sung, T.C. Chou. Saturated Saline Enhances the Effect of Electrochemical Therapy. Digestive Diseases and Sciences 2000: 45(3): 509-514.
Damascelli B, Patelli G, Frigerio LF, Lanocita R, Di Tolla GD, Marchiano A., Spreafico C, Garbagnati F, Bonalumi MG, Monfardini L Ticha V, Prino A. First clinical experience with a high-capacity implantable infusion pump for continuous intravenous chemotherapy. Cardiovasc Intervent Radiol 1999; 22: 37-43.
Ranade VV. Drug delivery systems. 4. Implants in drug delivery. J Clin Pharmacol 1990; 30 No. 10: 871-889.
Buchwald H, Rohde TD. Implantable pumps. Recent progress and anticipated future advances. ASAIO J 1992; 38 No. 4: 772-778.
Wigness BD, Dorman FD, Robinson Jr HJ, Arendt EA, Oegema Jr TR,Rohde TD, Buchwald H. Catheter with an anchoring tip for chronic joint capsule perfusion. ASAIO Trans. 1991; 37 No. 3: M290-292.
Heruth KT, Medtronic SynchroMed drug administration system. Ann NY Acad Sci 1988; 531: 72-75.
Vogelzang NJ, Ruane M, DeMeester TR. Phase I trial of an implanted battery-powered, programmable drug delivery system for continuous doxorubicin administration. J Clin Oncol 1985; 3 No. 3: 407-414.

Application and File history for U.S. Appl. No. 09/524,405, filed Mar. 13, 2000, now U.S. Pat. No. 6,366,808, issued Apr. 2, 2002. Inventors: Schroeppel et al.
Application and File history for U.S. Appl. No. 09/974,474, filed Dec. 14, 2001, now U.S. Pat. No. 6,738,663, issued May 18, 2004. Inventors: Schroeppel et al.
Application and File history for U.S. Appl. No. 10/434,400, filed May 7, 2003, now U.S. Pat. No. 7,412,285, issued Aug. 12, 2008. Inventors: Schroeppel et al.
Application and File history for U.S. Appl. No. 10/792,256, filed Mar. 2, 2004, now U.S. Pat. No. 7,742,811, issued Jun. 22, 2010. Inventors: Schroeppel et al.
Application and File history for U.S. Appl. No. 12/173,639, filed Jul. 15, 2008, now U.S. Pat. No. 8,014,854, issued Sep. 6, 2011. Inventors: Schroeppel et al.
Application and File history for U.S. Appl. No. 13/226,319, filed Sep. 6, 2011. Inventors: Schroeppel et al.
Application and File history for U.S. Appl. No. 10/819,641, filed Sep. 6, 2011, now U.S. Pat. No. 7,720,549, issued May 18, 2010. Inventors: Schroeppel et al.
Application and File history for U.S. Appl. No. 10/881,375, filed Jun. 29, 2006. Inventors: Schroeppel et al.
Application and File history for U.S. Appl. No. 10/841,205, filed May 7, 2004, now U.S. Pat. No. 8,024,048, issued Sep. 20, 2011. Inventors: Schroeppel et al.
Application and File history for U.S. Appl. No. 12/544,119, filed Aug. 19, 2009. Inventors: Sundquist et al.
Application and File history for U.S. Appl. No. 12/544,127, filed Aug. 19, 2009. Inventors: Holtz et al.
Application and File history for U.S. Appl. No. 12/544,134, filed Aug. 19, 2009. Inventors: Nelson et al.
EP Application No. 037997616, EP Search Report, dated Feb. 2, 2010.
EP Application No. 05733003.7, Search Report, dated Apr. 11, 2008.
EP 05733003.7, Office Action, dated Aug. 13, 2008.
EP Application No. 05733003.7, Examination Report, dated Apr. 21, 2009.
PCT/US2003/14104, International Search Report, dated Nov. 18, 2004.
PCT/US2005/011430, PCT International Written Opinion, dated Jan. 13, 2006.
PCT/US2009/54528, PCT International Search Report, dated Oct. 22, 2009.
PCT/US2009/054523, PCT International Preliminary Report on Patentability and Written Opinion, dated Feb. 22, 2011.
EP 09808839.6, EP Search Opinion, dated Jul. 27, 2012, 1 page.
Gravante et al., "Experimental Application of Electrolysis in the Treatment of Liver and Pancreatic Tumours: Principles, Preclinical and Clinical Observations and Future Perspectives," Elsevier Ltd., ScienceDirect, dated Dec. 7, 2009, 15 pages.
Dalziel et al., "Let-Go Currents and Voltages," Transactions of the American Institute of Electrical Engineers, Part II: Applications and Industry, 75(2): pp. 49-56, 1956.
EP09808839.6, EP Summons to Attend Oral Proceedings, dated Sep. 13, 2018, 7 pages.
Application and File history for U.S. Appl. No. 14/969,889, filed Dec. 15, 2015. Inventors: Fruland et al.
Application and File history for U.S. Appl. No. 15/455,358, filed Mar. 10, 2016. Inventors: Nelson et al.
Application and File history for U.S. Appl. No. 16/148,756, filed Oct. 1, 2018. Inventors: Nelson et al.
Application and File history for U.S. Appl. No. 16/287,551, filed Feb. 27, 2019. Inventors: Kroll et al.
Application and File history for U.S. Appl. No. 16/201,642, filed Nov. 27, 2018. Inventors: Gilmour et al.

* cited by examiner

1

CATHETER FOR TREATING TISSUE WITH NON-THERMAL ABLATION

CROSS-REFERENCE TO RELATED APPLICATIONS

This application claims priority to U.S. Provisional Patent Application Nos. 61/090,600, filed Aug. 20, 2008; 61/090,519, filed Aug. 20, 2008; and 61/090,594, filed Aug. 20, 2008; and 61/090,589, filed Aug. 20, 2008; and is related to the following U.S. Patent Applications:

Ser. No. 12/544,112 entitled "Non-Thermal Ablation System for Treating BPH and Other Growths", filed on Aug. 19, 2009;

Ser. No. 12/544,119, entitled "Low-Corrosion Electrode for Treating Tissue", filed on Aug. 19, 2009; and Ser. No. 12/544,134, entitled "Non-Thermal Ablation System Treating Tissue", filed on Aug. 19, 2009.

The contents of each of the above listed applications are hereby incorporated by reference herein in their entireties.

FIELD OF THE INVENTION

The present invention relates generally to systems and methods for treating tissue and, more specifically, to systems and methods for non-thermal treatment of tissue.

BACKGROUND

Enlargement of the prostate gland (known as benign prostatic hyperplasia or hypertrophy—"BPH") is a common ailment in older men. BPH affects 40% of men in their 50s and 90% of men in their 80s. The enlargement of the prostate is a form of benign tumor or adenoma. FIG. 1 illustrates a simplified view of the anatomy and location of the prostate 3, 4. The urethra 1 passes upwards through the external urethral sphincter 2, through the prostate 3, 4 (surrounding the urethra), and into the bladder 5. The prostate 3, 4 comprises three lobes: two major lobes 3, 4 and a median lobe. The median lobe is located generally behind the major lobes 3, 4.

As the prostate becomes enlarged, it may compress the urethra and cause one or more of the following symptoms to occur: more frequent urination, weak urine stream, inability to delay urination, difficulty starting and stopping urination, incomplete emptying of the bladder, loss of bladder control, and painful or bloody urination.

If symptoms are mild and do not affect quality of life, treatment may not be performed. If diagnosed with BPH but not pursuing treatment options, men typically receive regular checkups and report increased BPH symptoms to the physician. If symptoms occur and cause discomfort, affect activities of daily living, or endanger health, drug treatment or surgery may be recommended. Treatment options for BPH include lifestyle changes (such as adjusting fluid intake), herbal remedies, drug therapy, non-surgical procedures, and surgical procedures. The goals of treatment are generally to improve urinary flow and decrease symptoms associated with BPH. Treatment may delay or prevent the progression of BPH.

Drugs may be used to relieve the common urinary symptoms associated with BPH by either reducing the size of the prostate gland or by slowing the growth of the prostate. Common drug classes used to treat urinary symptoms include alpha blockers, such as doxazosin or tamsulosin, and 5-alpha reductase inhibitors, such as finasteride or dutasteride. The medications may have deleterious side effects such as decreased libido, impotence, retrograde ejaculation, fatigue, dizziness, headache, and decreased blood pressure. If drug therapy does not provide adequate relief of symptoms, surgery may be needed to help correct the prostate gland overgrowth. Further, if more severe symptoms of BPH present, such as recurrent urinary retention, recurrent blood in the urine, recurrent urinary tract infections or bladder stones, drug therapy should not be initiated. Generally, upon presentation of these symptoms, surgery is indicated.

Surgical treatments of BPH may or may not be minimally invasive. For the surgical methods, access to the prostate may be via the urethra, the perineum, or other route.

Non-minimally invasive surgical treatments include Trans Urethral Resection of the Prostate (TURP). Conducted in an operating room under general or spinal anesthetic, a probe is passed through the urethra which scrapes away prostate tissue causing the blockage. Side effects may include retrograde ejaculation, impotence, and a repeat of the procedure if the blockage regrows. U.S. Pat. No. 6,491,672, herein incorporated by reference, discloses one surgery option for treating BPH.

Minimally invasive surgical treatments usually offer the incentives of less pain, faster recovery, lower costs, and use of local anesthesia and a mild sedative. In general, minimally invasive surgical treatments destroy prostate tissue through one of various mechanisms. The destroyed prostate tissue may be reabsorbed by the body and/or discharged into the urine over a period of time. Minimally-invasive surgical treatment options include generation of heat, freezing, chemical means, and ultrasound to destroy prostate tissue. Care must be taken to avoid damaging sensitive areas adjacent the prostate such as nerves controlling sexual functions or the rectal wall.

Various types of laser treatment of BPH exist including laser prostatectomy, interstitial laser coagulation, photosensitive vaporization of the prostate, Holmium laser ablation of the prostate, and Holmium laser enucleation of the prostate (HoLEP). Laser prostatectomy uses a transurethral laser device to cut or vaporize obstructions. Interstitial Laser Coagulation uses a cystoscope through which a fiberoptic probe is directly introduced into the prostate. A small laser fiber is inserted into the prostate through the device inserted in the urethra. Laser energy heats a selected area and the probe may be moved several times to treat all areas of obstruction. Photosensitive vaporization of the prostate (PVP) uses a laser delivered through an endoscope inserted into the urethra. The high-energy laser vaporizes excess prostate tissue and seals the treated area.

For microwave treatment of BPH, a microwave antenna is inserted transurethrally into the prostate. Various forms of microwave treatment may include a cooling means for minimizing patient discomfort and to protect adjacent urethral tissue from damage. Further means may be used to dilate the urethra.

Heat for treatment of BPH may be generated, for example, via laser beams, microwaves, radiofrequency current, or direct current. Other heat application techniques exist for treating BPH including transurethral vaporization of the prostate (TUVP) wherein heat is applied directly to the prostate with a grooved roller bar that vaporizes tissue and water-induced thermotherapy (WIT) to destroy obstructive tissue wherein hot water flows through a transurethrally-placed balloon. U.S. Pat. Nos. 5,928,225 and 6,640,139, herein incorporated by reference in their entirety, further disclose treatment methods using heat.

Non-thermal treatments of BPH include injection of ethanol (see, for example, U.S. Pat. No. 7,015,253) or direct current ablation (see, for example, U.S. Pat. Nos. 7,079,890; 6,733,485; and 6,901,294).

Transurethral ethanol ablation of the prostate (TEAP) may be used to treat BPH and typically uses a cystoscope with a curved needle to inject ethanol in various doses.

High intensity focused ultrasound (HIFU) may be used to treat BPH and noninvasively focuses ultrasound waves to heat and destroy targeted prostate tissue.

Various radiofrequency current treatment methods of BPH have been developed. Some methods are shown and described in U.S. Pat. Nos. 6,106,521; 6,638,275; and 6,016,452, all herein incorporated by reference in their entireties. In one treatment method, transurethral needle ablation, a small needle is inserted into the prostate from the urethra. Radio frequency (RF) energy is applied to the needle to generate heat in specific areas of the prostate. RF frequency based ablation of tissue is done via thermal treatment. Typically, treatment is done until a certain temperature is reached and is then discontinued. An assumption is made that sufficient ablation has occurred on the basis of the reached temperature.

As may be appreciated, many of these BPH treatment methods include transurethral access. Transurethral access may involve catheter-based electrodes within the prostatic urethra (see, for example, U.S. Pat. Nos. 6,517,534 and 5,529,574) or electrodes designed to puncture the urethra and dwell inside the prostate (see, for example, U.S. Pat. Nos. 6,638,275; 6,016,452; 5,800,378; and 5,536,240), transurethral access including balloons for positioning and stabilizing the electrodes (see, for example, U.S. Pat. Nos. 6,517,534 and 7,066,905), transurethral access including means for puncturing the urethral wall (see, for example, U.S. Pat. No. 5,385,544), and transurethral access including means for more accurately placing the electrodes (see, for example, U.S. Pat. No. 6,638,275).

Accordingly, a need exists in the art for a minimally invasive low power, non-thermal method of treating prostate tissue via direct current ablation.

BRIEF SUMMARY

Systems and methods for treating tissue, and particularly systems and methods for non-thermal ablation of tissue, are provided. In various embodiments, the systems and methods use a non-implantable system employing direct current ablation for targeting the area to be treated. DC current ablates tissue by imparting extreme pH into the tissue surrounding the electrode. In general, the systems and methods may be used to treat any form of tissue where ablation is desired including, for example, adipose tissue, muscular tissue, glandular tissue, nodular tissue, and fibrous tissue. In specific embodiments, the systems and methods may be used to treat benign prostatic hypertrophy or hyperplasia (BPH). In other embodiments, the systems and methods may be used to treat cancerous tissue and benign tumors. One skilled in the art will appreciate that specifics of the systems and methods may be modified for access to various sites in the body for treating different tissues.

In one embodiment, a catheter for use in a system for treating tissue in a body using direct current ablation is provided. The catheter includes a tubular body having a proximal end, a distal end, and a tip positioned at the distal end. The tubular body is semi-flexible, bi-directionally torqueable, and chemically resistant. The tubular body includes a plurality of routing holes provided between the proximal end and the distal end for facilitating deployment of electrodes from the tubular body. The tubular body further comprises an inner sheath generally at an interior portion and an outer sheath generally at an exterior portion and being chemically resistant. The tubular body has a flex modulus of between about 0.4 and 3 GPa.

In another embodiment, a catheter for use in a system for treating tissue in a body using direct current ablation is provided including a tubular body and a fixation element. The tubular body is semi-flexible, bi-directionally torqueable, and chemically resistant. The tubular body includes a plurality of routing holes provided between the proximal end and the distal end for facilitating deployment of electrodes from the tubular body. The tubular body further comprises an inner sheath generally at an interior portion and an outer sheath generally at an exterior portion and being chemically resistant.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed description is to be regarded as illustrative in nature and not restrictive.

BRIEF DESCRIPTION OF THE DRAWINGS

FIG. 10b illustrates an end view of the catheter of the system of FIG. 10a.

FIG. 22b illustrates an electrical diagram of the embodiment of FIG. 22a.

FIG. 51b illustrates a further view of the half of the rotational electrode deployment catheter spool of FIG. 51a.

FIG. 65b illustrates the pneumatic deploying electrode catheter of FIG. 65a.

FIG. 72b illustrates the Nitinol anode of FIG. 72a after the test was stopped.

FIG. 73 illustrates results from the first two stages of human prostate tissue study.

FIG. 74 is an in vivo image illustrating the necrotic volume achieved by the transurethrally ablating tissue with DC ablation.

DETAILED DESCRIPTION

Systems and methods for treating tissue, and particularly systems and methods for non-thermal ablation of tissue, are provided. In various embodiments, the systems and methods use a non-implantable system employing direct current ablation for targeting the area to be treated. DC current ablates tissue by imparting extreme pH into the tissue surrounding electrode. DC current ablation uses low power to treat tissues and creates necrosis without a significant increase in tissue temperatures. In general, the systems and methods may be used to treat any form of tissue where ablation is desired including, for example, adipose tissue, muscular tissue, glandular tissue, nodular tissue, and fibrous tissue. In specific embodiments, the systems and methods may be used to treat benign prostatic hypertrophy or hyperplasia (BPH). In other embodiments, the systems and methods may be used to treat cancerous tissue and benign tumors. One skilled in the art will appreciate that specifics of the systems and methods may be modified for access to various sites in the body for treating different tissues.

Ablation of pathologic tissue can be performed using low level DC current. This may be done by powering multiple electrodes and imparting a high pH at one polarity electrode and a low pH at the opposite polarity electrode. Generally, DC ablation resists diffusing across tissue boundaries and thus can be used to treat tissue with minimal concern to affecting adjacent tissues. Further, in systems employing a plurality of electrodes, treatment may be done with relatively slow application of DC current with the total treatment time reduced by the plurality of electrodes.

System Overview

Figure 1:
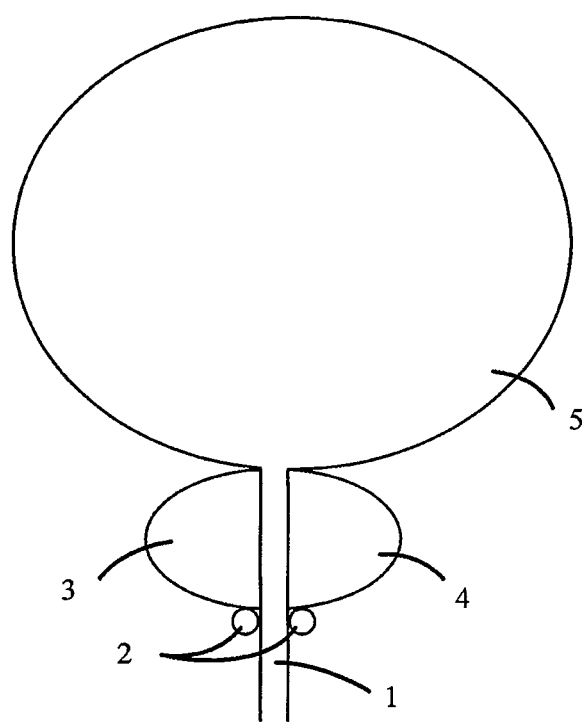
FIG. 1 illustrates a block anatomy diagram of the prostate area.
Figure 2A:
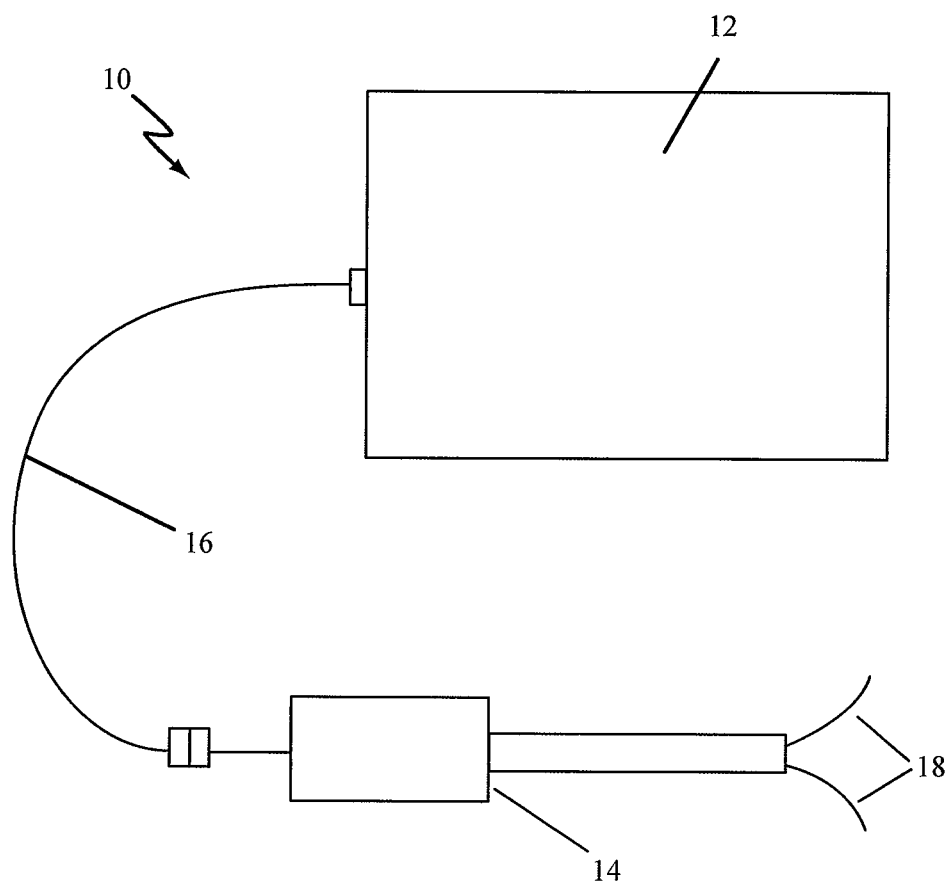
FIG. 2a illustrates a system for treating tissue, in accordance with one embodiment.

FIG. 2a illustrates a basic system configuration. As shown, the system 10 includes a generator 12, a catheter 14, electrodes 18, and a cable 16 running from the generator 12 to the catheter 14. The catheter 14 may be inserted in the body to a desired location for tissue treatment. Once positioned, the electrodes 18 may be deployed, for example through the catheter 14. To treat tissue, power is provided by the generator 12 to the electrodes 18. The electrodes then apply a DC current to a treatment area of the tissue. The tissue is thus treated by DC ablation in a non-thermal manner.

Figure 2B:
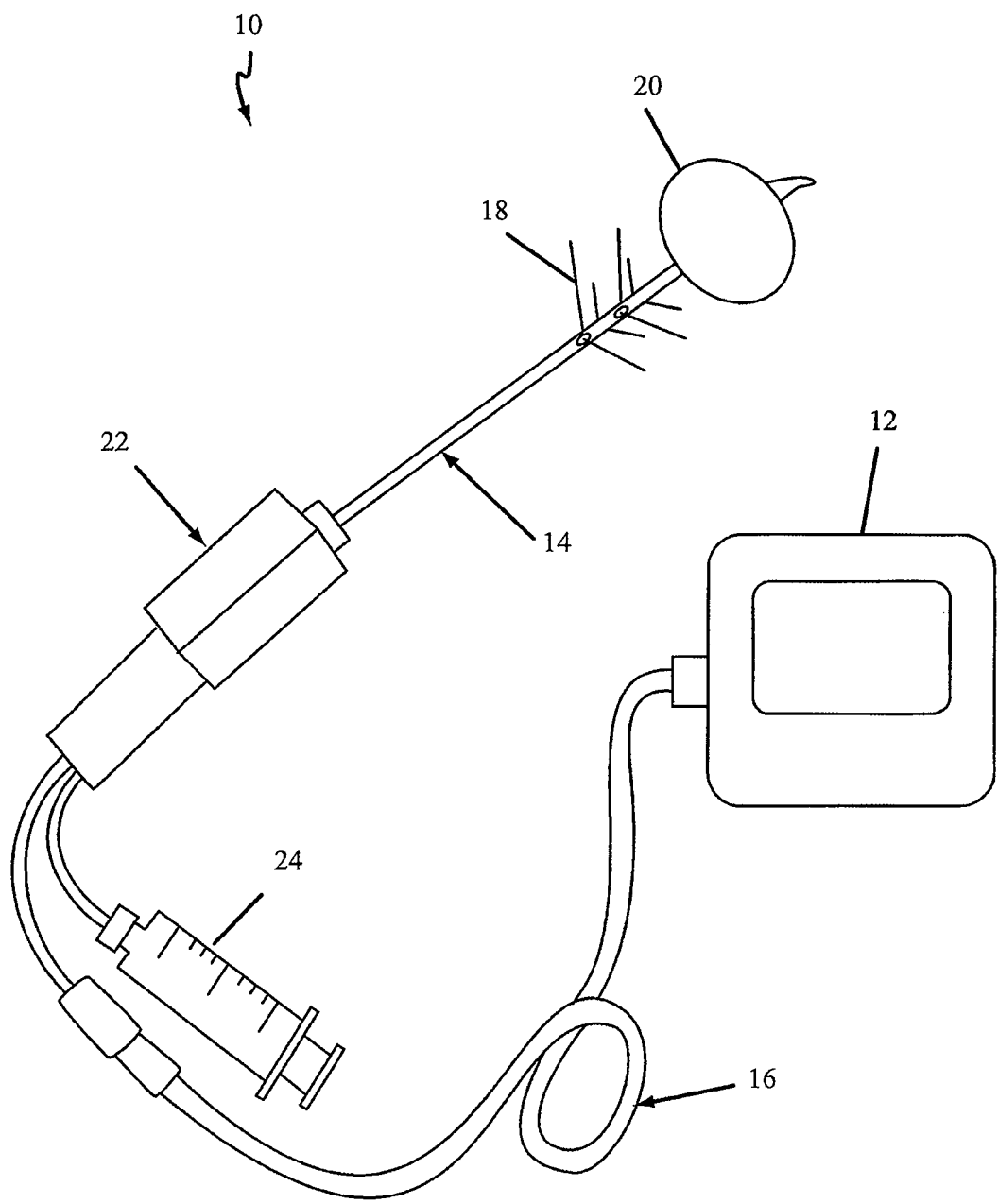
FIG. 2b illustrates a system for treating BPH, in accordance with one embodiment.

FIG. 2b illustrates an embodiment of the system of FIG. 2a configured for treatment of prostate tissue (or BPH treatment). As shown, the system 10 includes a generator 12, a catheter 14, an electrical connection 16 from the generator to the catheter, a plurality of electrodes 18, a mechanism 22 for deploying the electrodes, a stabilization mechanism or fixation element 20, and a mechanism 24 for deploying the stabilization mechanism. In various embodiments, the catheter 14 may be a transurethral catheter. In some embodiments, the electrodes 18 may be provided as pairs of electrodes. In some embodiments, an electronic control system may be included. The system and method may be used for treatment of BPH via deployment of the one or more electrodes through the transurethral catheter and application of direct electrical current to the one or more electrodes. In alternative embodiments, the system may comprise a catheter for other laparoscopic or percutaneous access to a treatment site. The electrodes produce a field of treatment that covers a predictable area of the target tissue. When deployed transurethrally, the electrodes can produce a field of treatment covering a predictable area of prostatic tissue. A necrotic zone may be created around each of the electrodes and the created necrotic zones coalesce to form the field of treatment. The field of treatment begins at the electrode and diffuses out generally passively.

The electrodes may be provided in any number, may have various shapes, may have various deployment configurations, and may be manufactured of various materials, as shown and discussed in copending U.S. patent application Ser. No. 12/544,119, herein incorporated by reference in its entirety. In some embodiments, the electrodes are provided in pairs. The ability to control the mechanical length, angle, and electrical polarity of each electrode, as well as the amount of current passing through each electrode allows debulking of a predictable region in a controlled manner while reducing risk of damage to adjacent, non-targeted areas. Generally, application of DC ablation to treat tissue will not result in scar tissue such as arises from other forms of treatment.

In the embodiment shown in FIG. 2b, the electrodes 18 are provided as four electrode pairs, each electrode being generally cylindrical. As shown, two of the electrode pairs comprise shorter electrodes and two of the electrode pairs comprise longer electrodes. Each electrode pair comprises an anode and a cathode. An anode is defined as the electrode with higher voltage potential. A cathode is defined as the electrode with the lower voltage potential. In the embodiment of FIG. 2b, the electrodes deploy outward from the catheter. Such outward deployment may be, for example, radial or may be linear. Generally, the electrodes may be coupled to the catheter or to a support structure in the catheter. As can be appreciated, the electrodes and their coupling with the catheter or a support structure provided within the catheter may be configured to extend from the catheter at different angles, for different lengths, etc. Angles of extension may further be influenced by the shape and configuration of the routing holes. The various system configurations may be designed based on the tissue to be treated and a selected access route to the tissue to be treated. In some embodiments, for example, the system may be configured for treatment of prostate tissue, or more specifically, for treatment of a large region of prostate tissue.

The electrodes 18 are configured for puncture and proper placement of the electrode tip to create a desired treatment area. The electrodes 18 further are configured to resist corrosion. In some embodiments, the electrodes 18 may comprise a Nitinol wire with a corrosion resistant coating. The corrosion resistant coating may be, for example, platinum. In some embodiments, the electrodes may be configured to be atraumatic. In an embodiment comprising needle electrodes, for, example, the tip of the needle electrode may be self-introducing. Using a transurethral approach, deployment of the electrodes comprises extension from the transurethral catheter and through the urethra. Accordingly, the electrodes pierce the urethra. Thus, in embodiments for treating BPH, the electrode tip may be sufficiently sharp to penetrate the urethra.

In use, current is supplied to the electrodes to create a reaction around the electrodes to change the structure of the tissue in a treatment zone around the electrodes. The system thus may further include a generator for supplying current to the electrodes. The non-thermal ablation system generally is a lower power system, using, for example, on the order of milliwatts. The system thus does not create significant heat during treatment, thus mitigating side effects often associated with thermal treatment. The size and shape of the treatment zone varies depending on, at least, treatment time, current delivered, electrode size and shape, and positioning of the electrode relative to tissue boundaries. As a general matter, by using a plurality of electrodes that are properly placed, treatment may be done at a relatively slow rate but the total treatment time may be relatively fast. The shape of the treatment zone around a cylindrical electrode, such as shown in FIG. 2b, is approximately an ellipsoid or cylinder with hemispheric ends with the distance from the boundary of the treatment zone and the surface of the electrode having a generally consistent radius, referred to herein as the radius of treatment.

Figure 3A:
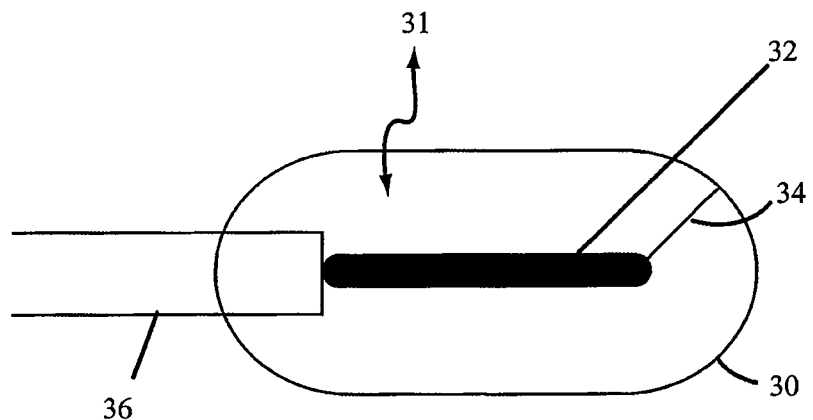
FIG. 3a illustrates a side view of an electrode, radius of treatment, and treatment zone, in accordance with one embodiment.
Figure 3B:
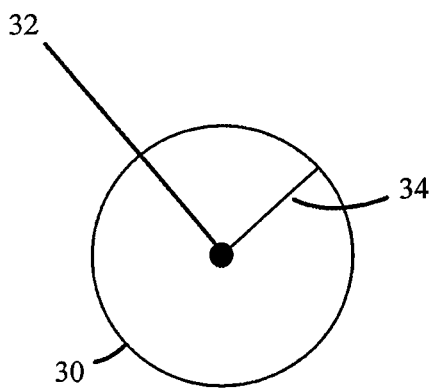
FIG. 3b illustrates an end view of an electrode, radius of treatment, and treatment zone, in accordance with one embodiment.

FIG. 3a illustrates a side view and FIG. 3b illustrates an end view of an active electrode. As shown, the electrode 31 includes an active portion 32 and an insulated portion 36. The insulated portion 36 of the electrode is resistant to the corrosive environment created during ablation. FIGS. 3a and 3b further illustrate the radius of treatment 34, treatment zone 30 associated with the active portion 32 of the electrode 31.

Figure 4A:
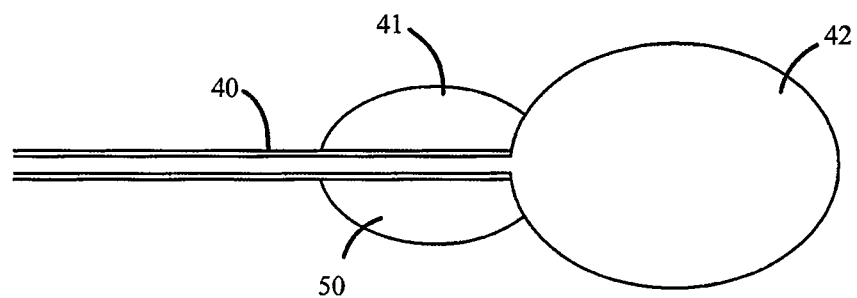
FIG. 4a illustrates anatomy of a prostate region prior to deployment of a device for treating tissue.
Figure 4B:
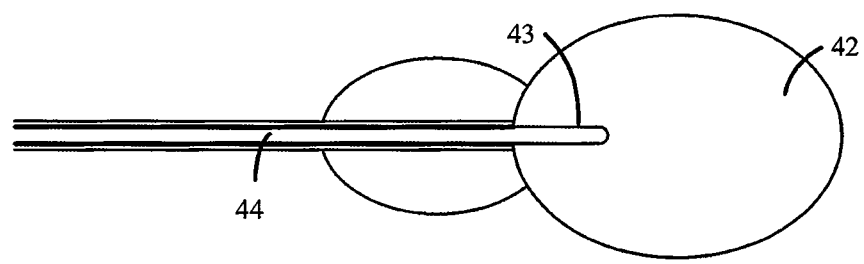
FIG. 4b illustrates transurethral insertion of a catheter for deployment of a device for treating tissue, in accordance with one embodiment.
Figure 4C:
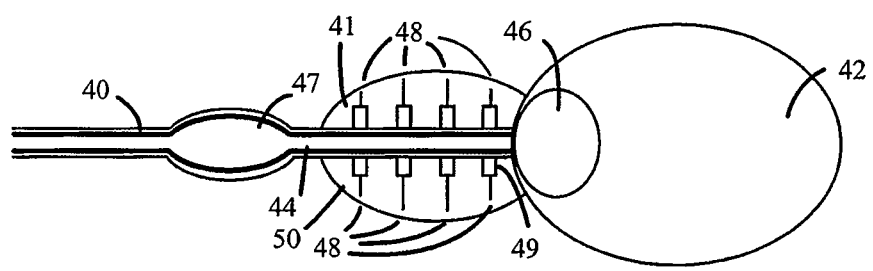
FIG. 4c illustrates deployment of electrodes, in accordance with one embodiment.

FIGS. 4a-4c illustrate deployment of a device for treating tissue in a prostate region, in accordance with one embodiment. Specifically, FIGS. 4a-4c illustrate the device relative the urethra 40, prostate gland 41, prostate capsule or wall 50, and bladder 42. Before treatment, the tissue to be treated may be assessed to determine appropriate treatment protocol. FIG. 4a illustrates a simplified diagram of the anatomy of a prostate region prior to deployment of a device for treating tissue. FIG. 4b illustrates transurethral insertion of the catheter 44 and shows the distal end 43 of the catheter 44. FIG. 4c illustrates deployment of the electrodes 48 and their insulation sleeves 49 through the catheter 44; with the catheter 44 generally fixed in place by one or more balloons 46, 47 (or other fixation element).

FIG. 4b illustrates an embodiment for BPH treatment wherein a catheter 44 is inserted transurethrally. In various embodiments, the catheter 44 may be flexible or semi-flexible or semirigid distally from the entrance of the urethra, as deployed. In one embodiment the catheter body has a flex modulus of between about 0.4 and 3 GPa. The catheter may be advanced with the guidance of a trans-rectal ultrasound (TRUS). In FIG. 4b, the distal end 43 of the catheter 44 is shown inserted in the bladder 42. The catheter 44 may include one or more balloons 46 and 47, as shown in FIG. 4c. To fix the system in place, one balloon 46 is expanded within the bladder and one balloon 47 is expanded in the urethra 40. Other anchoring mechanisms or fixation elements may alternatively be used. In some embodiments, the balloon 46 expanded within the bladder 42 assists in placement of the catheter 44. For example, the balloon 46 may be inflated after the catheter tip has entered the bladder and the catheter may be retracted until resistance is felt by the balloon 46. The balloons further may assist in maintaining the catheter in a treatment position. Various methods of imaging, such as ultrasound using a rectal probe, may be used to help position the catheter.

FIG. 4c illustrates electrode deployment after anchoring of the catheter. In the embodiment of FIG. 4c, the catheter 44 includes eight needle electrodes 48 at four different positions on the catheter 44. The electrodes 48 and their electrical insulation sleeves 49 pierce the urethra 40 and enter the prostate 41. As shown, the length of the electrodes 48 may be varied to optimize the field of treatment for the given size and shape of the prostate 41. In the deployment position, none of the electrodes 48 pierce the prostate wall 50. After the electrodes have been positioned, current is applied to create acidic and basic zones and thus ablate tissue in the treatment zone. In embodiments comprising eight electrodes, the system may be used to create eight necrotic zones in a single deployment. Thus, the treatment may be performed with a single deployment, employing relatively slow treatment with respect to application of current but having relatively fast treatment time because all treatment zones may be formed substantially simultaneously. This decreases physician time and burden to deliver the treatment to patients.

In some embodiments for treatment of BPH, the cathode may be placed proximate the bladder neck or base of the prostate. A cathode so placed creates a large area of necrosis with less relative variation. Because of the edemic reaction at the cathode, the healing response and resorption of tissue into the body (and associated relief of symptomatic BPH) is accelerated. The area closest to the bladder neck in the prostate is responsible for the greatest contribution to lower urinary tract symptoms due to BPH. The anode may be placed closer to the verumontanum or as an indifferent electrode. Another embodiment includes placing the cathodes in the lateral posterior quadrant of the tissue relative to the urethra and placing the anodes in the lateral or lateral anterior quadrant of the tissue relative to the urethra. A treatment zone forms around each of the electrodes and diffuses out generally passively. Thus, the electrodes may be placed in the tissue relative to each other such that the treatment zones overlap and coalesce. In one embodiment an indifferent electrode is used as either the anode or cathode in addition to the electrodes in the catheter which create the treatment zones. The indifferent electrode can be a patch electrode that makes contact with the skin of the patient. In one embodiment the patch is placed on the buttocks of the patient. The indifferent electrode may have a substantially large surface area to reduce the electrochemical affect on the skin. In one embodiment indifferent electrode incorporates a flushing system to maintain a neutral pH at the surface of the skin-electrode interface.

Method of Treatment

Figure 5:
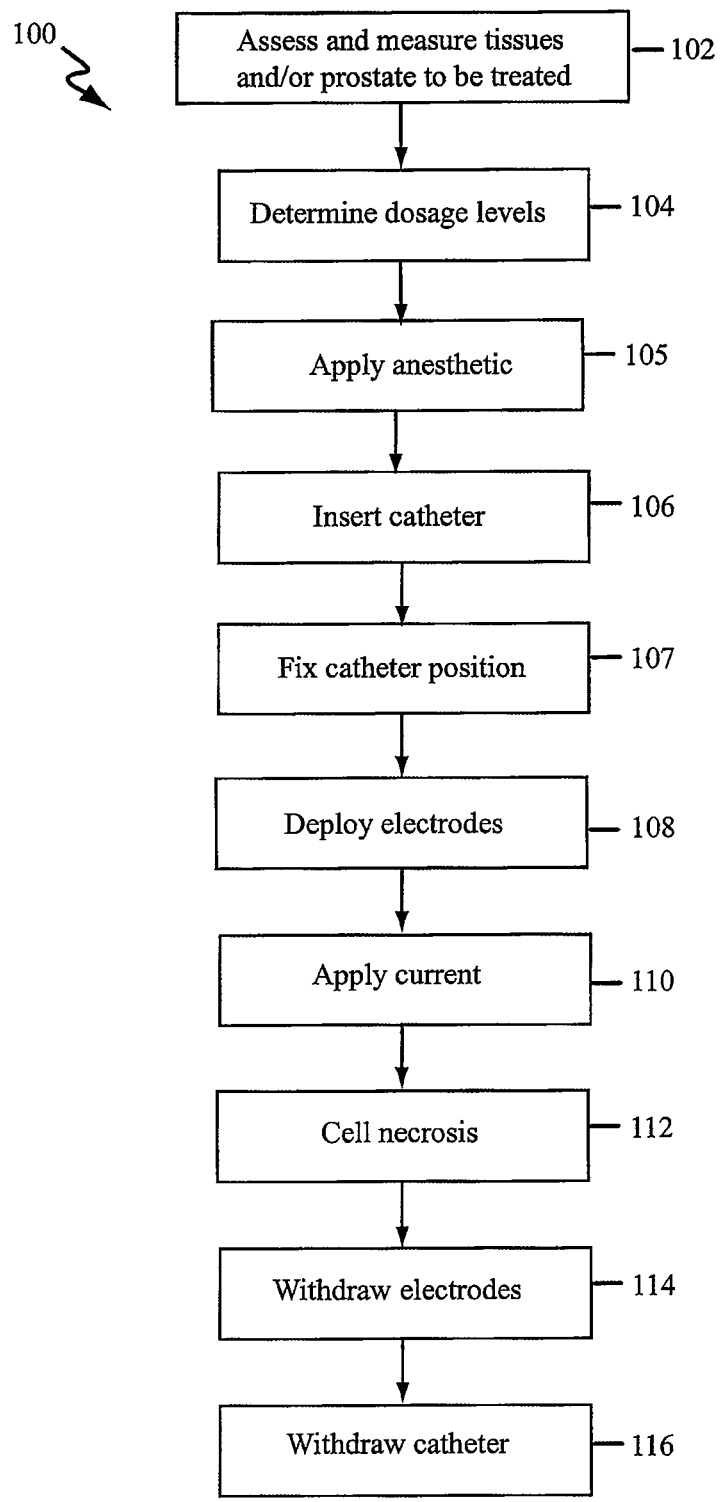
FIG. 5 illustrates a block diagram of a method for treating tissue, in accordance with one embodiment.

FIG. 5 illustrates a block diagram of a method 100 for treating tissue. In the embodiment shown, the method comprises assessing and measuring the prostate or other tissue to be treated [block 102], determining dosage levels [block 104], application of an anesthetic [block 105], inserting a catheter [block 106] and fixing the position of the catheter with a fixation element [block 107], deploying electrodes via the catheter[block 108], applying current to the electrodes to create acidic and basic treatment zones [block 110], cell necrosis [block 112], withdrawal of the electrodes [block 114], and withdrawal of the catheter [block 116]. It is to be appreciated that, in some embodiments, not all of these steps may be performed and/or additional steps may be performed. Further, in some embodiments, one or more of the steps may be performed in a manner other than specifically disclosed herein.

In treatment of BPH, prostate size may vary considerably and selection of appropriate number and size of electrodes to deploy may vary based on size of the prostate. Generally, using systems and methods such as disclosed herein, a minimum of 4 electrodes will be deployed. In some embodiments, eight electrodes, with eight associated treatment zones are provided and deployed in a single deployment. To evaluate the number and size of electrodes for deployment and/or dosage levels, it may be desirable to examine the patient to determine size of the tissue area to be treated. Such examination may be visual, tactile, or other. In one embodiment, examination may be done using a cystoscope, a tubular instrument used to visually examine the interior of the urinary bladder and urethra. In various embodiments, the location for electrode deployment may be determined by estimating the size and shape of the prostate through cystoscopy and/or transrectal ultrasound (TRUS) and/or other suitable imaging method. Other options include CT, MRI, PET, or X-ray. Treatment zone size may also be determined to minimize interaction with the prostate capsule and the prostatic urethra. Minimizing treatment interactions with the capsule and prostatic urethra will reduce the amount of irritative urinary symptoms after treatment. An appropriate system configuration thus may be selected based on the prostate size to be treated to minimize these interactions. Dosage levels may be determined based on the assessed treatment area. The desired treatment area can be determined by measuring the overall prostate dimension such as transverse width, sagittal length, and anterior to posterior height. Generally, the most important anatomical dimension to determine treatment may be the prostate transverse width. Diffusion through tissue is typically predictable, thus facilitating dosage setting.

In one embodiment, the generator is configured to display the predicted areas of necrosis over an uploaded image from ultrasound. In other embodiments, other imaging devices may be used to provide such imagery. The size and shape of the treatment zone varies with the charge setting inputted into the generator. In some embodiments the generator is configured to communicate with an ultrasound machine overlaying the predicted treatment zone on the ultrasound image. In embodiments wherein the system is used for treatment of prostate, imaging may be used prior to insertion of the system. Such imaging may be, for example, a rectal ultrasound whereby the prostate is measured. Measurements of the prostate may then be compared to a table to determine appropriate length of insertion and dose for treatment.

Block 104 of FIG. 5 may include entry of input treatment parameters into the generator. In some embodiments, the generator may include switches, keys or buttons for the entry of one or more input treatment parameters by the user of the system and those input treatment parameters may be used by the generator to control the delivery of current. During treatment, the generator may compare measured treatment parameters with input treatment parameters to determine when to pause or stop the treatment. In one embodiment, the input treatment parameter may be dose (charge) in coulombs. During treatment, the generator stops treatment when the measured charge is greater than or equal to the charge entered by the user. In another embodiment, input treatment parameters may be current level and time. During treatment, the generator may stop treatment when the measured charge is greater than or equal to the product of the current level and time input parameters. In another embodiment, the input treatment parameter may be current level. During treatment, the generator may pause or stop treatment if the measured current level exceeds the current level input parameter. In another embodiment, the input treatment parameter may be time with a predetermined current level.

The following look-up tables can be a guide for determining the charge to be delivered and the length of insertion of the electrodes into prostates with varying transverse widths to optimize treatment.

Table 1 shows optimized treatment settings for a catheter which has electrodes that extend outward from the catheter generally perpendicular from the catheter body (Extension angle between 60 and 120 degrees) (The active length of the electrode is assumed to be 6 to 8 mm in this table):

TABLE 1

| Prostate Transverse Width (mm) | Dose or Charge (C) | Expected Treatment Zone Radius around each electrode (mm) | Electrode Extension Length (mm) |
|---|---|---|---|
| 30-40 | 36-48 | 5-7 | 13 |
| 40-50 | 40-52 | 6-8 | 16 |
| >50 | 48-60 | 7-9 | 20 |

Table 2 shows optimized treatment setting for a catheter which has electrodes that extend outward from the catheter towards the catheter tip with an extension angle of 45 degrees to 30 degrees. The active length of the electrode is assumed to be 6 to 8 mm in this table:

TABLE 2

| Prostate Transverse Width (mm) | Distal Electrode Insertion Point from Fixation Element in Bladder (mm) | Optimal Dose or Charge (C) per electrode | Expected Treatment Zone Radius around each electrode (mm) | Electrode Extension Length (mm) |
|---|---|---|---|---|
| >30 | 14-16 | 28-36 | 4-6 | 16 |
| >30 | 16-18 | 36-48 | 5-7 | 18 |
| >35 | 18-20 | 36-48 | 5-7 | 20 |
| >40 | 20-22 | 48-60 | 7-9 | 22 |

Table 3 shows optimized treatment setting for a catheter which has electrodes that extend outward from the catheter towards the catheter tip with an extension angle of 60 degrees to 45 degrees. The active length of the electrode is assumed to be 6 to 8 mm in this table:

TABLE 3

| Prostate Transverse Width (mm) | Distal Electrode Insertion Point from Fixation Element in Bladder (mm) | Optimal Dose or Charge (C) per electrode | Expected Treatment Zone Radius around each electrode (mm) | Electrode Extension Length (mm) |
|---|---|---|---|---|
| >30 | 12-14 | 28-36 | 4-6 | 16 |
| >35 | 14-16 | 36-48 | 5-7 | 18 |
| >40 | 15-17 | 36-48 | 5-7 | 20 |
| >45 | 16-18 | 48-60 | 7-9 | 22 |

Table 4 shows optimized treatment setting for a catheter which has electrodes that extend outward from the catheter towards the catheter tip with an extension angle of 30 degrees to 15 degrees. The active length of the electrode is assumed to be 6 to 8 mm in this table:

TABLE 4

| Prostate Transverse Width (mm) | Distal Electrode Insertion Point from Fixation Element in Bladder (mm) | Optimal Dose or Charge (C) per electrode | Expected Treatment Zone Radius around each electrode (mm) | Electrode Extension Length (mm) |
|---|---|---|---|---|
| >30 | 16-18 | 20-28 | 3-5 | 16 |
| >30 | 18-20 | 24-32 | 4-5 | 18 |
| >30 | 20-22 | 28-36 | 4-6 | 20 |
| >30 | 22-24 | 28-36 | 4-6 | 22 |

To determine how many electrodes should be used to treat a prostate a cystoscopy should be done to measure the distance between the bladder neck and the verumontanum. If the measurement is less than 2.5 cm the patient is not well suited to be treated with a catheter that has electrodes that angle away from the catheter of less than 60 degrees upon electrode extension (extension angle). Table 5 shows the number of electrodes that should be used in treating prostates with varying distances between the bladder neck and verumontanum with catheters with different extension angles. This assumes that 4 electrodes are placed in each plane along the urethra and each plane is spaced between 6 and 12 mm.

TABLE 5

| Cystoscopy Measurement between bladder neck and verumontanum (cm) | Optimal # of Electrodes in catheter with extension angle between 90 and 60 degrees | # of Electrodes in catheter with extension angle between 60 and 45 degrees | # of Electrodes in catheter with extension angle between 45 and 30 degrees | # of Electrodes in catheter with extension angle between 30 and 15 degrees |
|---|---|---|---|---|
| <2.5 | 4 | NA | NA | NA |
| 2.5-4.5 | 8 | 4 | 4 | 4 |
| >4.5 | 12 | 8 | 8 | 4 |

Figure 6A:
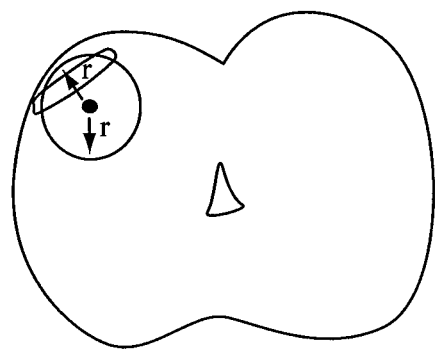
FIG. 6a illustrates a treatment zone for a dose that just touches the capsule, in accordance with one embodiment.
Figure 6B:
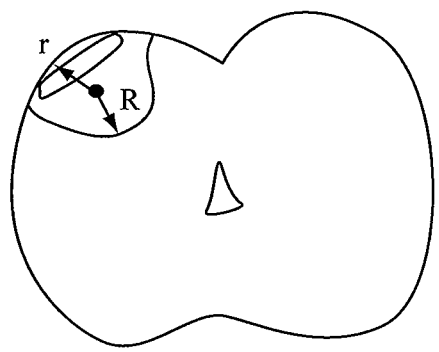
FIG. 6b illustrates a treatment zone for a dose that is overdosed, in accordance with one embodiment.

In some embodiments, the prostate capsule may be used as a safety margin to deliver DC ablation to the periphery zone of the prostate. Because of the capsule around the prostate and the creation of ions using DC ablation, the prostate can be overdosed to effectively treat the periphery zone, especially for applications for treating cancerous tissue. This overdose may range from approximately 160% to approximately 260% of the dose for allowing the ionic gradient to reach the prostate capsule. FIGS. 6a and 6b illustrate treatment zones for a dose that just touches the capsule (FIG. 6a) and a dose that is overdosed (FIG. 6b). A cancer is shown in each of the figures with the treatment radius of each electrode being suitable for treating the cancer. Each of FIGS. 6a and 6b show the same electrode placement. Dose typically may be determined assuming a radius that reaches the capsule but does not extend past the capsule, radius r shown in FIG. 6a. The dose may be increased to effectively increase radius but the radius r towards the capsule will not extend past the capsule because of the anatomy of the capsule. Thus, as shown in FIG. 6b, radius r towards the capsule remains the same but radius R away from the capsule increases. In one embodiment, the treatment radius in FIG. 6a is achieved using a dose of 30C and results in a radius r of 6 mm. In one embodiment, the treatment radius R in FIG. 6b is achieved using a dose of 78C and results in a radius R of 10 mm. An algorithm may be developed using routine experimentation for current and charge balancing to produce the desired treatment zone.

In some embodiments, the area for treatment may be prepared for treatment, as shown and discussed in copending U.S. patent application Ser. No. 12/544,134, herein incorporated by reference in its entirety. Unlike many ablation methods, DC ablation does not use extremes of temperature to cause necrosis and therefore can be used safely adjacent vascular structures.

In some embodiments, a saline solution or saline gel may be introduced to provide additional safety margin where ablation of tissue is not desired. In some embodiments, a saline solution with a pH of 7 may be provided adjacent to a treatment area. This substantially prevents the acidic and basic treatment zones from advancing into that area. The neutral pH of the saline dilutes the advancing acidic and basic gradient to a point which does not create necrosis in the tissue in irrigated areas. The saline solution may be delivered to an area by any suitable method. For example, in a first embodiment, saline may be introduced into a body lumen where preservation is desired, such as the urethra, through the therapy delivery catheter or through a separate dedicated irrigation catheter. In a second embodiment, saline may be injected through a needle into a capsule to preserve a certain region within the capsule. In a third embodiment, saline may be injected into a body cavity adjacent to the capsule of the body being treated to preserve adjacent tissue, such as the rectum. Saline saturation of the treatment area may further be done if a concern for dehydration arises. In other embodiments, distilled water may be used as an alternative to saline solution. As discussed with respect to application of current to the electrodes, muscle contractions may arise during treatment. Generally, muscle contractions are undesirable during treatment. A nerve block may be used in some embodiments to minimize patient discomfort during treatment. In some embodiments, anesthetic may be applied. It is to be appreciated, however, that the system and method disclosed herein are significantly more tolerable to patients than previous methods of BPH treatment and may be performed with minimal anesthetic. For example, the methods disclosed herein may be performed with the patient conscious.

Pain management during treatment according to the systems and methods provided herein may be done by local anesthesia. For example, in some embodiments application of anesthesia may comprise introducing a topical anesthetic gel (e.g. lidocaine) into the urethra. This may be done, for example, by injecting into the urethra or coating a catheter that would be inserted and removed prior to inserting the treatment catheter. Thus, in various treatment applications, anesthetic gel may be applied to a transperineal, transrectal, or transurethral catheter for delivery to the prostate or other tissue. In other embodiments, a nerve block may be injected locally or a sedative may be orally ingested or intravenously delivered.

In some embodiments, the method may include visualization, for example to facilitate placement and positioning of the system. Accordingly, visualization elements may be provided as part of the system. Particularly in systems employing a plurality of electrodes, such as eight electrodes, correct positioning can impact results. The positioning of the system impacts positioning of all electrodes and, thus, positioning of all necrotic zones. Accurate placement of transurethral catheters can be optimized with the use of a transrectal ultrasound. Ultrasound imaging may be optimized by designing the catheter or other portion of the system for imaging. The ability to image the system as the system is placed can enhance results and improve safety.

Magnetic resonance imaging may alternatively be used to verify position and treatment for the system for treating tissue as provided herein. In accordance with one method, the catheter is placed and the electrodes are inserted. The patient is positioned for MRI imaging and DC ablation is activated at low levels. MRI is performed, tuned to measure the electromagnetic field of DC current, and therapy is paused. The position of electrodes and treatment region are verified through examination of the MRI image. Generally, the imaging sequence may include electrical currents, via induced magnetic field, or $H^+$ concentration, such as for conventional MRI images, or other sequences such as known to those skilled in the art.

Angular orientation of the catheter and electrode array can be verified by a physical marker on the body of the catheter or handle that is exposed outside the body. In certain embodiments, this may be a linear marking or a bubble indicator. Such indicator may also be internal to the body and may be seen through imaging such as ultrasound, MRI, CT, or X-Ray The system may be deployed by inserting a catheter proximate the tissue to be treated such that the treatment zone of an electrode deployed from the catheter overlaps the tissue to be treated. The catheter may have a handle provided at a proximal end thereof for handling by a physician, such as a surgeon or urologist. The catheter is inserted until location of the electrodes, as determined with respect to the catheter, is at the desired tissue for treatment. Thus, for example for BPH treatment, the catheter may be inserted into the urethra through the penis until location of the electrodes is in the urethra proximate the prostate. In some embodiments, the catheter may include an anchor for anchoring the catheter in place during treatment. For example, a pair of pneumatically or hydraulically activated balloons may be used to anchor the catheter.

After anchoring (if done) and placement confirmation, the electrodes may be deployed from the catheter. Electrode deployment may be linear, rotational, or a hybrid of linear and rotational. Deployment of the electrodes may be triggered, for example, using a push button trigger, a slide mechanism, or other on the catheter handle. In some embodiments, the catheter may be partially retracted or advanced to expose electrodes provided on a support structure within the catheter. In some embodiments, the electrodes may be deployed through routing holes provided in an outer sheath or sleeve of the catheter. The electrodes may extend generally outwardly from the catheter to enter the tissue to be treated. The position of the electrodes in the tissue affects the treatment zone. More particularly, the treatment zone generally surrounds the electrodes In some embodiments, the inserted length of all deployed electrodes may be approximately equivalent. This permits the electrodes to be deployed with a single simple mechanism. In other embodiments, multiple insertion lengths may be used. Such varied insertion lengths may be achieved, for example, with multiple insertion mechanisms or various cam and/or gearing mechanisms. Treatment zones around each electrode may be the same size or may vary one to another. The amount of charge to each electrode may be controlled to influence treatment zones. For example, where varying sizes of treatment zones are desired and each electrode has the same length, different currents may be supplied to the electrodes from independent current sources. Further, in some embodiments, portions of the electrode may be insulated, for example portions closest to the catheter to increase the distance from the active area of the electrode to a structure that is wished to be preserved, for example the urethra. This facilitates preservation of the urethra to minimize post-procedural irritative symptoms such as dysuria, hematuria, and urinary urgency.

After the electrodes have been positioned, current is applied to create acidic and basic zones. Specifically, direct electrical current is applied to the electrodes. In some embodiments, the direct electrical current is applied simultaneously to all electrodes from isolated current sources having individually selectable polarity and charge delivery. The applied current creates an acidic zone around the anode and an alkaline or basic zone around the cathode. Generally, the treatment zone tends to follow, and not cross, a tissue plane. Accordingly, using DC ablation, treatment may be up to the tissue plane. The sizes of the necrotic zones are based on the amount of charge delivered to each electrode, where charge (coulombs) equals current (amperes) multiplied by time (seconds). In some embodiments, the applied current is at a relatively low level such as between approximately 1 mA and approximately 100 mA. Generally, treatment time increases as current decreases. Treatment time decreases as the number of electrodes increases. Treatment time may decrease if impedance decreases and the voltage compliance of the constant current system is low or the system utilizes constant voltage. In accordance with one embodiment, BPH treatment is achieved in approximately 30 minutes when using a 4, 6, 8, or 12 electrode array at 20 mA to deliver the treatment of 36 coulombs per electrode pair. Treatment time is reduced to 24 minutes when the current is increased to 25 mA and delivering 36 coulombs per electrode pair. The systems and methods disclosed herein employ slow, low current, low power treatment. Because of the plurality of electrodes and the substantially simultaneous treatment through all electrodes, total treatment time is nevertheless kept low. Table 6 shows the relationships between current, power, time, charge, and number of electrodes.

TABLE 6

| Current per Electrode Pair (mA) | Impedance per Electrode Pair (ohms) | Power per Electrode Pair (mW) | Time (minutes) | Charge per Electrode Pair (coulombs) | Number of Electrode Pairs | Total Charge (coulombs) |
|---|---|---|---|---|---|---|
| 10 | 400 | 40 | 30 | 18 | 1 | 18 |
| 10 | 700 | 70 | 30 | 18 | 2 | 36 |
| 10 | 1000 | 100 | 30 | 18 | 3 | 54 |
| 25 | 400 | 250 | 30 | 45 | 1 | 45 |
| 25 | 700 | 437.5 | 30 | 45 | 2 | 90 |
| 25 | 1000 | 625 | 30 | 45 | 3 | 135 |
| 50 | 400 | 1000 | 30 | 90 | 1 | 90 |
| 50 | 700 | 1750 | 30 | 90 | 2 | 180 |
| 50 | 1000 | 2500 | 30 | 90 | 3 | 270 |

The power applied to the electrodes is low compared to prior methods for treating BPH. More specifically, the power applied in accordance with systems and methods disclosed herein is on the order of milliwatts in the range of 20 to 3200 mW of power per electrode pair. The power typically used for each electrode pair is between approximately 190 mW (25 mA into a 300 ohm tissue impedance) to 1600 mW (40 mA into a 1000 ohm tissue impedance). A common impedance level seen in tissue is 400 ohms, and treating with 50 mA equates to a required power output of 1000 mW. This low power of treatment delivery allows for insignificant heat transfer to occur between the device and body tissues. This reduces or eliminates pain and discomfort from the heating of surrounding tissues during treatment that are experienced with thermal technologies utilizing significantly higher power. It also reduces or eliminates scarring and long healing times associated with a thermal wound. RF and microwave technologies using thermal energies to create necrosis in soft tissue often have power ranges between 15 and 75 W. The amount of power delivered by a thermal ablation system is not based directly on the measurement of the power delivered, but is based on the temperature measurement resulting from the power delivered. In contrast, the amount of charge delivered by the DC ablation system is based directly on the measurement of the charge delivered, allowing for more precise control of the size of the necrotic zones.

Figure 7:
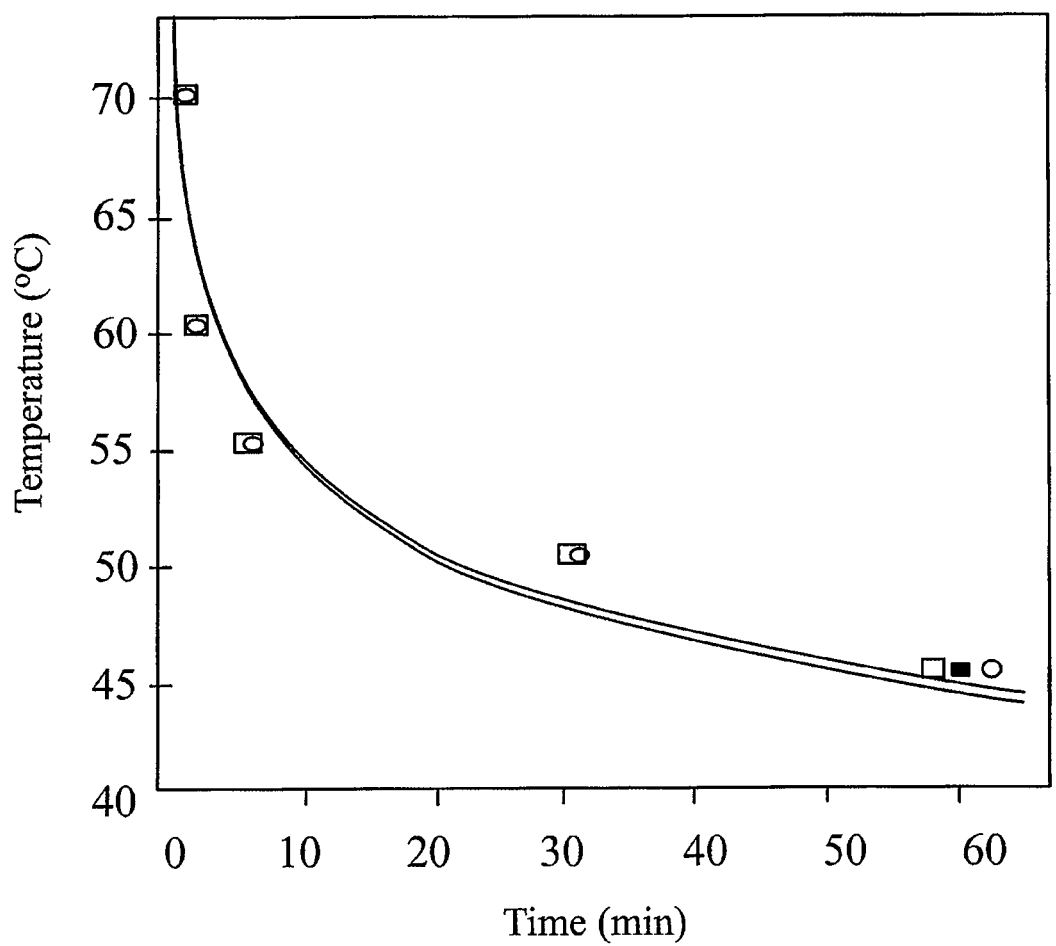
FIG. 7 illustrates a table showing time-temperature relationship for 90% normalized cell death in human BPH tissue from heating.

In order to create substantial cell death a temperature of at least 45 degrees C. or an 8 degree increase in tissue temperature must be maintained for approximately one hour. Substantial cell death occurs over 10 minutes at 55 degrees C. FIG. 7 illustrates the relationship between time and temperature. More specifically, FIG. 7 illustrates the time-temperature relationship for 90% normalized cell death in human BPH tissue from heating. At greater than 100 degrees C. the water present in the tissue boils and can cause impedance increases such that thermal therapy becomes intermittent. RF thermal ablation devices attempt to create tissue temperatures approaching 100 degrees C. to create necrosis with minimal treatment time. RF thermal ablation treatments can last between 1.5 and 5 minutes.

DC ablation applied with up to 50 mA only results in a maximum increase of 4 to 5 degrees C. in the tissues surrounding the electrodes. Lower currents will cause a lesser change in tissue temperature in the range of 0 to 3 degrees C. This mild increase in temperature does not create necrosis or act as a mechanism in ablating the tissue over the duration of the DC ablation treatment. These calculations are dependent on tissue type and vascularization of the tissue.

Inducing high localized temperatures causes surrounding tissues to also substantially increase in temperature. This may lead to collateral damage of structures outside of the intended treatment area such as, in the case of BPH treatment, the erectile nerves, rectum, or external sphincter. Devices that use radiated energy to heat tissues such as microwave require a rectal temperature probe to ensure that the rectum does not exceed an unsafe temperature. The high temperatures surrounding the treatment area also leads to a burning sensation in the pelvic region. Generally at 45 degrees a heat sensation is perceived. This is exceeded at the prostate capsule during thermal ablation treatments. A non-thermal DC ablation system, such as disclosed herein, does not have either of these concerns due to the low power that is delivered.

A single treatment can be done with no repositioning of the catheter and can be completed in no less than 8 minutes assuming delivering 24 C per electrode at the rate of 50 mA. A single treatment with no catheter repositioning can take as long as 100 minutes assuming delivering 60 C per electrode at a rate of 10 mA. It should be appreciated that, generally, no single treatment should last longer than 45 minutes for patient comfort and physician burden. Thus a treatment of 60 C should be completed at a minimal rate of 22 mA. If more treatment is required the catheter may be repositioned and a second treatment started.

In some embodiments, the electrodes may be generally cylindrical. The shape of the treatment zone for a cylindrical electrode is a cylinder with hemispheric ends and approximates an ellipsoid. By adjusting the electrode length and/or charge delivered, the shape of the ellipsoid can be controlled to make shapes that are cylindrical, oval, or spherical. As current is applied to the electrodes, an ellipsoid treatment zone forms around each electrode. The length of the ellipsoid is approximately equal to the length of the exposed electrode plus the diameter of the treatment zone. If the electrode length is significantly longer than the diameter of the treatment zone, the shape of the zone will be nearly cylindrical. The ends will be round (hemispheres) but the shape will be long and narrow like a cylinder. As the treatment continues, the diameter and length of the zone grow. As a percentage of the previous dimension, the diameter grows faster than the length. As this continues, the shape of the treatment zone becomes more oval than cylindrical and eventually becomes nearly spherical.

Figure 8A:
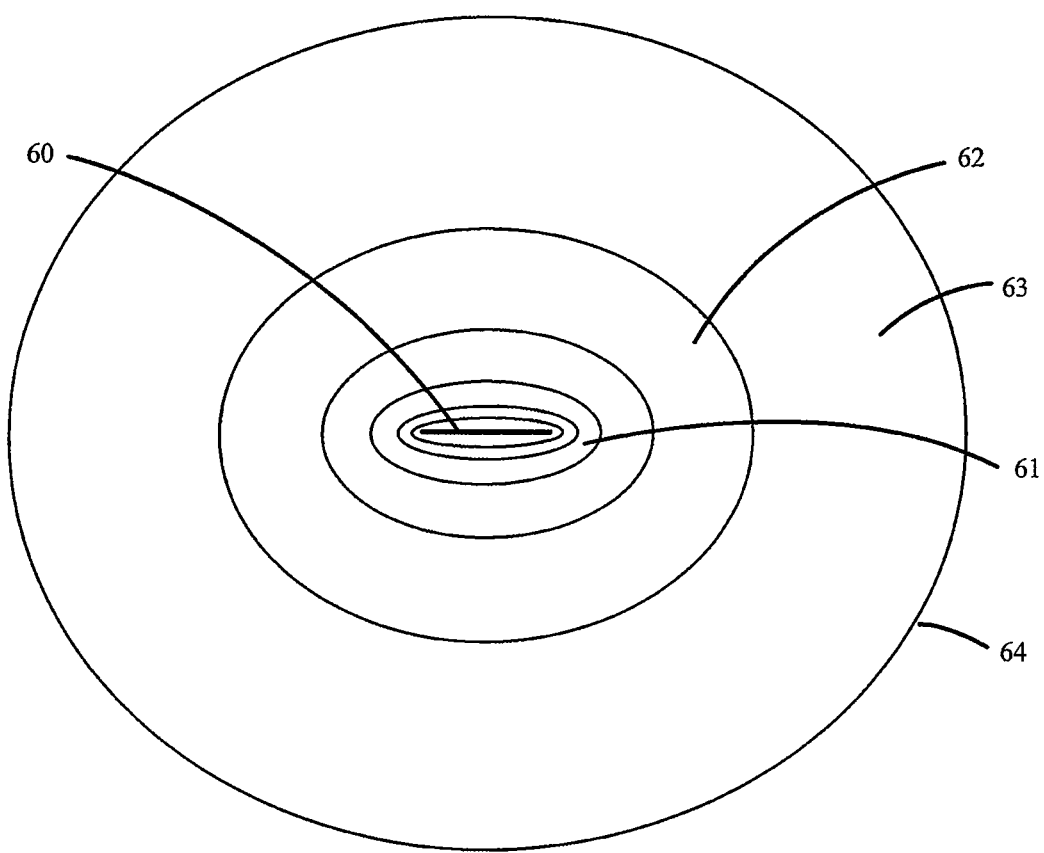
FIG. 8a illustrates changes to the shape of the treatment zone, in accordance with Various embodiments.

FIG. 8a illustrates a treatment zone around an electrode 60 wherein the treatment zone is, for the purposes of illustration, divided into 4 zones 61, 62, 63, and 64, extending radially outward from the electrode 60. As shown, the treatment zones 61, 62, 63, and 64 change shape as they extend away from the electrode 60. The zone 61 closest to the electrode is nearly cylindrical while the zone 64 farthest from the electrode is nearly spherical. Accordingly, with electrodes of equal length, treatment zone size as well as shape may vary with different applied currents when treating for an equal amount of time. Treatment shape will vary as well due to the proximity of tissue planes that impede the diffusion of the treatment.

Figure 8B:
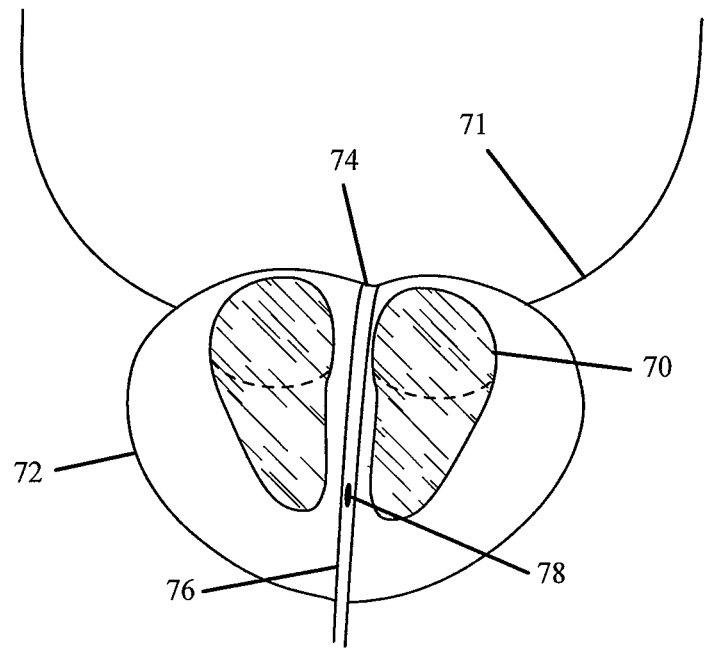
FIG. 8b illustrates coronal tracing of a treatment zone, in accordance with one embodiment.
Figure 8C:
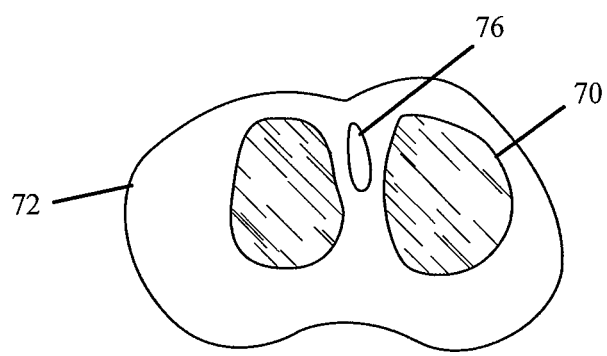
FIG. 8c illustrates transverse tracing of a treatment zone, in accordance with one embodiment.

FIGS. 8b and 8c illustrate a suitable area to create necrosis in the prostate to relieve symptomatic BPH. FIG. 8b illustrates coronal tracing of a treatment zone. FIG. 8c illustrates transverse tracing of a treatment zone. As shown, the treatment zones 70 may be in the lateral lobes 72 of the prostate adjacent to the bladder neck 74 and along the urethra 76 to the verumontanum 78. FIG. 8b also illustrates the bladder 71 for reference. Treating in the treatment zones 70 maximizes symptom relief obtained by treatment as the necrotic tissue is reabsorbed by the body and pressure is removed from the urethra. The urethral interaction of the treatment may be minimized to reduce transient irritative symptoms such as hematuria, dysuria, and urinary urgency. Amount of charge delivered, electrode shape and size, electrode array, electrode positioning, number of electrodes, current level, and electrode insertion length are all factors in treatment.

In another embodiment the electrodes may be staggered such that they do not align. In another embodiment 3, 5, 6, 7, 9, 10, 11, and 12 electrode arrays may be utilized to treat the prostate with DC ablation through the urethra and into the lateral lobes of the prostate. These embodiments are optimized to created treatment zones as prescribed in FIGS. 8b and 8c.

Figure 9A:
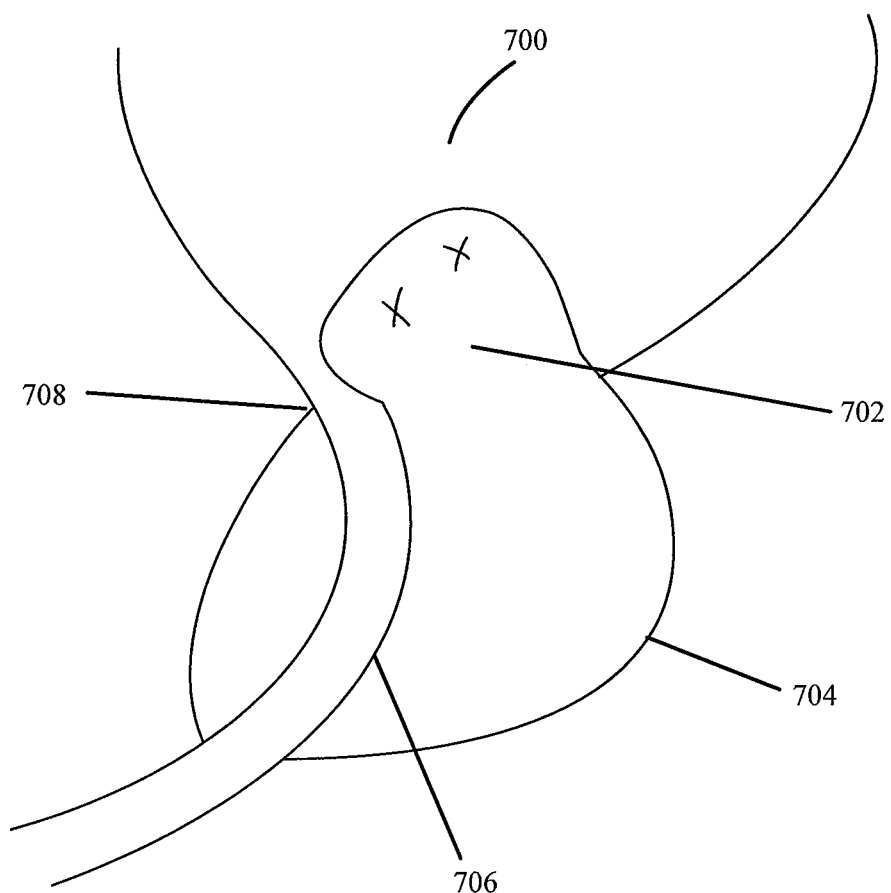
FIG. 9a illustrates a prostate anatomy with a large median lobe that extends up in the bladder.

In some patients it may be desirable to treat the median lobe of the prostate instead or in addition to the lateral lobes. FIGS. 9a-9d illustrate median lobe treatment. FIG. 9a shows a prostate anatomy 704 with a large median lobe 702 which extends up into the bladder 700. A large median lobe 702 can cause a urinary obstruction of the prostatic urethra 706 at the bladder neck 708. Ablating the median lobe can be accomplished using DC ablation by using a modified method and system for treating the lateral lobes as previously described.

Figure 9B:
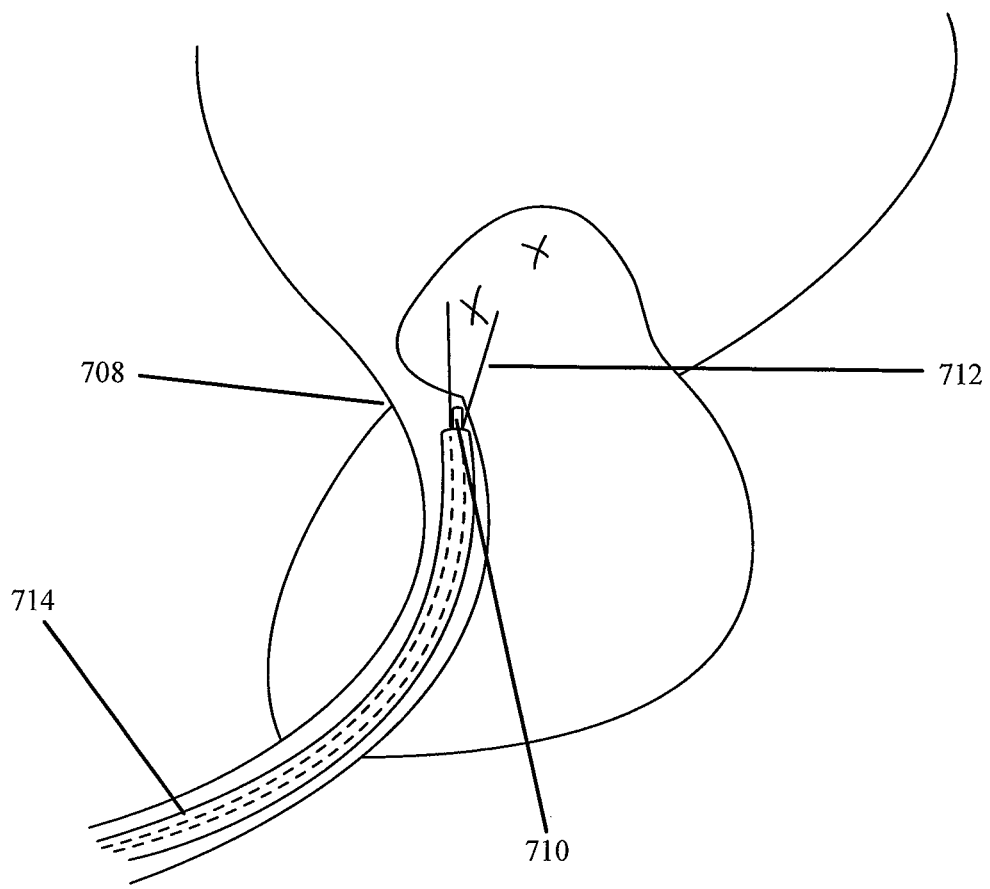
FIG. 9b illustrates positioning of a system for treatment of the median lobe, in accordance with one embodiment.
Figure 9C:
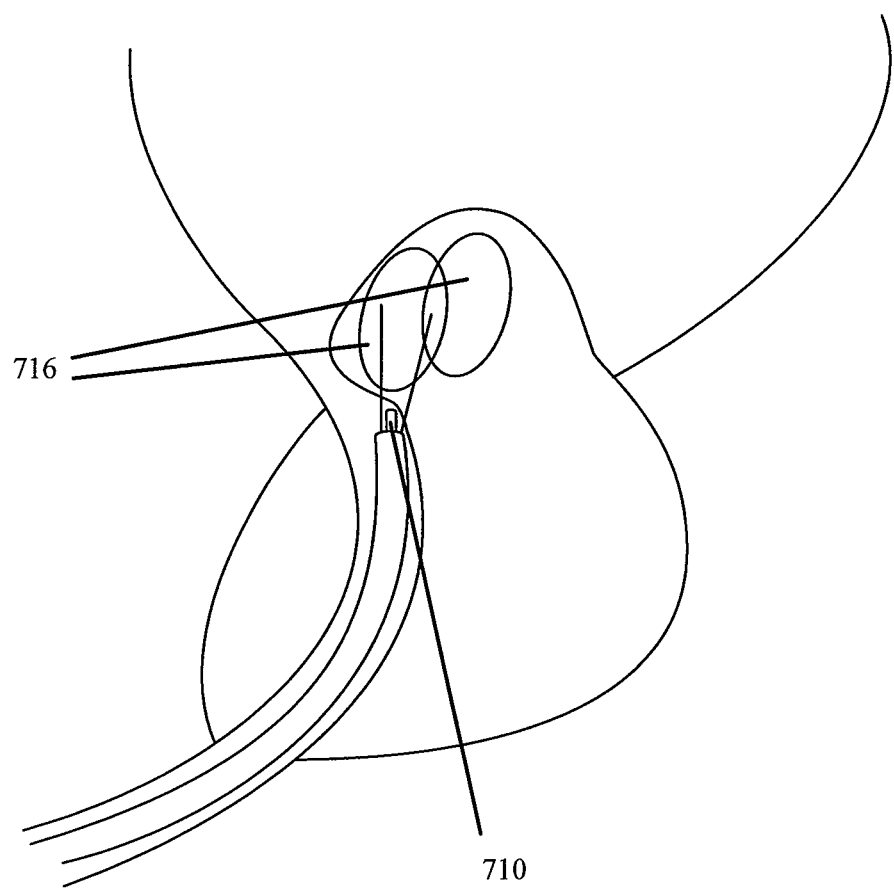
FIG. 9c illustrates treatment zones created through treatment of the median lobe, in accordance with one embodiment.

FIG. 9b illustrates positioning of a system for treatment of the median lobe. FIG. 9c illustrates treatment zones created through such treatment. Treating the median lobe of the prostate can be accomplished using methods described herein. As a preliminary matter, it may be useful to assess the size and position of the median lobe through visualization of the median lobe through Ultrasound, CT, MRI or cystoscopy. A transurethral delivery catheter 714 is routed in proximity to the bladder neck 708 and the area to treat identified by inserting a cystoscope 710 through or adjacent to the delivery catheter. A plurality of electrodes 712, for example between 2 and 4 electrodes, may then be extended into the median lobe under cystoscopy guidance. Insertion may be done either through the urethra near the bladder neck or from the bladder back into the median lobe. After the electrodes are placed a dose or charge of 15 to 60 coulombs per electrode may be delivered creating treatment zones 716 in the median lobe as shown in FIG. 9c. The catheter may be anchored to prevent the electrodes from moving during treatment. After treatment is completed the catheter and cystoscope is removed from the body.

Figure 9D:
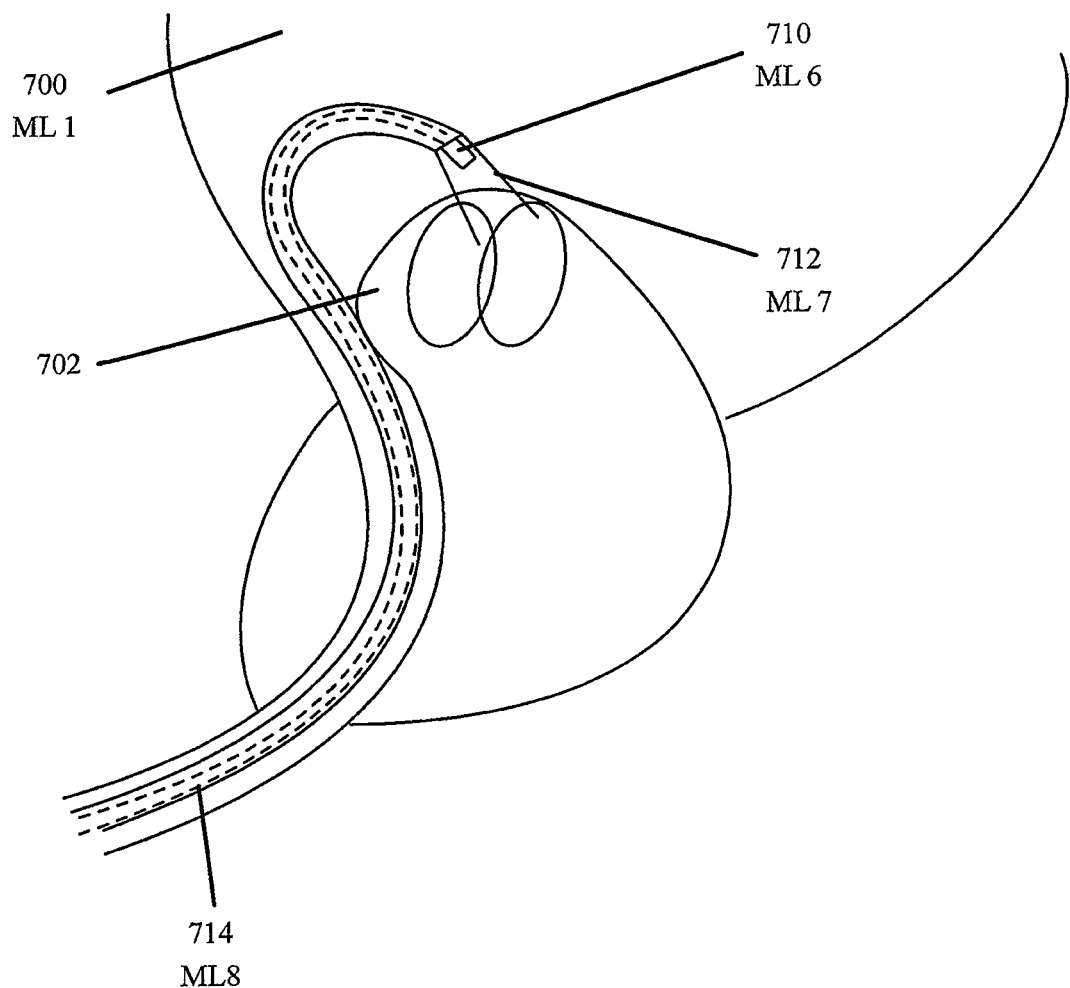
FIG. 9d illustrates an alternative treatment method for treating the median lobe, in accordance with one embodiment.

FIG. 9d illustrates an alternative treatment method for treating the median lobe. As shown, the delivery catheter 714 may be routed into the bladder 700 and then curved back towards the median lobe 702 where the electrodes may be inserted under guidance from a cystoscope.

As may be appreciated by those skilled in the art, similar systems and methods may be used for ablation of tissue in several different areas of the body. Such areas may include, for example, the trachea, stomach, esophagus, rectum, colon, intestine, bladder, uterus, and other tissues accessible from a lumen.

Figure 10A:
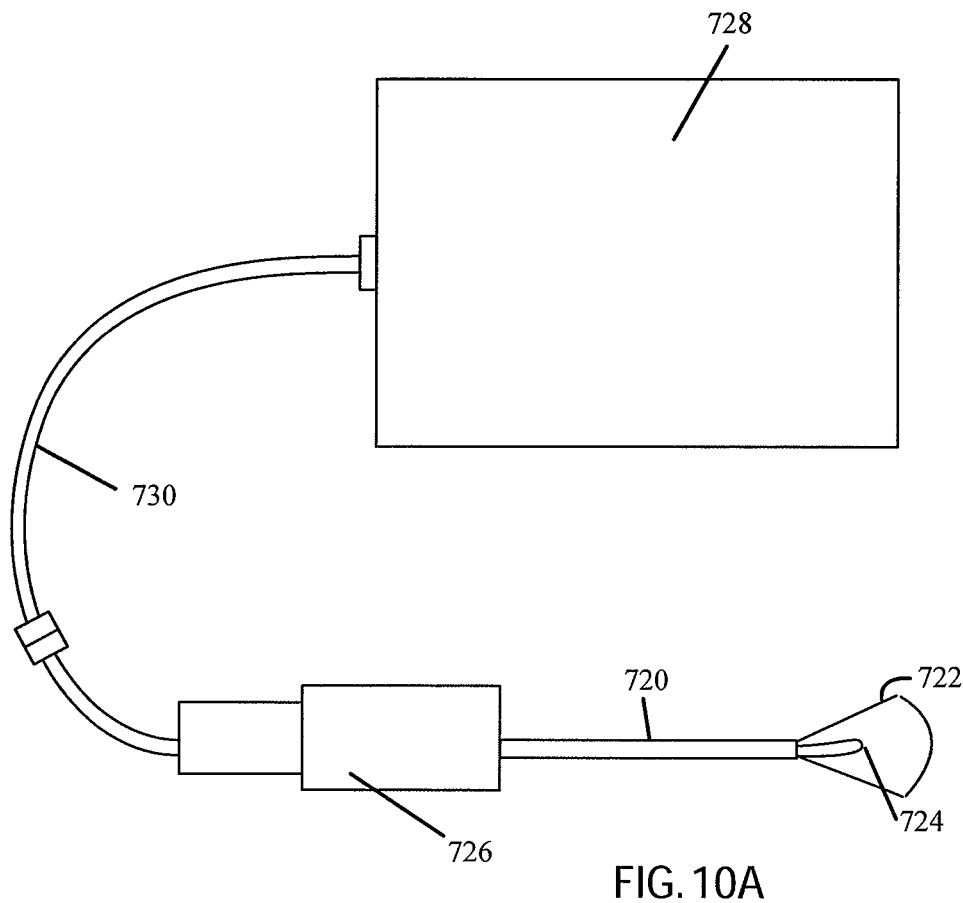
FIG. 10a illustrates a perspective view of a system for median lobe treatment, in accordance with one embodiment.
Figure 10B:
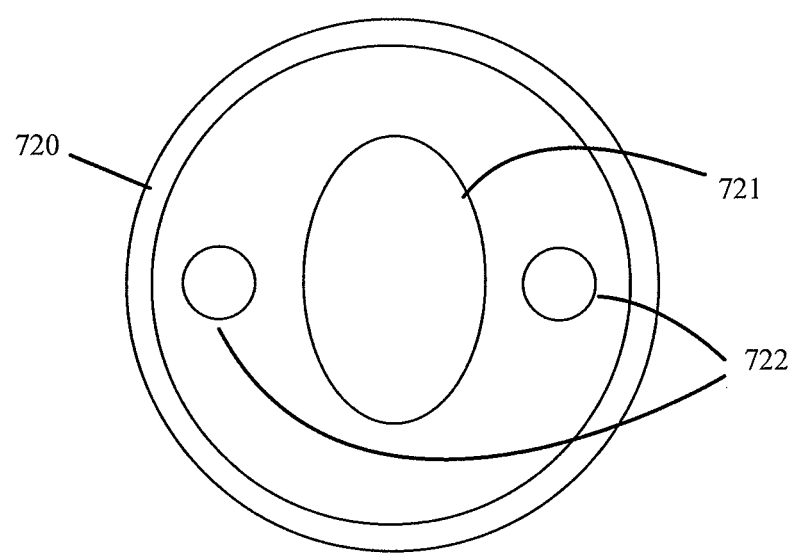

FIGS. 10a and 10b illustrate a specific embodiment of the delivery catheter for a system for treating the median lobe. FIG. 10a illustrates a perspective view and FIG. 10b illustrates an end view. As shown, the system may include a semi-flexible catheter 720 and a plurality of electrodes 722 positioned for extension from the distal tip of the catheter. In some embodiments, between 2 and 4 electrodes may be provided. A cystoscope 724 may be routed down the center of an open lumen 721 of the delivery catheter. The electrodes 722 may be actuated by a mechanism 726 which remains outside of the body during treatment. The delivery catheter is connected to a generator 728 by an extension cable 730. The same generator can be used in the median lobe system as the system for treating the lateral lobes previously described.

In some embodiments, the gas generation and diffusion through tissue can be used to mark the necrotic region. By calibrating current and time to tissue type, the treatment zone (or area of necrosis) can be visualized on ultrasound. As discussed, the gas created during DC ablation diffuses through tissue being treated until it becomes absorbed in solution with the fluids present in the tissue. By controlling the rate of therapy (current) and the total therapy delivered, the region of gas bubbles in the tissue can be correlated to the area of necrosis. Such visualization may be used, for example, when DC ablation is used to treat benign and malignant tumors.

In some embodiments, one anode and one cathode are provided per current source. This may facilitate control of the treatment zone size. In other embodiments, more than one anode and one cathode are provided per current source. This may reduce the likelihood of poor tissue contact during treatment. If more than 2 electrodes are used per current source, current may be directed to specific electrodes of the same polarity by making some electrodes have higher (or lower) impedance than others. This may be accomplished by varying configurations of the electrodes, for example by creating different surface textures on different electrodes, by providing a means for venting gases via some electrodes but not others, etc.

In various embodiments, size of treatment zone may be customized for specific treatment positions of the electrodes. For example, in treatment of BPH, smaller treatment zones may be formed near the prostate base and apex and larger zones may be formed in bulkier areas. Such varied treatment zone sizes may be provided by using different electrode sizes, differing numbers of electrodes, differing current or charge delivery, or by varying other process or system parameters. For example, shorter electrodes may be used at the distal and proximal ends and longer electrodes may be used in the middle band(s), as shown in the embodiment of FIG. 4c. In an alternative embodiment, fewer electrodes can be used at distal and proximal ends and more electrodes in the middle band(s). In a further embodiment, less charge may be delivered to electrodes at distal and proximal ends and more charge may be delivered to electrodes in middle band(s). In yet a further embodiment, the electrodes at distal and proximal ends may be programmed as anodes and those in the middle band(s) as cathodes.

DC current ablates tissue by imparting extreme pH (<5 or >9 to 10) into the tissue surrounding the electrode. The area surrounding the electrode affected by the extreme pH is referred to as the treatment zone. In some embodiments, the system may be deployed to provide overlapping polarity treatment zones. Such overlapping may optimize the radius of the treatment zone for tissue ablation. When DC ablation electrodes are placed in close proximity, the extreme pH zones grow. When they overlap for a paired electrode, the zones increase in radius more readily than when separate for a given dose.

Figure 11:
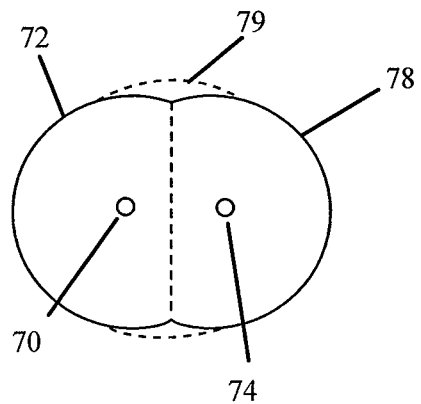
FIG. 11 illustrates overlapping treatment zones, in accordance with one embodiment.

FIG. 11 illustrates a radius of a combined treatment zone at the pH interface. The treatment zone may increase approximately 10-20% in radius. Specifically, FIG. 11 illustrates a first electrode 70 with a first pH extreme 72, a second electrode 74 with a second pH extreme 76, and a typical treatment radius 78. FIG. 11 further illustrates the increased radius 79 of the combined treatment zone (shown by the dotted line).

Similarly, in other embodiments, the anode and cathode may be placed proximate one another. By placing the anode and cathode (opposite polarity electrodes) in close proximity to one another, extreme pHs can be achieved to necrose tissue. The opposite pH levels help to neutralize one another to decrease the amount of time it takes for the surrounding tissue to return to normal conditions.

Figure 12:
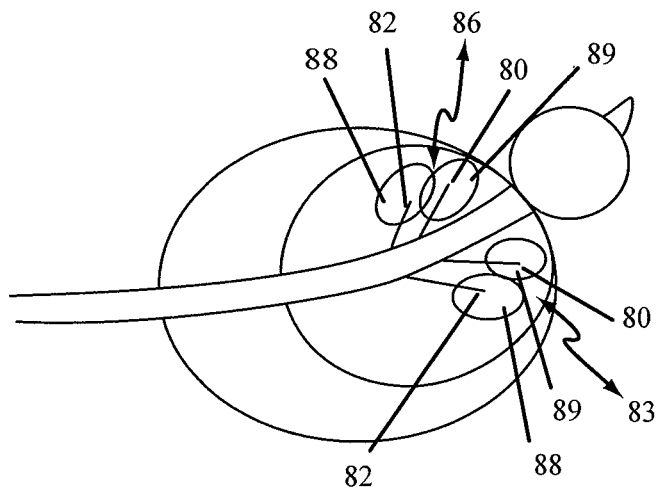
FIG. 12 illustrates electrodes placed in close proximity, in accordance with one embodiment.

FIG. 12 illustrates an embodiment with two anodes 80 and two cathodes 82. In one treatment area 83, an anode 80 is placed proximate a cathode 82, for example spaced between approximately 2 and approximately 20 mm from one another. The same set up is provided in a second treatment area 86—an anode 80 placed proximate a cathode 82. As a result, in each treatment area 83 and 86, a high pH zone 88 and a low pH zone 89 each arise proximate to the other. The zones 88 and 89 likely overlap one another. In the area of zone overlap, the pH of the tissue can return to normal within, for example, hours of the DC ablation procedure.

Figure 13A:
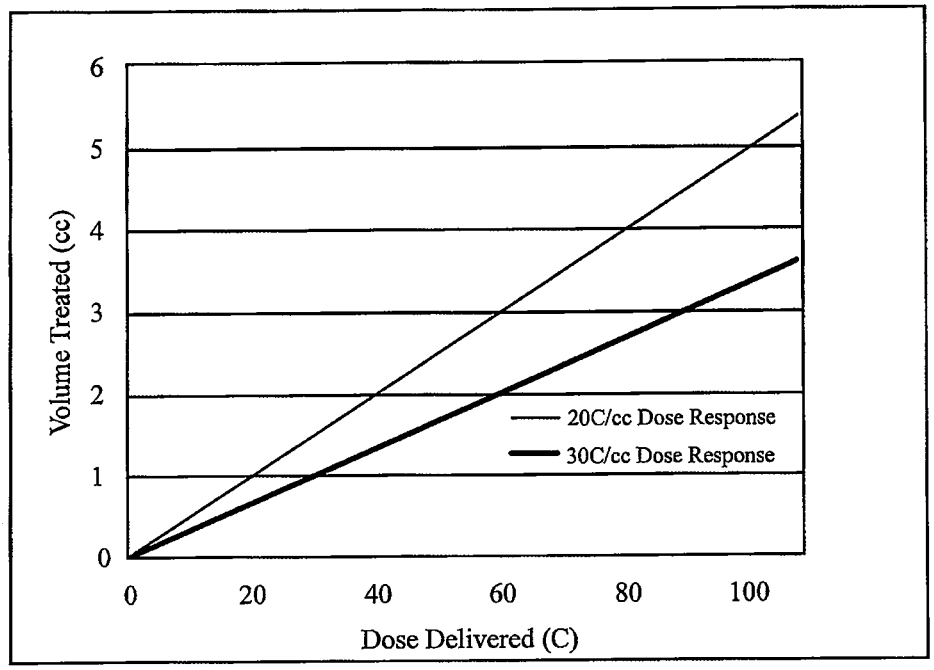
FIG. 13a illustrates dose delivered versus volume of tissue treated, in accordance with one embodiment.
Figure 13B:
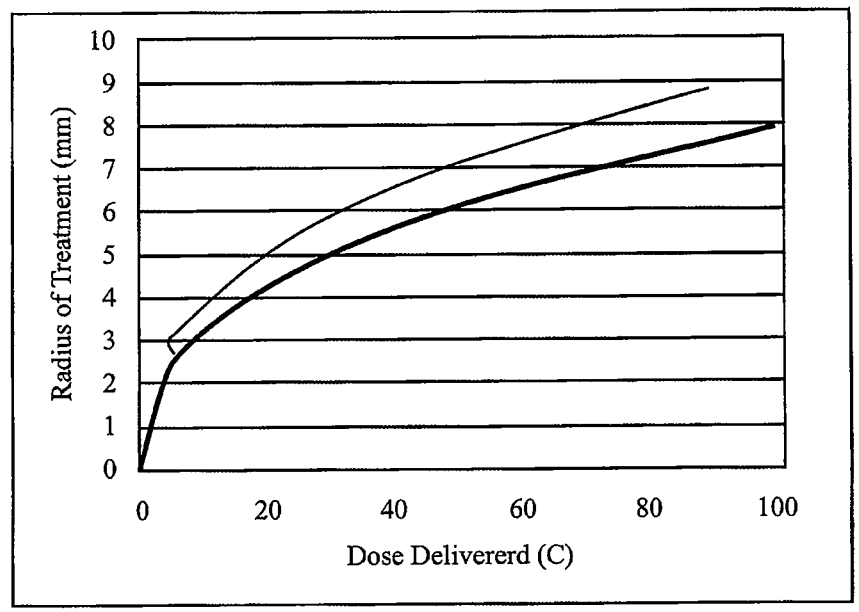
FIG. 13b illustrates dose delivered versus expected radius of treatment for a 6 mm electrode in prostatic tissue, in accordance with one embodiment.
Figure 13C:
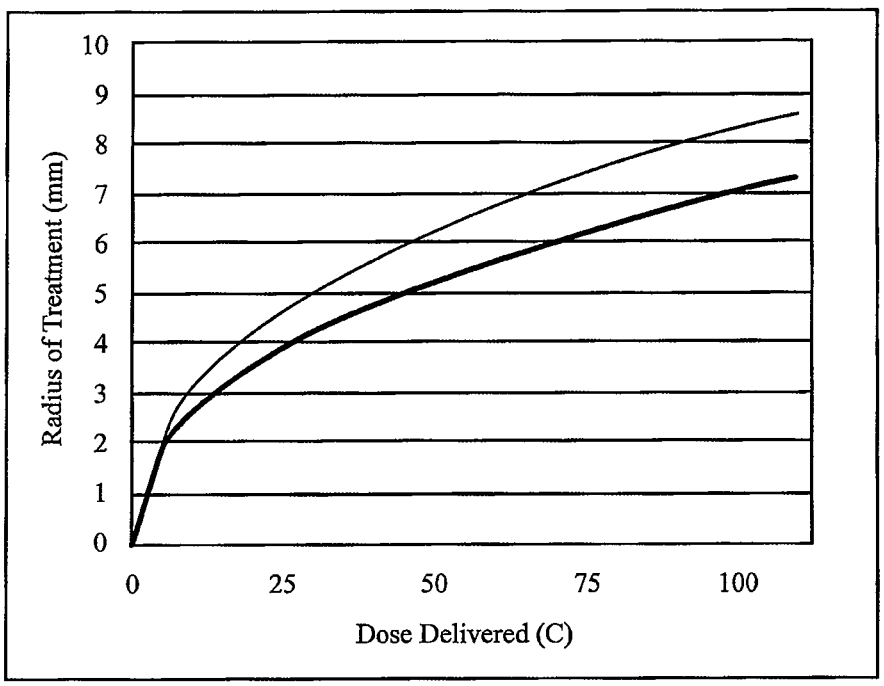
FIG. 13c illustrates dose delivered versus expected radius of treatment for 12 mm electrode in prostatic tissue, in accordance with one embodiment.
Figure 13D:
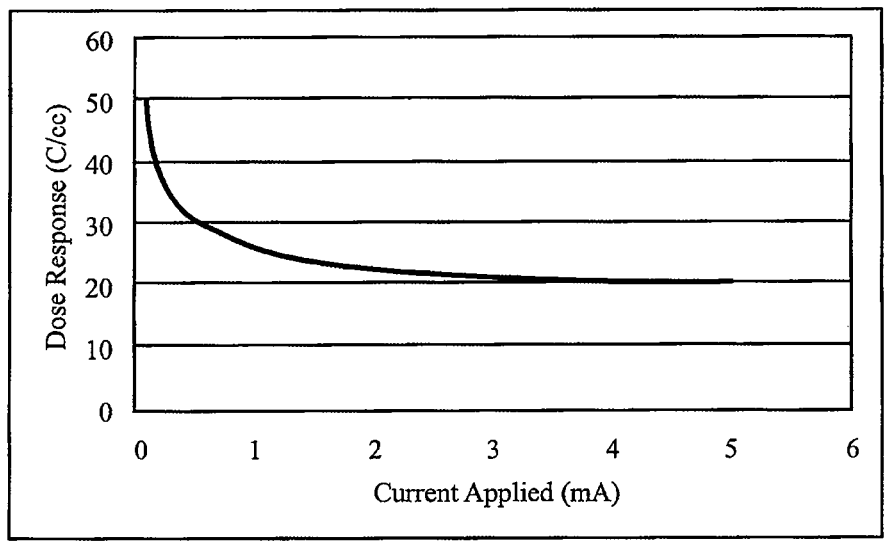
FIG. 13d illustrates current applied versus dose response, in accordance with one embodiment.

FIGS. 13a through 13d illustrate various effects and relationships of dosage. FIG. 13a illustrates the dose delivered versus the volume of tissue treated. FIG. 13b illustrates the dose delivered versus the upper and lower limit of expected radius of treatment for a 6 mm electrode in prostatic tissue. FIG. 13c illustrates the dose delivered versus the upper and lower limit of expected radius of treatment for a 12 mm electrode in prostatic tissue. FIG. 13d illustrates current applied versus dose response.

Generally, DC ablation creates necrosis around a singular anode and a singular cathode at a rate of approximately 0.07-0.05 cc/C at the anode and at a rate of approximately 0.10-0.08 cc/C at the cathode. A typical period for treating BPH using systems and methods for DC ablation as disclosed herein is under 30 minutes. Dosing at approximately 25 mA for approximately 30 minutes will deliver 45 C. This in turn treats between approximately 5.8 cc and approximately 7.7 cc of tissue per pair of electrodes. To achieve a more efficacious treatment, multiple electrode pairs may be used. In some embodiments, 2 to 6 pairs of electrodes may be used. This correlates to approximately 11.6 to approximately 14.4 cc of treated tissue for 2 pairs of electrodes and between approximately 34.8 and approximately 43.3 cc of treated tissue for 6 pairs of electrodes. These numbers do not account for the overlap of treatment zones which decrease the amount of treated tissue. In some embodiments, the treatment zones overlap. Treatment times may vary between 15 and 45 minutes depending on the dosing required and rate at which the treatment is delivered. Alternatively fewer pairs of electrodes could be used in a device to achieve these same larger treatment zones if the catheter or electrodes are repositioned between treatments.

The rate at which the charge is applied (current, units of milliamperes) does not affect the ultimate radius of the treatment zone as long as the current provides more charge than the tissue's natural ability to stabilize its own pH. The relationship between current applied and the dose response is shown FIG. 13d. As shown, in some embodiments, it may be desirable for the treatment current to be at or above approximately 1 mA. In the example of FIG. 13d, all currents above 5 mA exhibit generally the same dose response. While higher currents may not increase dose response, higher currents may reduce treatment time to deliver the desired dosage. The higher current, however, may increase likelihood of patient discomfort. Generally, as current decreases, patient discomfort and muscle contractions (or muscle twitch) decrease. In some embodiments, the dose may be delivered at a constant current to prevent nerves in the region of treatment from being stimulated and causing muscle contraction. The magnitude of current delivered may be adjusted during treatment to allow pain and treatment time to be minimized. Care should be taken however, because a fast rate of current change may cause patient discomfort and muscle twitch. Thus, in some embodiments, it may be advisable that any change in the current delivered be done at a rate no greater than 10 mA/s to prevent muscle contraction and patient discomfort. A suitable rate of change is approximately 1 mA/s.

Figure 14:
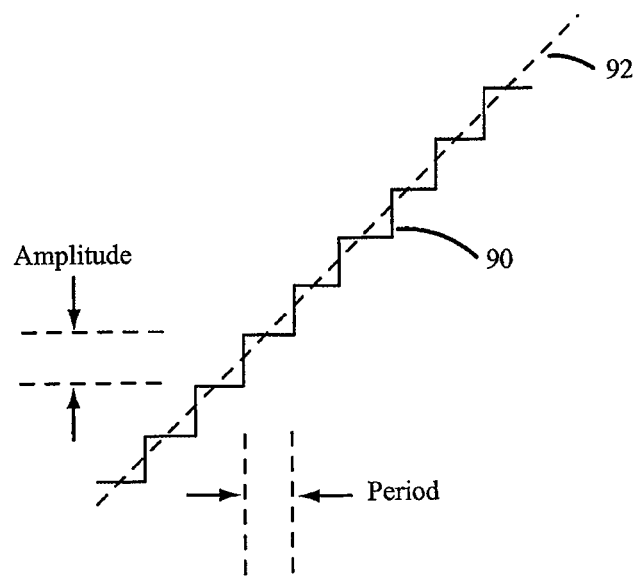
FIG. 14 illustrates and defines the period and amplitude of current ramping during the start of treatment, in accordance with one embodiment.

FIG. 14 illustrates current 90 increased gradually when current delivery is started to prevent the stimulation of nerves. Current 90 is also decreased gradually when current delivery is terminated. The increase or decrease may occur in steps of amplitude and period with the ramp rate equal to the step amplitude divided by the step period. The upper limit on the amplitude for preventing nerve stimulation is 0.5 mA for increasing current. A suitable embodiment is approximately 0.2 mA for increasing the current. The upper limit on the amplitude for preventing nerve stimulation is 1 mA for decreasing current. A suitable embodiment is approximately 0.5 mA for decreasing the current. Regardless of the slowness of the period of the steps, a large enough amplitude step will cause nerve stimulation. For amplitudes below that limit, there is a minimum limit on the period for preventing nerve stimulation. Small amplitude steps can still cause nerve stimulation if the steps occur too quickly and result in a ramp rate greater than 10 mA/s. The ramp rate (slope of broken line 92) should ideally be as great as possible without resulting in a high risk of nerve stimulation. If the step amplitudes are low enough, capacitance in the circuit may cause the output to look less like steps and more like a straight line (such as broken line 92), which may help to reduce the risk of nerve stimulation. These observations also apply to ramping down the current.

In some embodiments, an independent current source may be used to deliver the current for each electrode pair in order to control the charge passing through each electrode and thus the size of the treatment zone. Changing impedances at individual electrodes throughout the therapy session may lead to an unpredictable imbalance in treatment zones if multiple cathodes and anodes are put on a single current source. If multiple electrode pairs are placed on a single current source, the treatment zones may be controlled by putting a coulomb counter on each electrode and directing the desired amount of charge to each electrode.

The acidic and basic zones are created by the following chemical reaction:

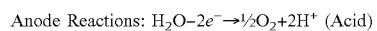

Anode Reactions: $H_2O - 2e^- \rightarrow \frac{1}{2}O_2 + 2H^+$ (Acid)

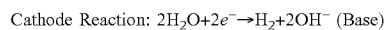

Cathode Reaction: $2H_2O + 2e^- \rightarrow H_2 + 2OH^-$ (Base)

The anode reactions also include a chlorine reaction that produces molecular chlorine. The molecular chlorine reacts with water to form hypochlorous acid, chloride and hydrogen ions. These reactions occur within both benign and malignant tissue including prostate. A marker, such as an ultrasound marker, may be provided to indicate pH in real time during treatment.

The anode and cathode reactions create cell necrosis within the treatment zone. The cathode causes necrosis via a combination of liquefaction cell necrosis and coagulation cell necrosis. The anode causes necrosis via coagulation cell necrosis. Cell necrosis occurs in normal prostate tissue, hyperplastic prostate tissue, and malignant prostate tissue. Accordingly, dosage and configuration may be optimized to generally limit the treatment area to the hyperplastic prostate tissue.

Figure 15A:
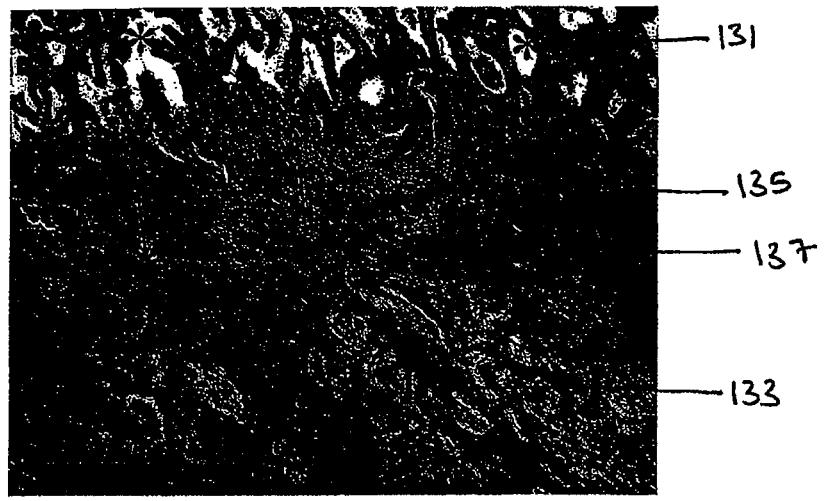
FIG. 15a is an in vivo image illustrating a liquefaction necrosis histology at the boundary of a cathode treatment zone.
Figure 15B:
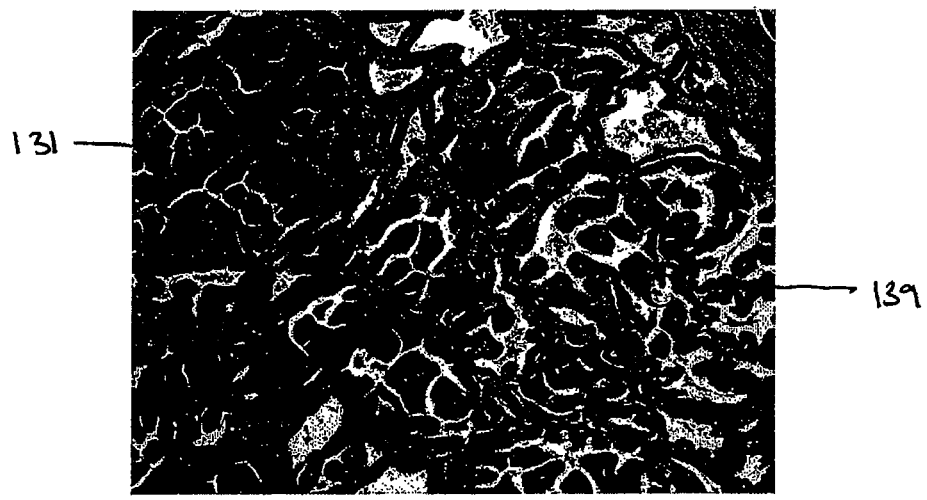
FIG. 15b is an in vivo image illustrating a coagulation necrosis histology at the boundary of an anode treatment zone.

FIGS. 15a and 15b illustrate images of necrosis within necrotic prostate tissue caused by DC ablation at a cathode and an anode. FIG. 15a illustrates liquefaction necrosis histology at the boundary of a cathode treatment zone. Normal tissue is shown at 131 and liquefaction necrosis is shown at 133. As shown, a transition zone exists at 135 with a liquefaction necrosis boundary 137 being formed. FIG. 15b illustrates coagulation necrosis histology at the boundary of an anode treatment zone. Specifically, normal tissue is shown at 131 and coagulation necrosis is shown at 139.

Liquefaction necrosis and coagulation necrosis create a change in the structure in the prostate as the affected tissues become fibrous and are absorbed into the body through its natural healing process. This thus causes removal of cellular mass, leaving a void. Because the treatment zone is predictable, the void is predictable. By removing cellular mass within the prostate, the interior of the prostate is debulked and excess pressure placed on the prostatic urethra is reduced. This reduction in pressure on the urethra reduces or eliminates BPH symptoms, sometimes referred to as Lower Urinary Tract Symptoms (LUTS). It is an advantage of DC ablation over other techniques that the outer wall of the prostate is more resistant to damage caused by the electrochemical reaction than is inner prostate tissue. Hence, a set of electrodes not perforating the outer wall but close to the wall destroys the desired prostate tissue inside the boundary formed by the wall and not the wall itself. The outer boundary generally appears to be more chemically robust as well as providing a mechanical boundary. Thus, while thermal energy does not respect the tissue plane, DC ablation does.

In some embodiments, the electrodes may be withdrawn, the catheter repositioned, and the electrodes redeployed to cover the desired treatment zones. In other embodiments, the number of electrodes provided is sufficient to provide treatment without redeployment of the system.

Once the reactions leading to cell necrosis have begun, the electrodes may be withdrawn and the catheter is withdrawn. In some embodiments, the electrodes are withdrawn into the catheter and the catheter is withdrawn. Withdrawing the electrodes into the catheter may comprise release of a trigger or slide in the handle, may comprise collapsing the electrodes by sliding a sheath over the electrodes, or may be done in other suitable manner. In some embodiments, the electrodes and the catheter are withdrawn simultaneously.

The liquefaction and softening of treated tissue around the cathode results at least from elevated pH; elevated pH causes necrosis and cell lysis. Rupture of the cell wall causes the rigid pathologic tissue to soften, relieving symptoms of BPH related to excess compression of the urethra. This effect can be employed to advantage in the removal of electrodes. Changing the polarization of each electrode to cathodic at some time during treatment will soften the area and allow easier removal of the electrode. Likewise, inserting the electrodes may be eased by making each one cathodic during the insertion. If tenting of the urethra is evident during insertion, causing each electrode to be cathodic at that time can soften the urethra at the electrode tip sufficiently to allow easier penetration without significant additional damage to the urethra.

For example, with some physiologies it may be difficult to penetrate lumens, such as the urethra, and tissue with a fine electrode. Chemical drilling may be used to aid in tissue penetration. More specifically, DC ablation may be used to help penetrate the tissue. In some embodiments, all of the electrodes may be negative or cathodic to aid in tissue penetration. This takes advantage of the inherent electro-osmosis of DC ablation where fluids are drawn to the cathodes and the tissue becomes edemic. The gelatinous tissue so treated is more easily penetrated. Thus, in some embodiments, the electrode may be activated when first contacted with the tissue but before advancement into the tissue. The electrodes may be advanced during pre-treatment or pre-treatment may be done for a short period of time, for example approximately 30 seconds, and the electrodes then advanced.

Figure 16:
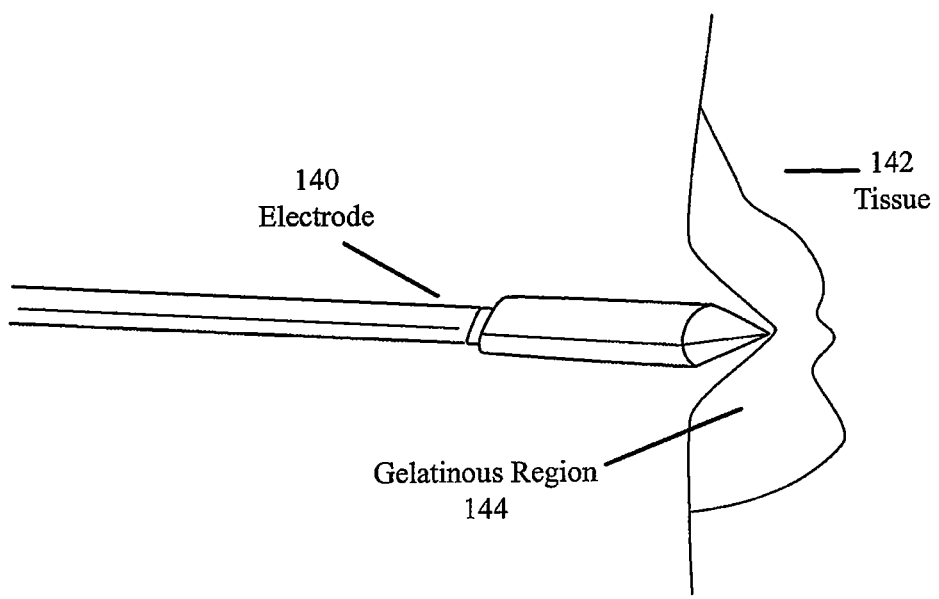
FIG. 16 illustrates a view of electrode deployment into pretreated tissue.

FIG. 16 illustrates a view of electrode deployment into pretreated tissue. As shown, the tissue 142 includes a pretreated region 144 that is substantially gelatinous. The electrode 140 is able to more easily penetrate the tissue 142 in the gelatinous region 144.

Figure 17A:
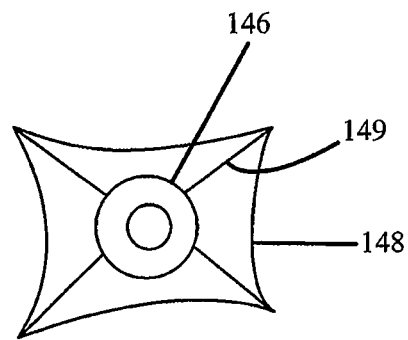
FIG. 17a illustrates a system for tissue treatment including a catheter and electrodes with the electrodes deployed without vacuum, in accordance with one embodiment.
Figure 17B:
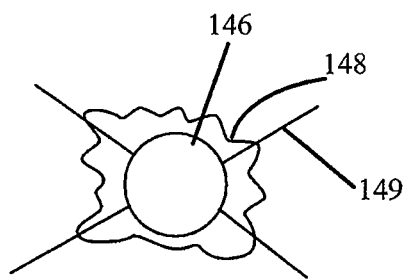
FIG. 17b illustrates a system for tissue treatment including a catheter and electrodes with the electrodes deployed with vacuum, in accordance with one embodiment.

FIGS. 17a and 17b illustrate a further embodiment to facilitate electrode penetration. In another embodiment of urethral preparation, a vacuum may be used to put the urethra in direct and firm contact with the catheter of a system for treating tissue as provided herein. Direct and firm contact of the urethra with the catheter facilitates piercing of the urethra by electrodes. With some physiologies, the urethra may have a larger cross section than the catheter placed therein. This increases column strength requirements for the catheter and makes it more difficult for the electrodes to pierce the catheter. For example, the urethra may expand and not be penetrated by the electrodes or the electrodes may buckle against the urethra. FIGS. 17a and 17b illustrate a system for tissue treatment including a catheter 146 and electrodes 149. The figures illustrate an end view with the system deployed through the urethra 148. FIG. 17a illustrates electrodes 149 deployed (without vacuum) and causing expansion of the urethra 148. As shown in FIG. 17b, by drawing the urethra 148 firmly against the catheter 146, for example by vacuum force, the electrodes 149 more easily penetrate the urethra 148. Thus, the electrodes 149 may be deployed relatively immediately after drawing of the urethra 148 against the catheter 146. FIG. 17b illustrates electrodes 149 penetrating the urethra 148, with the urethra 148 vacuumed to the catheter 146.

Figure 18:
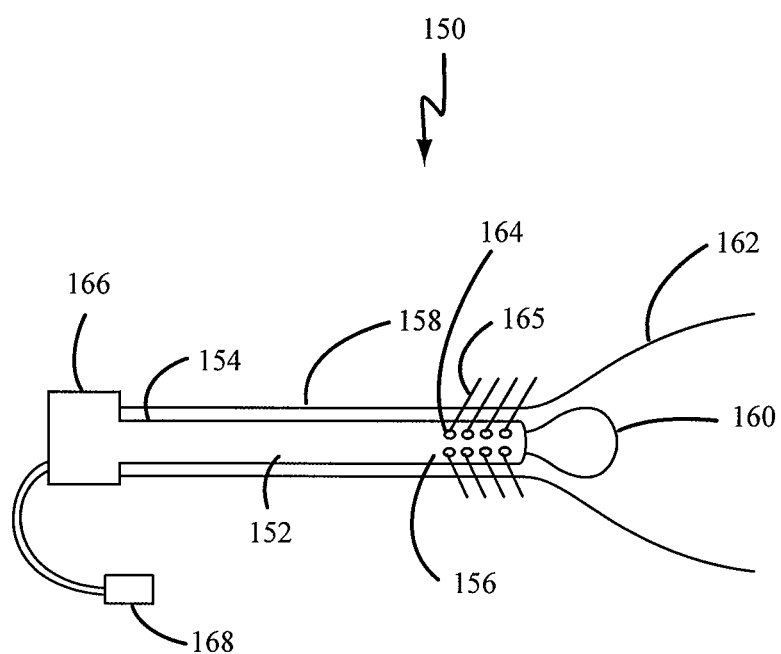
FIG. 18 illustrates an embodiment of a system for treating tissue including vacuum ports at the electrode holes, in accordance with one embodiment.

FIG. 18 illustrates an embodiment of a system for treating tissue including vacuum ports at the electrode holes. As shown, the system 150 includes a catheter 152 having a proximal end 154 and a distal end 156. As shown, the catheter 152 is configured to extend through the urethra 158. A balloon or other fixation element 160 is provided at the distal end 156 of the catheter 152 and is shown deployed in the bladder 162. A plurality of electrode holes 164 are provided at a distal portion, near the distal end 156, of the catheter 152. The electrode holes 164 operate for facilitating deployment of electrodes 165 from the catheter 152 and also operate as vacuum ports. A vacuum connector 166 and an electrical connector 168 are provided at the proximal end 154 of the catheter 152. The vacuum connector 166 may couple to a syringe or other means for achieving a vacuum. Drawing a vacuum before electrode penetration may facilitate use of smaller electrodes. In some embodiments, the system shown in FIG. 18 may be used for saline injection and vacuum. More specifically, the electrode holes/vacuum ports may be used to create a vacuum and also to distribute saline. Thus, in one embodiment, vacuum is achieved during penetration of the electrodes and is followed by saline injection for buffering during treatment.

As can be appreciated from the chemical reactions occurring at the electrodes, gases may be generated by DC ablation. More specifically, during DC ablation of soft tissue, ions are created at the anode and cathode electrodes when current passes through the electrodes. In order for the current to pass, the impedance generally is stable and less than about 5 kΩ to prevent operating at high voltages. DC ablation creates hydrogen and oxygen gas during the hydrolysis process. These gases can cause the impedance from the electrode to the tissue to spike greater than about 5 kΩ. This happens when the gas is allowed to build up around the electrode without either diffusing into the tissue, being vented away from the treatment area, or going into solution in fluid around the treatment zone. Typical impedance ranges within the prostate are between approximately 300 and 500 ohms when treating with a current of greater than approximately 5 mA.

The amount of current delivered affects the amount of gas created. The rate at which gas is created is directly proportional to the current at which it is delivered. For soft tissue applications such as the prostate, DC ablation generally may be delivered between approximately 10 mA and approximately 50 mA. Generally, at currents higher than 50 mA, gas created by the treatment may not have sufficient time to dissolve, diffuse, or vent. 75 to 100 mA may be used to decrease treatment time if gas is able to sufficiently vent. Conversely, at currents lower than 10 mA, the body's buffering may reduce effectiveness of the treatment. In one embodiment, current level is between approximately 25 mA and 40 mA.

Generally, the amount of gas generated by treatment is determined by dosing. The amount of gas generated typically increases as current increases. In various embodiments, the system may be provided with mechanisms for venting the gases generated. Means for venting the gases may be provided within the electrodes, within the catheter, or other. Accordingly, the method for BPH treatment may further comprise venting gases created during treatment. Removal of the gases may lower the impedance and impedance fluctuations seen by the electrodes, thereby permitting continued treatment in the desired range of current and voltage.

Figure 19A:
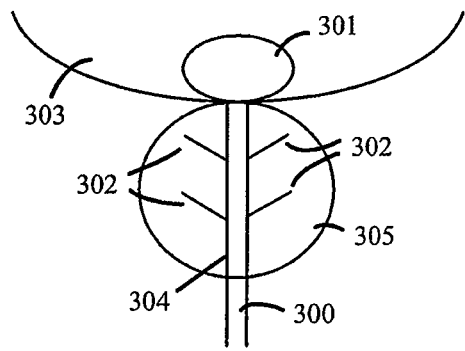
FIG. 19a illustrates balloon deployment in a bladder, in accordance with one embodiment.
Figure 19B:
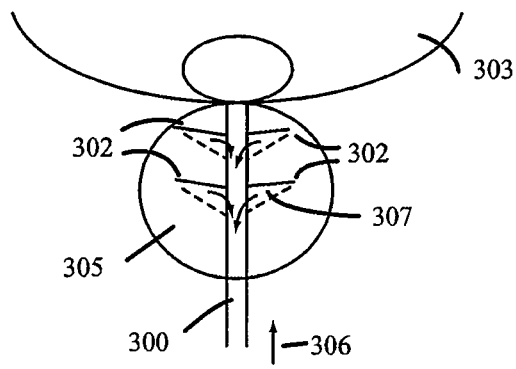
FIG. 19b illustrates catheter deployment while applying force towards a bladder, in accordance with one embodiment.
Figure 19C:
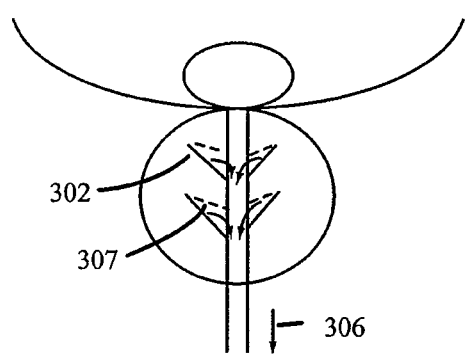
FIG. 19c illustrates catheter deployment while applying force away from the bladder in accordance with one embodiment.

A first embodiment of a mechanism for venting gases is shown in FIGS. 19a-19c. FIGS. 19a-19c illustrate relevant anatomy to BPH treatment including the bladder 303, urethra 304, and prostate 305. FIGS. 19a-19c further illustrate a catheter 300, balloon 301, electrodes 302, and gaps 307. As shown in FIG. 19a, the balloon 301 is located in the bladder 303 and inflated. The electrodes 302, having punctured the urethra 304, reside within prostate 305 either prior to or after applying current for DC ablation. In FIG. 19b, the catheter 300 has been pushed forward with force 306 towards the bladder 303 prior to applying current but after deploying electrodes 302. Force 306 holds the electrodes 302 in the position shown in FIG. 19b. This creates gaps 307 in the prostate 305 between the original electrode position of FIG. 19a and the new position of FIG. 19b. The gaps 307 serve to provide a path for the gases generated during DC ablation to escape. In an alternative embodiment, shown in FIG. 19c, the catheter 300 may be pulled away from the bladder 303 after deploying the electrodes 302.

Figure 20A:
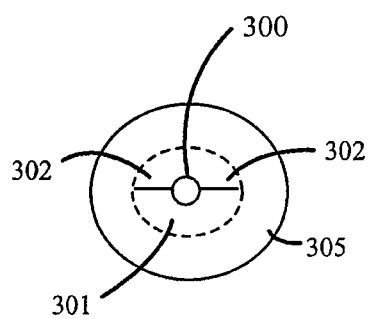
FIG. 20a illustrates electrode deployment in a prostate, in accordance with one embodiment.
Figure 20B:
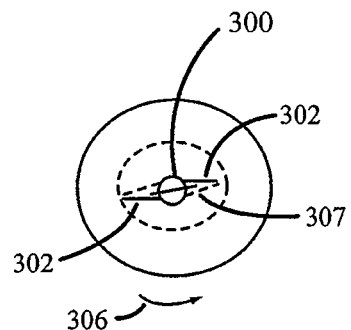
FIG. 20b illustrates catheter rotation for movement of electrodes, in accordance with one embodiment.

A second embodiment of a mechanism for venting gas is shown in FIGS. 20a and 20b. In yet another embodiment, the electrodes 302 may be rotated following deployment, as shown in FIGS. 20a and 20b. In FIG. 20a, electrodes 302 are shown deployed in prostate 305. The broken line represents the balloon 301. In FIG. 20b, the catheter 300 has been rotated by force 306, causing the electrodes 302 to assume a new position and opening up gaps 307 through which the gases may escape. In alternative embodiments, other means for removing gases may be used. For example, gas may be vented by having a negative pressure in the delivery system or catheter to effectively vacuum gas away from the active electrode(s).

Figure 21A:
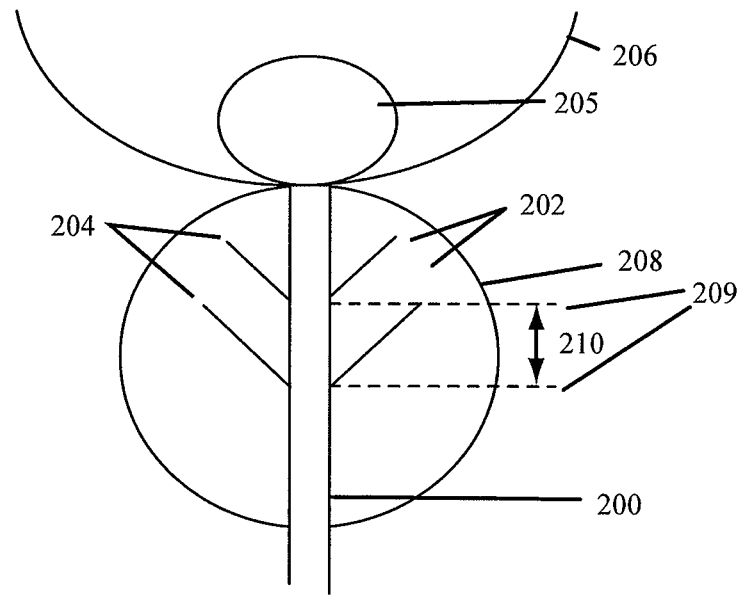
FIG. 21a illustrates a coronal view of a system comprising two axial planes of four electrodes each, in accordance with one embodiment.
Figure 21B:
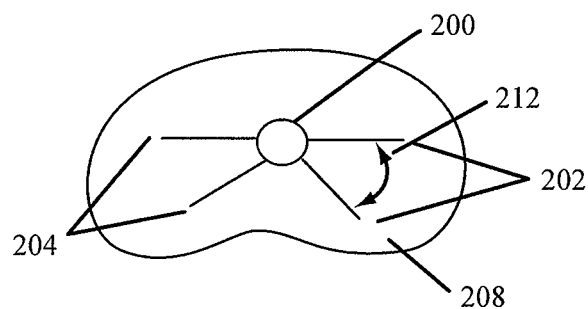
FIG. 21b illustrates a transverse view of a system comprising four electrodes in each axial plane, in accordance with one embodiment.

FIGS. 21a and 21b illustrate an embodiment comprising of two axial planes of four electrodes and illustrate the axial electrode spacing and angular separation. FIG. 21a is a coronal or top view and FIG. 21b is a transverse or end view. The system is shown including a catheter 200, a plurality of electrodes including two electrodes 202 on one side of the catheter 200 and two electrodes 204 on the other side of the catheter 200, and a fixation element 205. The catheter 200 is deployed transurethrally and the fixation element 205 positioned in the bladder 206 such that deployment of the electrodes 202 is into the prostate 208. As shown in FIG. 21a, an axial spacing 210, comprising the distance between the electrodes 202 or 204 on each side of the catheter 200, is provided between the electrodes 202 or 204. Dashed lines 209 indicate the longitudinal position of the electrodes 202 relative to the catheter 200. As shown in FIG. 21b, an angular spacing 212, comprising the distance between the electrodes 202 or 204 on each side of the catheter 200, is provided between the electrodes 202 or 204. The angular spacing is the angle between the posterior and anterior electrode on each side of the catheter.

Providing multiple electrodes to an area to be ablated can reduce the number of coulombs or the dose required from each electrode, thus decreasing the amount of gas created at each electrode. In some embodiments, no single electrode delivers more than approximately 72 coulombs. In one embodiment, each electrode delivers between approximately 24 and 48 coulombs of charge with an axial electrode spacing (measured down the catheter) of approximately 8 to 10 mm and an angular separation of between approximately 15 to 65 degrees. A suitable angular spacing is approximately 30 to 45 degrees with 35 degrees being optimal in certain embodiments. The axial spacing could be increased to 12 to 16 mm and up 20 mm if the dosing is increased. The axial separation could be reduced to 4 to 6 mm if dose per electrode is reduced and the number of electrodes is increased.

During treatment, the electrodes may lose ohmic contact with different types of tissues, thereby making it difficult to deliver the desired current. When contact is lost, it can cause the treatment zone to become more unpredictable and muscle contractions can occur due to spikes in voltage and current. Loss of contact may take place for multiple reasons including, at least:

1) Hydrogen gas created from the cathode reaction or oxygen gas from the anode reaction may saturate electrode surface and cause an increase of impedance;
2) Chlorine gas created from the anode reaction may saturate electrode surface and cause an increase of impedance; and 3) The reaction at the anode may cause local dehydration and cause the tissue proximate to the electrode to lose its conductive properties.

In some embodiments, actions may be taken to prevent an increase in impedance or to counteract an increase in impedance arising at least from these sources. In one embodiment, a positive force may be added to the tissue using the active portion of the electrode, by the shape of the electrode design, or by using an array of electrodes and sequencing the therapy to allow natural diffusion within prostatic tissue to overcome the increase of impedance at the electrode site. Force to the electrode can be accomplished by adding a torque, an axial load down the electrode, or an axial load down the catheter.

Figure 22A:
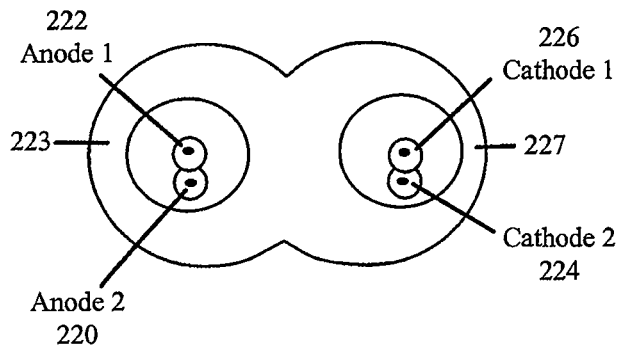
FIG. 22a illustrates two cathodes in parallel and two anodes in parallel and the associated treatment zones with moderate resistance, in accordance with one embodiment.
Figure 22B:
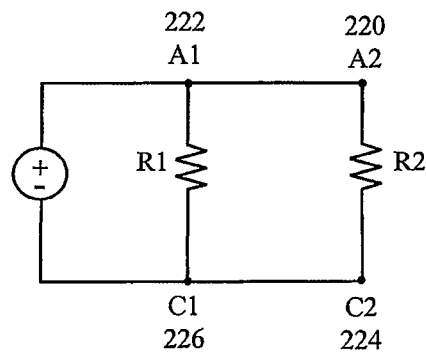
Figure 22C:
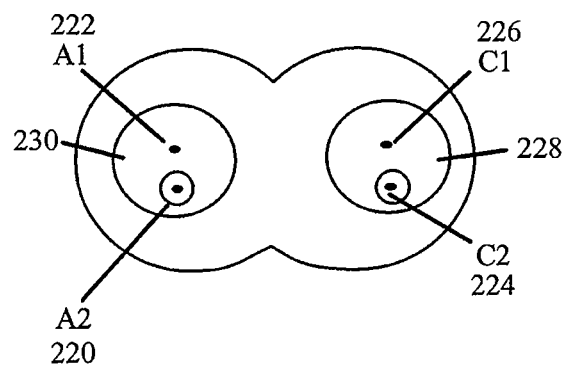
FIG. 22c illustrates treatment zones with high resistance, in accordance with one embodiment.

In another embodiment, an array of electrodes may be used including either or both of multiple cathodes and anodes in parallel with each other to deliver the therapy. For example, as shown in FIGS. 22a and 22c, multiple anodes and multiple cathodes may be provided in parallel. FIG. 22a illustrates a first anode 222, a second anode 220, a first cathode 226, and a second cathode 224. FIG. 22a further illustrates the treatment areas 223 and 227 associated with the anodes 222, 220 and the cathodes 226, 224, respectively. Generally, each electrode of an anode pair or cathode pair may be at approximately the same potential and be placed in close proximity. Providing electrodes in parallel and in close proximity can ensure continued treatment even if one electrode loses contact. More specifically, if one anode (or cathode) of an anode (or cathode) pair loses contact, the area will continue to be treated by the other anode (or cathode) in parallel. This is true whether the electrode pair is an anode pair or a cathode pair. FIG. 22a illustrates a pair of anodes 220 and 222 in parallel and a pair of cathodes 224 and 226 in parallel. FIG. 22b illustrates an electric current diagram for FIG. 22a. FIG. 22c illustrates the effective treatment areas 230 and 228 resulting from R1 and R2, respectively, of FIG. 22b. As shown, the effective treatment areas 230 and 228, or areas ablated, approximate the effective treatment areas 223 and 227 of FIG. 22a, where no impedance problems occur. While FIGS. 22a-22c illustrate two anodes and two cathodes, more than two electrodes may be put in parallel.

In one embodiment, the generator may be configured to monitor a measurement of impedance between the electrodes and uses a pattern of impedance measurements to predict a significant increase in impedance. Upon prediction of an increase in impedance, the generator reduces the current level or turns off the current, thereby preventing a current spike that could cause nerve stimulation.

Various current delivery mechanisms may be used to reduce the likelihood of stimulating nerves. In one embodiment, the generator utilizes a current source circuit with a high voltage compliance. Voltage compliance (or compliance voltage) is the maximum voltage a current source will go to in its attempt to source the programmed current. Compliance voltage values may be user settable, allowing user control over the sourcing and measurement process. If the generator voltage compliance is higher than the current level multiplied by the impedance, the current is controlled and current spikes are substantially prevented. For example, a voltage compliance of 200 V allows the current source to deliver a current of 20 mA without current spike due to an impedance change of 10 k$\Omega$.

The likelihood of sudden impedance changes can be reduced by using low current, such as less than or equal to about 30 mA. The low current substantially prevents the gas generation rate from greatly exceeding the rate that the gas escapes from and/or diffuses into tissue.

In another embodiment, to reduce the likelihood of sudden impedance changes and to complete treatment in a relatively short time frame, treatment may be started with a relatively high current, for example approximately 50 mA, and the current level may be reduced one or more times during the treatment, for example to a level less than about 20 mA. At the start of treatment, using the high current level, gas is generated at a high rate. Before enough gas accumulates to cause the electrode to lose contact with the tissue, the gas generation rate is decreased, by reducing current level, to better balance the gas generation and gas escape/diffusion rates.

In yet another embodiment, a low level current (between approximately 1 mA and approximately 2 mA) can be applied for a short time (for example, less than about 5 minutes) before ramping up the current level. With the short delivery of a low level current, the area around the anode dehydrates and holds the anode in place. The forced contact between electrode and tissue may reduce impedance levels.

In a further embodiment, a low level current (between approximately 1 mA and approximately 2 mA) of opposite polarity from what will be used in the treatment may be applied for a short time (for example, less than about 5 minutes) before ramping up. The current may change the properties of the tissue around each electrode to reduce an impedance problem before ramping up the current.

System for Treatment

Various embodiments of systems for treating tissue using direct current ablation are described herein. It is to be appreciated that while specific dimensions or materials may be described, these are for the purposes of illustration only and other suitable dimensions or materials may be used.

Figure 23:
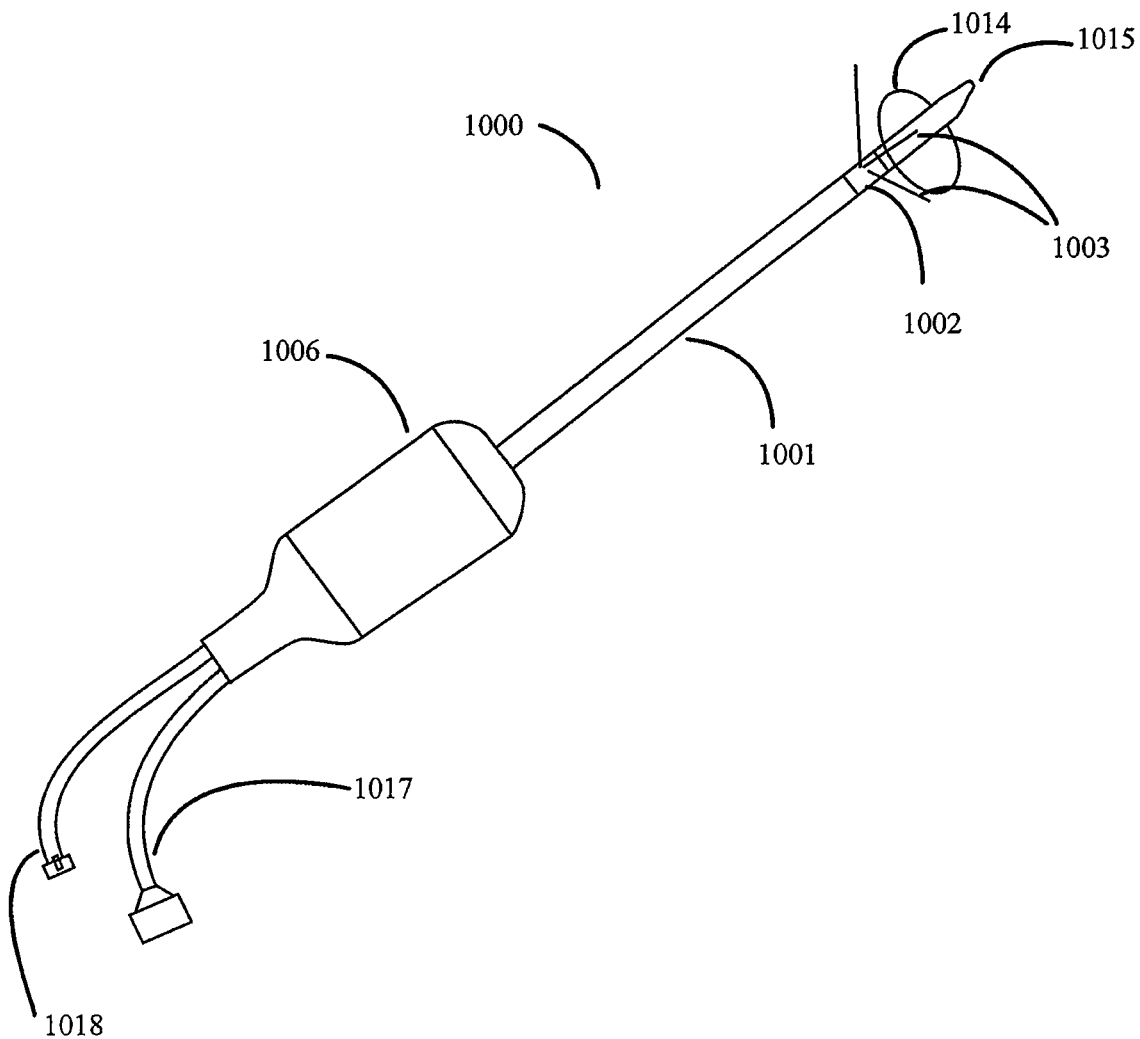
FIG. 23 illustrates a device for treating tissue, in accordance with one embodiment.

FIG. 23 illustrates an embodiment of a single use translumen catheter 1000 for delivering a non-thermal DC ablation treatment to tissues in proximity to the lumen. As shown in FIG. 23, the catheter 1000 comprises of a flexible outer catheter or sheath 1001 for routing the device through a body lumen (e.g. urethra), a plurality of electrodes 1003 to deliver treatment, a director 1002 for routing the electrodes 1003 into the tissue to be treated, a fixation element 1014 (e.g. a silicone inflatable balloon, a soft tip 1015 for easy introduction and routing in the lumen, a handle including an actuating mechanism 1016 for deploying the electrodes 1003 into the tissue and for retracting the electrodes 1003 back into the catheter, an electrical connection and connector 1017, and a port and valve 1018 for activating and deactivating the fixation element. In the preferred embodiment, the length of the tip 1015 is 58 mm. In other embodiments the tip 1015 could be 20 to 75 mm in length. In the preferred embodiment, the length of the director 1002 is 8.5 mm. In other embodiments the director 1002 could be 5 to 60 mm in length. In the preferred embodiment, the length of the outer sheath 1002 is 256 mm. In other embodiments the outer sheath 1002 could be 100 to 750 mm in length. In the preferred embodiment, the length of the handle 1016 is 243 mm. In other embodiments the handle 1016 could be 100 to 500 mm in length. The embodiment of FIG. 23 is configured for any type of electrode deployment (linear or rotational). In one example the catheter is inserted through the urethra for deploying electrodes into the prostate and delivering DC ablation to the prostate to treat BPH.

Figure 24:
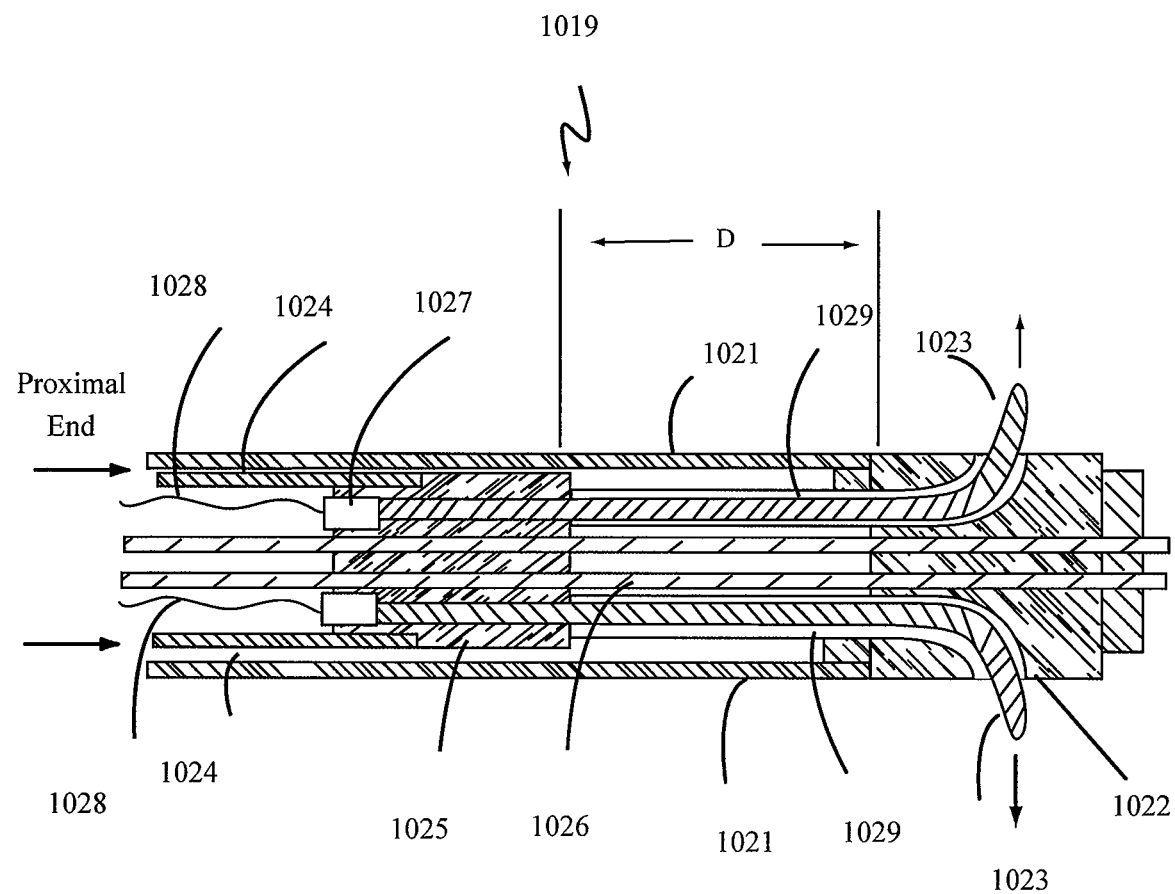
FIG. 24 illustrates a cross-section of the distal end of the catheter shown in FIG. 23, with linear deployment of the electrodes, in accordance with one embodiment.

FIG. 24 illustrates linear deployment of the electrodes. As shown, in the cross-section in FIG. 24, the catheter 1019 includes an outer sheath 1021, an electrode director 1022, a plurality of electrodes 1023, an inner sheath 1024, an electrode driver 1025, a fixation element fill tube 1026, an electrical connection to the electrodes 1027, insulated electrical conductors 1028, and insulation on the electrodes 1029. As the catheter 1019 is inserted through the lumen in the body for positioning prior to deployment, the electrodes 1023 are completely within the catheter 1019 to substantially prevent damaging the lumen or urethra. After the catheter 1019 is positioned and the fixation element activated, the electrodes 1023 are deployed into the tissue to begin treatment. In one embodiment the inner sheath 1024 is advanced through the outer sheath 1021. The driver 1025 is mechanically coupled to the inner sheath 1024, and the electrodes 1023 are fixed to the driver 1025. Thus the electrodes 1023 may be advanced distally and through the electrode director 1022 which is attached to the outer sheath 1021. In another embodiment the outer sheath 1021 may be pulled back over the inner sheath 1024, thereby forcing the electrodes 1023 out into the tissue through the director 1022.

In various embodiments, the driver/director interactions may be configured to reduce buckling. More specifically, the electrode driver 1025 and director 1022 may be positioned at a minimal distance D from each other to minimize buckling stresses in the electrodes 1023 during deployment. The distance between the driver 1025 and the director 1022 generally may be a minimum of the desired insertion length of the electrodes into the tissue. As can be appreciated by those skilled in the arts, the larger the electrode diameter, the larger the permissible distance between the director and driver. Various examples are given for the purposes of illustration. When using an electrode between approximately 0.25 and 0.65 mm in diameter, the driver and director may be a maximum distance of between approximately 14 and 24 mm apart. This short distance of unsupported electrode substantially prevents buckling failure. In these embodiments the catheter may be made of a composite of polymer materials to facilitate bending of the catheter. In one embodiment the FIG. 24 further illustrates the inner sheath of a catheter for linear electrode deployment.

The inner sheath 1024 may comprise material that is flexible but has a higher axial elastic modulus. This provides flexibility to the catheter 1019 to facilitate introduction and routing in a body lumen such as the urethra while retaining dimensional stability when an axial load is placed on it such as when the electrodes are deployed and retracted. Suitable materials may include, for example, PEEK, braided PEBAX, or Polycarbonate with or without carbon fill. A coextruded polymer with metallic or carbon fibers provides bending flexibility and axial dimensional stability. The inner sheath 1024 generally may have an outer diameter small enough to slide within the outer sheath 1021, yet not so small as to allow the inner sheath 1024 to buckle within the outer sheath 1021. A suitable outer diameter of the inner sheath 1024 is between approximately 4.0 and 5.6 mm. The wall thickness of the inner sheath may be approximately 0.26 to 0.46 when using PEEK as a material. One embodiment uses an outer diameter of 4.8 mm and 0.30 mm wall thickness for the inner sheath 1024.

In the embodiment shown, the inner sheath 1024 is mechanically coupled to the driver 1025. Such coupling may be done in any suitable manner. For example, this may be done with an adhesive, such as cyanoacrylate, an epoxy, welded ultrasonically, or welded with heat. In some embodiments, the driver may be made out of a non-conductive material, with good dimensional stability such as polycarbonate, PEEK, or ABS. A glass or carbon filled material may be used for further dimensional stability.

In the embodiment shown, the driver 1025 is mechanically coupled to the fixation element fill tube 1026. The driver 1025 thus may be used to move the fill tube 1026 relative to the outer sheath 1021, distal tip of the catheter, and fixation element (for example, a balloon). In this embodiment, a sliding seal may be provided from the fixation element fill tube 1026 to the distal tip to allow balloon inflation. This may be accomplished by o-ring features in the distal tip that fit tightly over the distal end of the fill tube. In another embodiment the fill tube 1026 may slide through the driver 1025 during electrode deployment and retraction and may be anchored in the director 1022. The outside diameter of the driver 1025 may generally be the same or larger than the outside diameter of the inner sheath 1024. The outside diameter of the driver 1025 may be less than the inner diameter of outer sheath 1021.

In the embodiment shown, the electrodes 1023 are mechanically coupled to the driver 1025. Such coupling may be done in any suitable manner. For example, the coupling may be by adhesive or mechanical interference. In the embodiment shown, the electrical connection is provided by a crimp tube 1027 and may be used to anchor the electrodes in the driver 1025. In some embodiments, between 2 and 12 electrodes 1023 may be captured in the driver 1025.

Figure 25A:
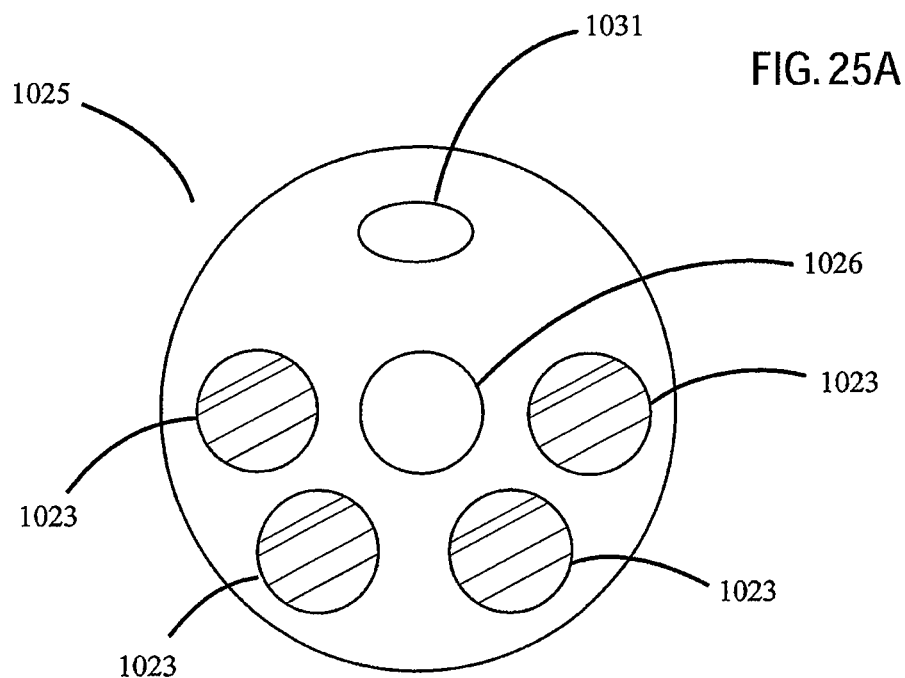
FIG. 25a illustrates a top end view of an electrode driver having four electrodes and showing the position of the holes for holding the electrodes and for utility lines, in accordance with one embodiment
Figure 25B:
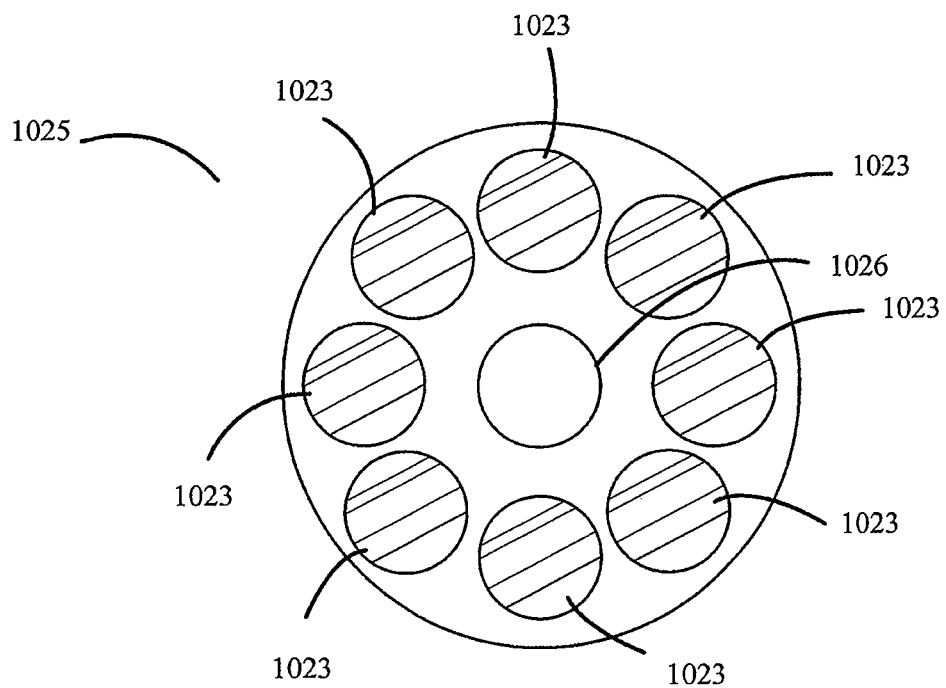
FIG. 25b illustrates a bottom end view of an electrode driver having eight electrodes and showing the position of the holes for holding the electrodes and for utility lines, in accordance with one embodiment.

FIGS. 25*a* and 25*b* illustrate electrode 1023 placements within the driver 1025. FIGS. 25*a* and 25*b* illustrate drivers 1025 for differing numbers of electrodes 1023. FIG. 25*a* illustrates a driver 1025 for deploying 4 electrodes 1023. FIG. 25*b* illustrates a driver 1025 for deploying 8 electrodes 1023.

FIG. 25*a* illustrates a top end view of an electrode driver 1025 having 4 electrodes 1023 and showing the position of the routing holes for the electrodes and for utility lines. Utility lines may comprise, for example, pneumatic/hydrolytic/saline flush lines. In addition to routing holes for 4 electrodes, the driver 1025 includes a hole 1031 though which the urethra may be supplied with saline to buffer treatment in the urethra, and a hole for a balloon fill tube 1026.

FIG. 25*b* illustrates a bottom end view of an electrode driver 1025 having 8 electrodes 1023 and showing the position of the routing holes for the electrodes and for utility lines. In addition to routing holes for 8 electrodes, the driver 1025 includes a hole for a balloon fill tube 1026.

In some embodiments the driver may comprise two parts which are assembled around the crimp joint from the electrodes to the electrical conductors. This mechanically locks the electrodes in place within the driver. In one embodiment the electrodes are allowed to rotate within the two piece driver and are properly aligned by mating the curved section in the director with the pre-shaped curve in the electrodes. In another embodiment the electrode assemblies are insert-molded within the driver. In another embodiment the driver has a keying feature to the electrode crimp tubes which upon assembly allow the electrodes to have proper angular orientation for insertion through the director.

Returning now to FIG. 24, as shown the electrodes 1023 may be mechanically and electrically coupled to conductive elements 1028 that run to the electrical connector (1017 of FIG. 23). Coupling may be done in any suitable manner. For example, the electrodes may be attached by a crimp tube 1027, welded, or soldered if the plating on the electrodes allows. When deployed or retracted from the tissue the electrodes are allowed to slide through the radiused channels (routing holes) in the director 1022 in FIG. 24. The shapes and orientations of these channels direct the electrodes in the desired angle from the catheter into the tissue. The electrodes may be insulated 1029 with polyimide, Parylene, PEEK, silicone, PTFE, or ETFE around their outer diameter. The insulation thickness may range from 0.02 to 0.10 mm. Co-pending patent application Ser. No. 12/544,119 discusses suitable electrodes for use in systems for treating tissue and is herein incorporated by reference in its entirety.

Figure 26A:
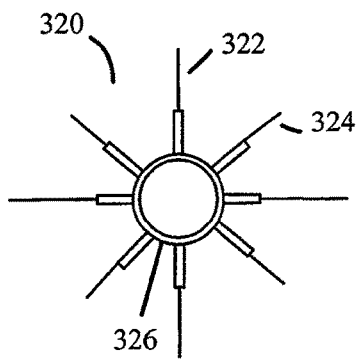
FIG. 26a illustrates an end view of a catheter having eight electrodes in a deployed configuration, in accordance with one embodiment.
Figure 26B:
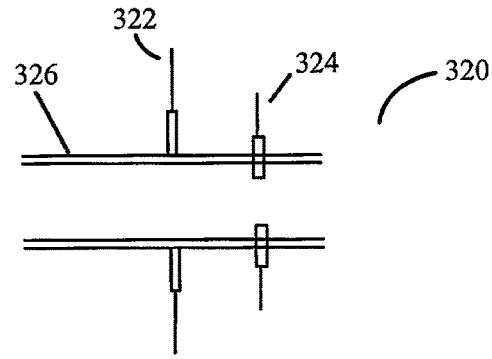
FIG. 26b illustrates a side view of the catheter with the electrodes deployed approximately normal to the catheter with all electrodes deployed at the same normal angle, in accordance with one embodiment.
Figure 26C:
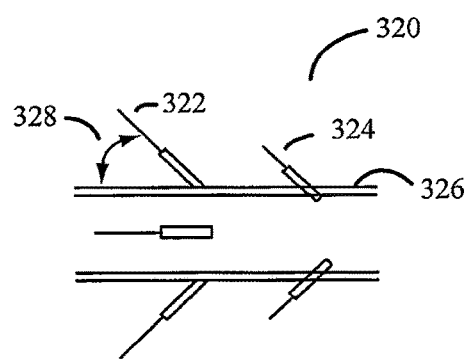
FIG. 26c illustrates a side view of the catheter of with the electrodes deployed at a non-normal angle to the catheter with all electrodes deployed at the same non-normal angle, in accordance with one embodiment.
Figure 26D:
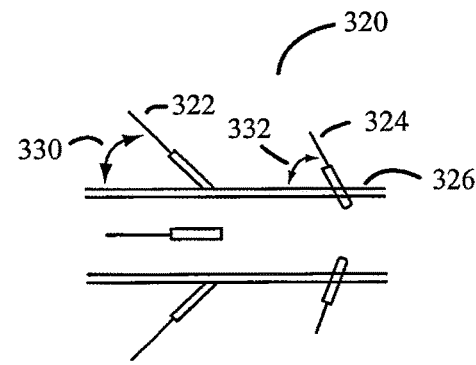
FIG. 26d illustrates a side view of the catheter of with the electrodes deployed at a non-normal angle to the catheter with a first row of electrodes deployed at a first non-normal angle and a second row of electrodes deployed at a second-non-normal angle, in accordance with one embodiment.

FIGS. 26*a*-26*d* illustrate systems 320 with various deployments of electrodes from a catheter through a director FIG. 26*a* illustrates eight electrodes 322 and 324, deployed from the catheter 326. Four electrodes 322 are longer than the other four electrodes 324. As shown in FIG. 26*b*, in some embodiments, the four long electrodes 322 may be on one level and the four short electrodes 324 may be on another level. In other embodiments, long electrodes and short electrodes may be provided on the same level. In some embodiments, the electrodes may be deployed at non-normal angles to the catheter. FIG. 26*c* illustrates an embodiment wherein all electrodes 322, 324 are deployed at angle 328. FIG. 26*d* illustrates an embodiment wherein some electrodes 322 are deployed at angle 330 and other electrodes 324 are deployed at angle 332. Thus, FIGS. 26*a*-26*d* illustrate the flexibility of electrode deployment to reach a multitude of tissue areas. Variously, a plurality of electrodes of different lengths, at different levels, and at different angles, provide the opportunity to treat the geometry and size of an individual tissue area safely while reducing the time of treatment and the number of times the catheter must be redeployed and repositioned. Further, by facilitating nearly simultaneous deployment of a plurality of electrodes, a single "stick" of electrodes, catheter position, and treatment can be used for tissue treatment. This also reduces trauma, discomfort, the need for follow-up treatments, and perhaps cost to the patient.

Figure 27A:
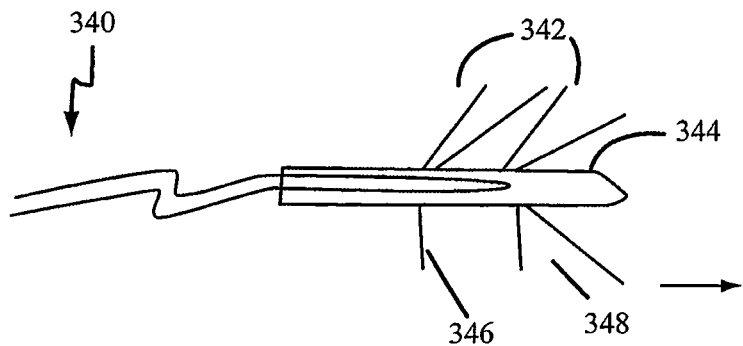
FIG. 27a illustrates a system having 2 rows of and a total of 7 electrodes, in accordance with one embodiment.
Figure 27B:
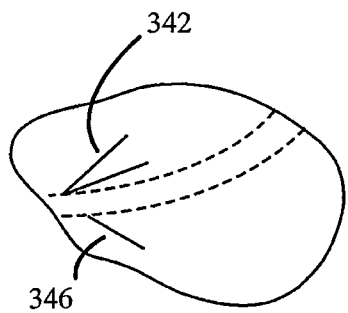
FIG. 27b illustrates a side view of a first row of the embodiment of FIG. 27a, the first row having 3 electrodes.
Figure 27C:
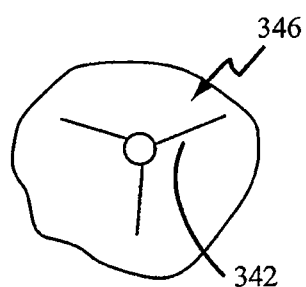
FIG. 27c illustrates an end view of a first row of the embodiment of FIG. 27a, the first row having 3 electrodes.
Figure 27D:
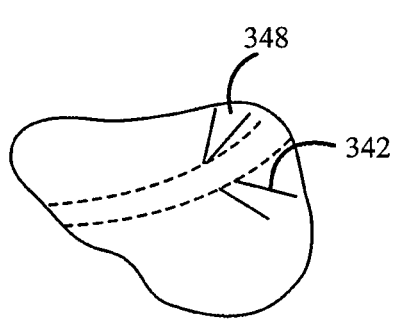
FIG. 27d illustrates a side view of a second row of the embodiment of FIG. 27a, the first row having 4 electrodes.
Figure 27E:
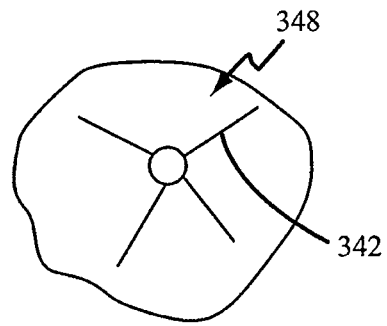
FIG. 27e illustrates an end view of a second row of the embodiment of FIG. 27a, the first row having 4 electrodes.

FIGS. 27*a*-27*e* illustrate a custom electrode deployment configuration specific to prostate treatment. FIG. 27*a* illustrates the overall device 340. As shown in FIG. 27*a*, seven pin electrodes 342 are deployed through a catheter 344. The device 340 includes two rows, a first (proximal) row 346 of three electrodes 342 and a second (distal) row 348 of four electrodes 342. FIGS. 27*b* and 27*c* illustrate the first row 346 of three electrodes 342. FIGS. 27*d* and 27*e* illustrate the second row 348 of four electrodes 342. The electrodes 342 may be driven by an internal cam or other driving mechanism. The three proximal electrodes of the first row 346 may have, for example, between approximately 5 mm and approximately 20 mm separation and approximately 45 degree rotation from the four distal electrodes of the second row 248. In some embodiments, the proximal row 346 of three electrodes 342 may have a shallower angle because they may treat a flatter section of the prostate. The configurations shown in FIGS. 27*a*-27*e* facilitate close (small) location and efficient treatment of the prostate.

FIGS. 27*b* and 27*c* illustrate the proximal row 346 of electrodes 342. FIG. 27*b* is a prostate side view, showing the urethra. FIG. 27*c* is a prostate end view, showing the urethra. FIGS. 27*d* and 27*e* illustrate the distal row 348 of electrodes 342. FIG. 27*d* illustrates a prostate side view, showing the urethra. FIG. 27*e* shows a prostate end view, showing the urethra. Each of FIGS. 27*b*-27*e* illustrate the electrodes 342 as deployed.

In some embodiments, the depth of electrode insertion may vary between approximately 8 mm and approximately 25 mm and the angle of insertion may vary from approximately 10 to approximately 90 degrees from the axis of the catheter depending on the size of the tissue anatomy and targeted zone for treatment. In one embodiment the catheter has indicators which indicate when the electrodes have been deployed 14, 16, 18, 20, and 22 min. In another embodiment the catheter has indicators which indicate when the electrodes have been deployed 6, 8, 10, 12, 14, and 16 mm. Depending on the area to be treated, the electrodes may be extended between 6 and 24 mm. The active portion of the electrode may vary in length between approximately 3 mm and approximately 12 mm along the inserted portion of the electrode. The position of the active portion of the electrode along the inserted length depends on the electrode's position within the tissue, for example, within the prostate and its relative position to the urethra and prostate capsule. An electrode that is near the prostate apex or bladder neck will have an active portion in the middle of the inserted length. An electrode near the middle of the prostate (its widest point) will have an active electrode at the distal end of the inserted length. In one embodiment all electrodes have the active area at the distal end of the electrode.

Figure 28A:
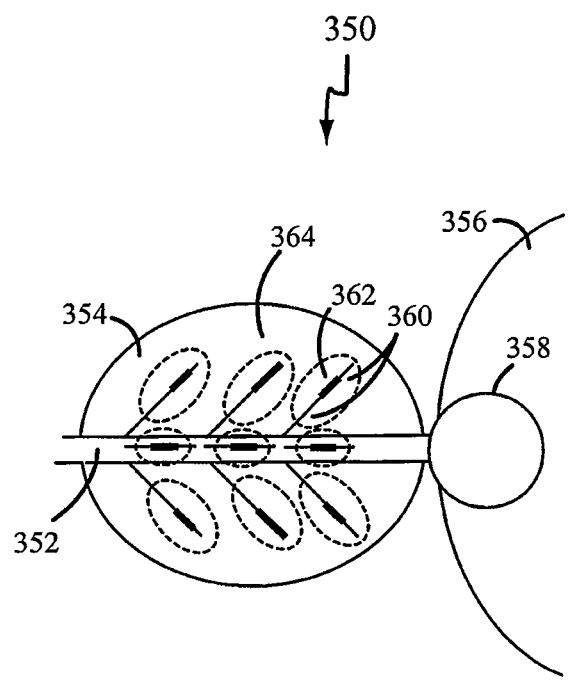
FIG. 28a illustrates a deployed electrode configuration, in accordance with one embodiment.
Figure 28B:
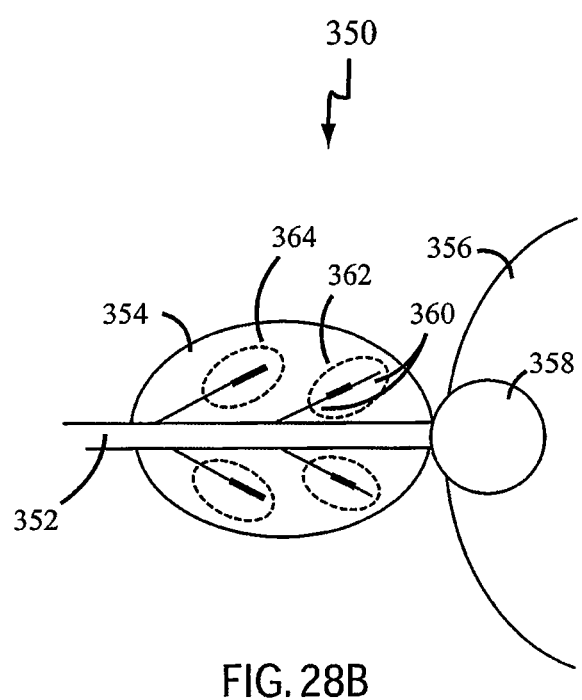
FIG. 28b illustrates a deployed electrode configuration, in accordance with another embodiment.

FIGS. 28*a* and 28*b* show examples of deployed electrode configurations of devices 350. In both figures the urethra 352 is shown extending through the prostate 354 into the bladder 356. The system includes a catheter deployed in the urethra 352. The catheter terminates in a balloon 358. FIG. 28*a* illustrates an embodiment having twelve electrodes 360, each of which has insulation sleeve 362. Six of the electrodes 360 are shown extending laterally from the catheter in the urethra 352. Three of the electrodes 360 are shown extending outwardly from the paper and it is to be appreciated that three of the electrodes extend into the paper. FIG. 28*b* illustrates an embodiment having four electrodes 360, each of which has insulation sleeve 362. The electrodes 360 are of the length and location to create the desired zones 364 of necrosis in accordance with the shape and size of prostate 354. Insulation sleeve 362 can be used to separate two different active surfaces on the same electrode. The electrode then consists of two conductors forming a bipolar electrode. The bipolar electrode may allow for more precise control and tailoring of the treatment. The disadvantage of the bipolar electrode is in the complexity of the electrical connections in the catheter.

Figure 29:
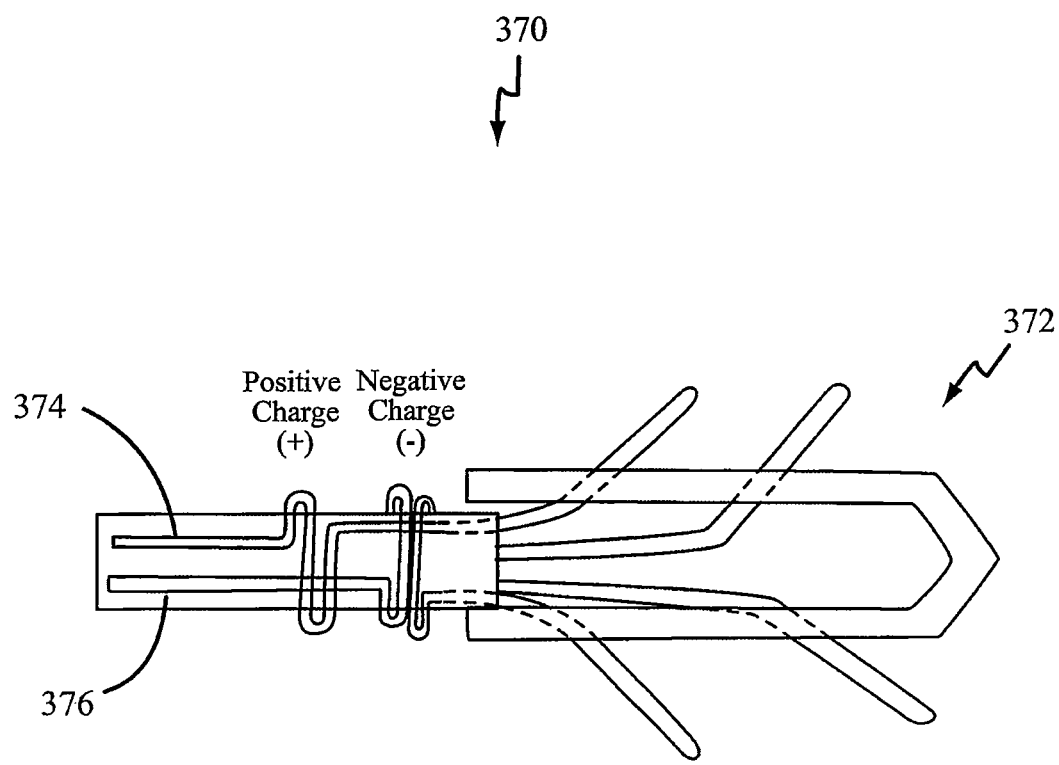
FIG. 29 illustrates a cross-section of a distal portion of a device including an anode ring that is the common connection for all anode electrodes, and a cathode ring that is the common connection for all cathode electrodes, in accordance with one embodiment.

FIG. 29 illustrates a portion of a device 370 having an alternative electrode deployment embodiment. As shown, the deployment comprises a linear deployment electrode tip 372 with polarity selection channels 374, 376. The tip includes first and second channels 374, 376 of two different polarities. The first channel 374 is a positive channel and the second channel 376 is a negative channel. In the embodiment shown, the channels are counter sunk channels with exposed linear electrode or insulated in channel to allow the other channel to select polarity. In some embodiments, a flexible wire is attached to each polarity selection and to a connector. Each polarity section 374, 376 has a channel that is available to mate with the exposed end of an electrode, effectively selecting the polarity of the electrode 372. While FIG. 29 illustrates 2 electrodes, the embodiment of FIG. 29 facilitates polarity selection for an unlimited number of electrodes. Further, multiple pairs of channels may be provided to allow for multiple polarity pairs.

Figure 30:
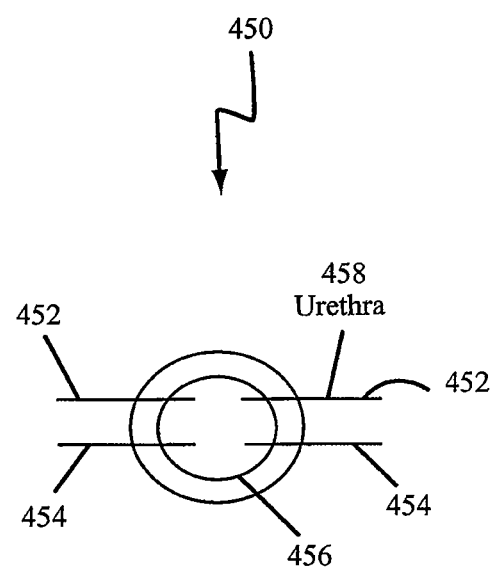
FIG. 30 illustrates an end view of a catheter with diametrically opposed electrodes, in accordance with one embodiment.

FIG. 30 illustrates electrodes diametrically opposed to one another. Such electrodes can enhance the performance of electrode penetration by force balancing the system. As shown, the system 450 comprises a catheter 456 deployed in the urethra 458. Two electrode pairs, first electrodes 452 and second electrodes 454, are deployed from the catheter 456 through the urethra 458. Paired electrodes push tissue in opposite directions as they deploy into tissue. This holds the catheter 456 substantially in place during deployment of the electrodes. Tissue deflection further is reduced during electrode insertion by approximately 1-2 mm before puncture, thereby reducing the electrode diameter required for puncture by approximately 10 to 15%. Returning now to FIG. 24, description will be made of the director materials and geometry. The director 1022 as shown in FIG. 24 may be constructed out of dimensional stable non-conductive material such as PEEK, polycarbonate, Ultem, or ABS.

Figure 31:
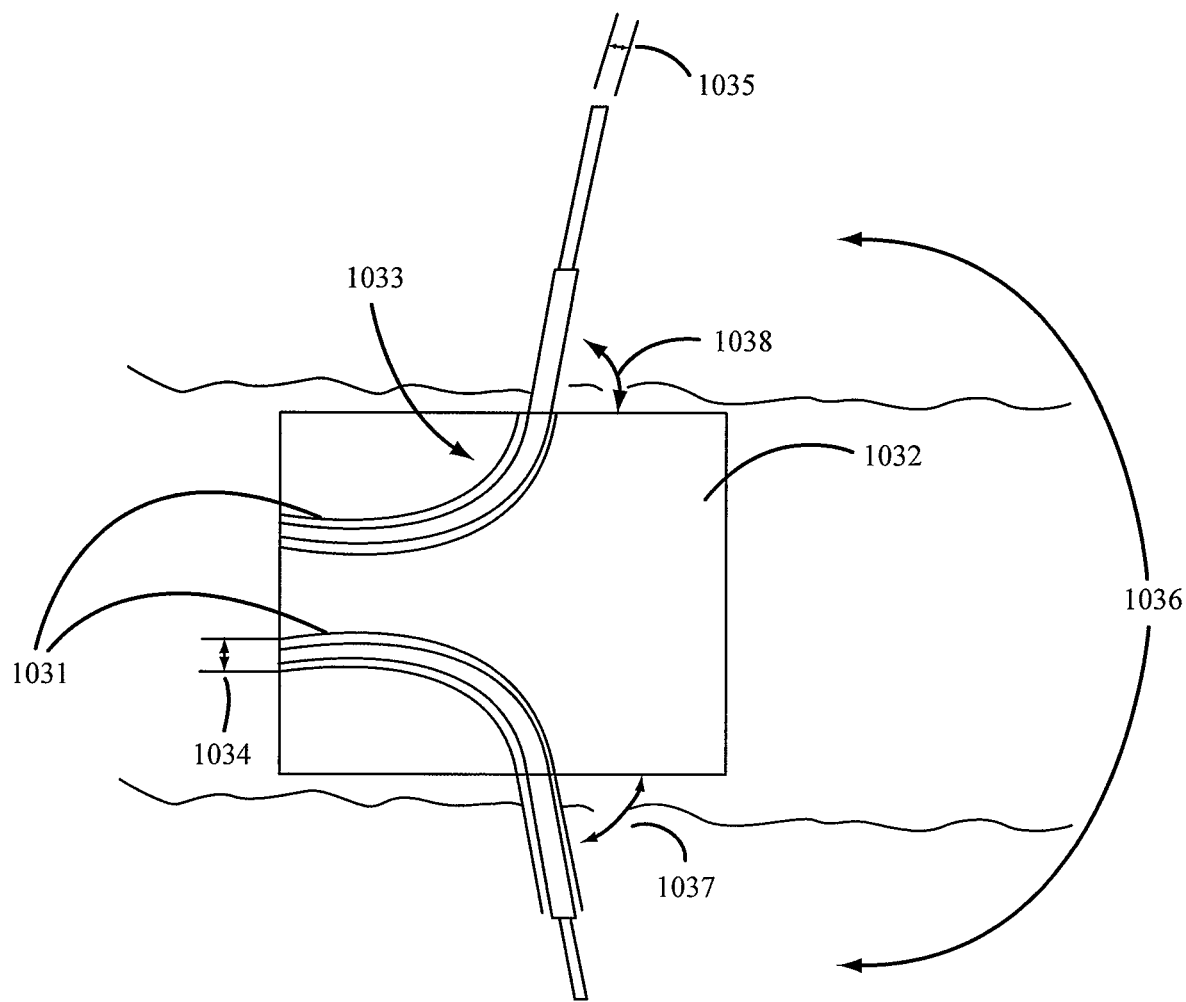
FIG. 31 illustrates a side view of the distal end of a device and the design of a director for linear electrode deployment, in accordance with one embodiment.

FIG. 31 illustrates a side view of the distal end of a device and the design of a director for linear electrode deployment, in accordance with one embodiment. As shown in FIG. 31, the channels 1031 (also referred to as routing hole) in the director 1032 that direct the electrodes may have a radius 1033 of between approximately 5 and 7 mm, and a diameter 1034 of approximately 0.8 mm. This radius 1033 and diameter 1034 facilitates direction of 0.46 mm diameter electrodes 1035 into the tissue 1036 at an angle 1037 of approximately 40 to 50 degrees from the axis of the catheter towards the distal end of the catheter. The tangency of the radius 1038 of the channels 1031 may be approximately 40 to 50 degrees from the axis of the catheter as it exits the director 1032. In another embodiment the channels 1031 have a diameter of 0.5 to 1.5 mm for a corresponding electrode diameter of 0.25 mm to 0.75 mm. The channel diameter may be approximately 1.6 to 2.0 times the diameter of the electrode 1035. As can be appreciated by those skilled in the art, a large channel radius and more acute tangency angle allows for a more acute electrode deployment angle. In one embodiment a radius for deploying an electrode at 15 to 30 degrees from the axis of the catheter is 10 to 14 mm with a tangency angle of 15 to 30 degrees. The channels 1031 may run outward along the center radius of the director or as close to this route depending on the desired electrode array to minimize the force required to deploy the electrodes 1035.

Figure 32A:
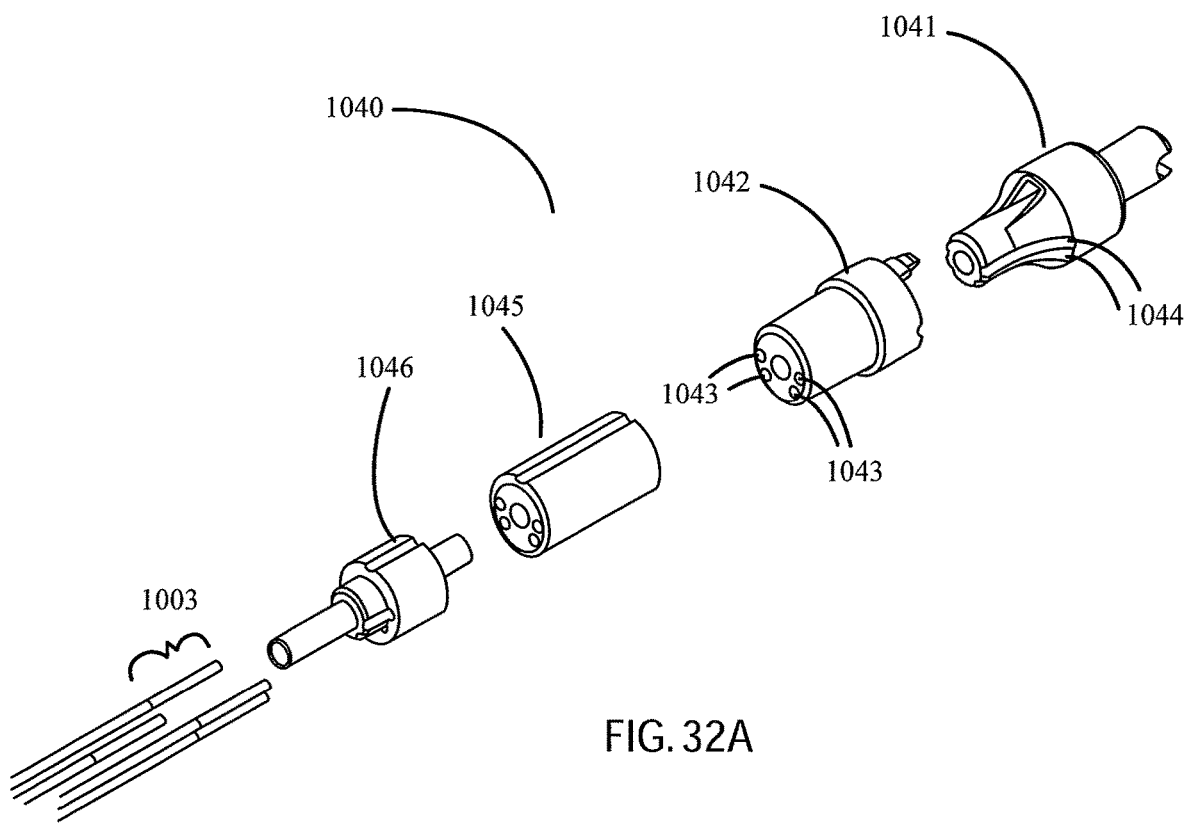
FIG. 32a illustrates an exploded view of the distal end of a four electrode catheter with linear electrode deployment, in accordance with one embodiment.
Figure 32B:
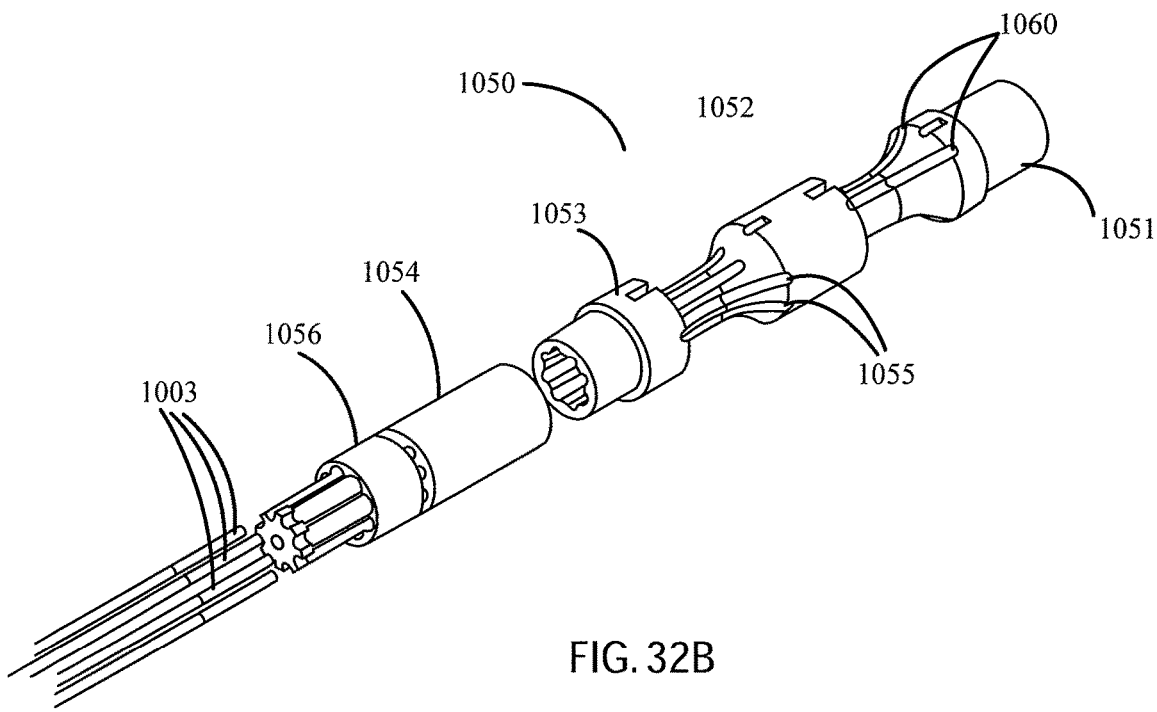
FIG. 32b illustrates an exploded view of the distal end of an eight electrode catheter with linear electrode deployment, in accordance with one embodiment.

FIGS. 32a and 32b illustrate embodiments of directors for a 4 electrode configuration 1040 and an 8 electrode configuration 1050, respectively. FIG. 32a shows a director with 4 channels with an entrance 1043 and exit 1044 for directing 4 electrodes 1003 into tissue when they are advanced by a driver. The director comprises two pieces 1041 and 1042 and the driver comprises two pieces 1045 and 1046. The director in this embodiment has the electrode channels 1043 and 1044 that direct the electrodes off the axis of the catheter by capturing the electrodes between two sets of channel features. In another embodiment, the director may be made of out of 2 to 4 separate pieces that are mechanically coupled with an adhesive or ultrasonically welded.

Eight electrode channels can be formed out of mating features of director parts 1051 and 1052, and director parts 1052 and 1053, forming channels 1000 and 1055 respectively, as shown in FIG. 32b. The channel features 1000 direct a set of 4 distal electrodes 1003 into tissue. The channel features 1055 direct a set of 4 proximal electrodes 1003 into tissue. In one embodiment elements 1056 and 1054 form the driver and mechanically attach to both the distal and proximal electrodes 1003. Making the director and drivers out of multiple pieces allows it to be injection molded or machined from stock. In one embodiment the 8 and/or the 4 electrode directors and/or drivers may be made out of single pieces by integrating features shown in the multiple pieces shown in FIGS. 32a and 32b.

Returning now to FIG. 23, discussion will be made of director interaction with the outer sheath 1001 and the tapered tip 1015. In the embodiment shown, the director 1002 is mechanically coupled to the outer sheath 1001 on the proximal end, and a tapered tip 1015 on the distal end. Coupling may be done in any suitable manner. For example, coupling may be done with adhesive or a mechanical interlock. The tapered tip 1015 may comprise a softer, compliant, and chemically resistant material such as silicone rubber. In one embodiment in which the material is silicone, the durometer may be between a durometer of approximately 35 to 80 Shore A. This maximizes the ease of insertion of the catheter into a small lumen and patient comfort as the catheter is advanced through a lumen such as the urethra. The tapered tip 1015 may have a tapered shape. As used herein, tapered is intended to refer to any shape that is non-perpendicular to an axis of the catheter. For example, the tapered tip 1015 may be rounded, angled surfaces, may have a Coude shape, or may be otherwise configured to ease the routing of the catheter through the lumen or urethra. If the tip 1015 is too soft it may buckle back on itself and impede its advancement through the urethra. If the tip 1015 is too hard it may puncture the lumen in which it is being advanced. The length of the tip 1015 may be approximately 40 to 65 mm to allow for fixation element mounting and to prevent buckling. The fixation element 1014 in FIG. 23 is bonded to the tapered tip 1015. One embodiment for a fixation element is a silicone balloon which simplifies bonding with one embodiment of a silicone tip.

Figure 33:
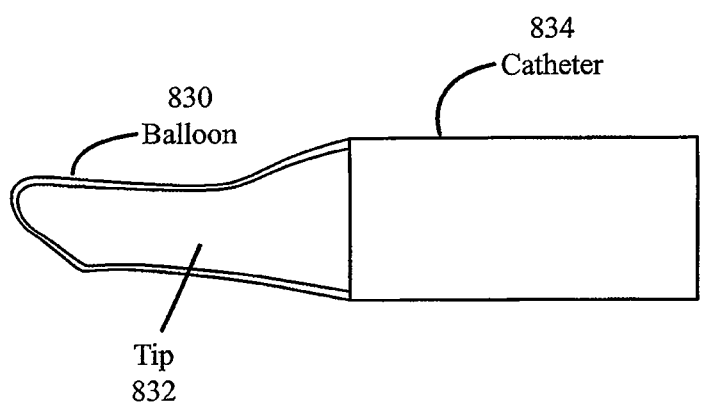
FIG. 33 illustrates a distal fixation element (tip and balloon) on the distal end of a catheter, in accordance with one embodiment.

FIG. 33 illustrates a distal tip with a fixation element provided therearound. As shown, a distal positioning balloon 830 is provided that conforms to the shape of the distal tip 832 of a catheter 834. The balloon 830 is provided over the distal tip 832, thereby reducing drag during the insertion and withdrawal of the system into the vessel (compared to systems having a distal balloon not provided at the tip) because less of the balloon 830 is in contact with the side walls of the vessel into which the device is inserted. This configuration also allows the length of the device to be shortened because the tip surface serves two purposes. One purpose is as a guiding tip surface and the other is as a deflated balloon surface. In another configuration, additional tip length would be required for separate guiding tip and the deflated balloon surfaces. Fixation may further be aided by using, in addition to the balloon, a row of electrodes or inactive tines. The 14-20 mm of tissue, clamped between the balloon (in the bladder) and the electrodes puncturing through the urethra provides for 2 way axial stability of device for a 20-45 minute procedure.

The balloon 830 may be formed of an elastic material having sufficient thickness to assure balloon integrity during inflation, yet sufficiently thin to permit inflation with the required inflation pressure. The balloon 830 may be inflated using, for example, air or saline. Generally, the balloon material should withstand environmental degradation during treatment and allow adhesion to the base material of the distal end of the catheter. In one embodiment, the balloon comprises of silicone rubber of 0.38 mm thickness. Another embodiment of a balloon comprises of silicone rubber 0.20 to 0.77 mm in thickness. Alternative materials, such as polyurethane, may be used. Silicone rubber provides superior chemical resistance from the bi-products of DC ablation. An elastic material facilitates passive return of the balloon to its original configuration when deflated, thus assuring minimal drag during the withdrawing process. The inside surface of the balloon may be configured to be substantially a mirror image of the tip over which it is positioned. Such configuration may be achieved via a molding process or a dipping process. A molding process generally assures a tight, smooth surface on the outside of the balloon, thus minimizing draft during insertion. Thickness, shape, material durometer, consistency of the material, and process may be controlled to assure repeatability in the integrity of the balloon during its expansion, the pressure required for its expansion, and the size of the balloon given a certain pressure. Protrusions of material may be formed on one or both of the surfaces between the balloon and tip to prevent like materials from self-adhering to each other.

Figure 34:
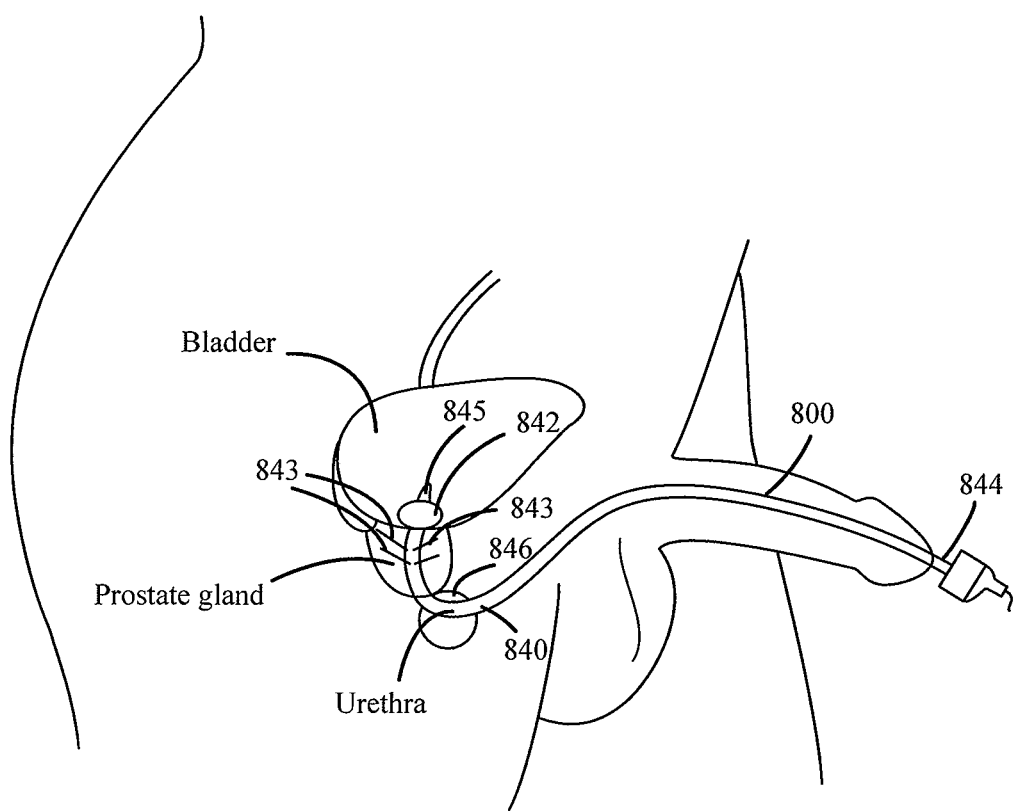
FIG. 34 illustrates a cross-section of the human male anatomy with a catheter in place for treatment of the prostate, in accordance with one embodiment.

FIG. 34 illustrates a system having a long balloon fixation element. As shown, the system includes a transurethral catheter 840 that extends through the urethra, the prostate and into the bladder, with a proximal end 844 remaining outside the urethra, and a distal end 845 extending into the bladder. The distal end 845 is a tapered tip with a distal fixation element 842 attached to it. The distal fixation element is expanded fixing the catheter distal end 845 in the bladder. A proximal fixation device 846 is located proximal to the prostate. Electrodes 843 are extended into the prostate. In accordance with another embodiment, a system and method for BPH treatment, as provided herein, comprises a transurethral catheter including at least one balloon for fixation of the system in a treatment position. In some embodiments, the transurethral catheter comprises a balloon for deployment outside of the prostate for fixation of the catheter in the urethra to substantially prevent longitudinal or rotational motion of the device. In the embodiment shown in FIG. 34, the at least one balloon is a long balloon 846. A long balloon 846 can reduce patient pain that may be associated with a small balloon pressure point. In various embodiments, the balloon may comprise an elastic material such as latex, silicone, or polyurethane, thus requiring relatively low pressures for inflation. The balloon(s) are deflated for insertion of the device, inflated for fixation of the device during treatment, and deflated for withdrawal of the device. The proximal and distal balloon can be inflated or deflated concurrently or independently. In one embodiment the distal balloon is inflated before the proximal balloon.

As shown in FIG. 34 the transurethral catheter 840 may be deployed with a distal end 845 extending into the bladder, the body of the catheter passing through the urethra, and the proximal end 844 of the catheter extending outwardly from the penis of the patient to a handle. A long balloon 846 may be provided on the catheter body. In various embodiments, the balloon 846 may comprise latex, silicone, or polyurethane. The balloon 846 extends for a portion of the distance between the prostate and the end of the penis. In some embodiments, the balloon 846 extends over substantially all of the distance between the prostate and the end of the penis. The extension of the balloon contributes to the available surface area on which pressure from the balloon may be exerted. The balloon 846 is expanded once the catheter 840 is in a desired location. In the expanded condition, the balloon 846 substantially retains the catheter 840, longitudinally and rotationally, in the desired location. When treatment is completed, the balloon 846 is deflated and the system removed.

The stabilizing force of the balloon may be adjusted by adjusting the length of the balloon, the material of the balloon, the thickness of the balloon, the shape of the balloon, the pressure used to inflate the balloon, and/or the manufacturing process used for making and securing the balloon to the surface of the catheter. Placement of the balloon outside of the prostate, extension of the balloon over a large surface area, and relatively low inflation pressures required reduce pain experienced by the patient while providing adequate stability to the device.

Figure 35:
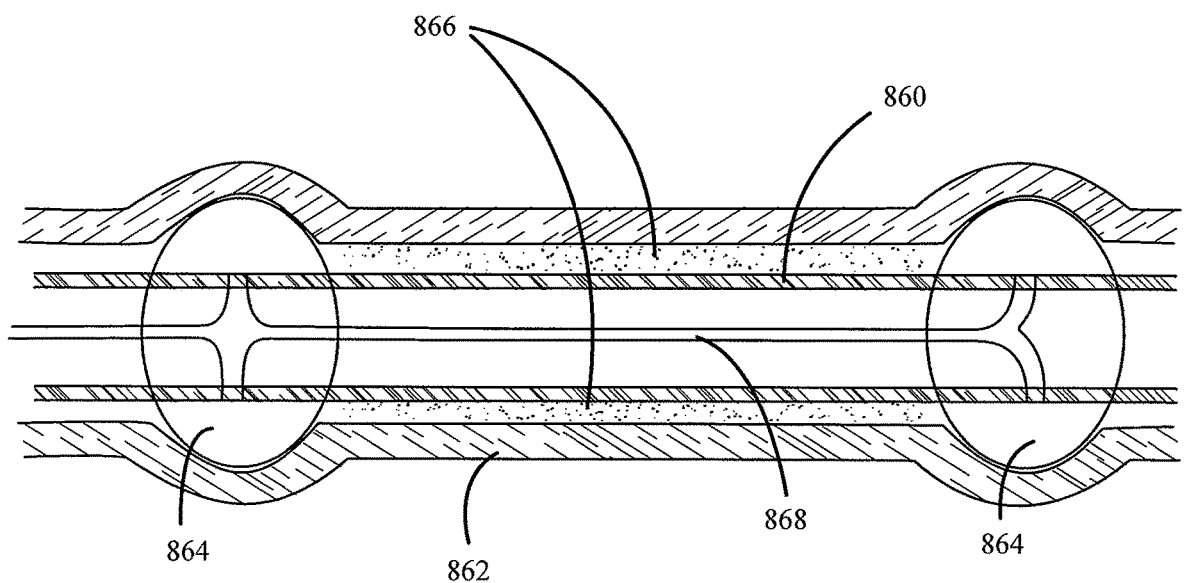
FIG. 35 illustrates a cross-section of the human male anatomy showing the urethra with two separated balloons, in accordance with one embodiment.

FIG. 35 illustrates an embodiment of a fixation device that further acts to substantially block the flow of contaminated materials. FIG. 35 illustrates the catheter, 860a fixation device 864, fluid 866, and a lumen 868. As previously discussed, a system and method for treating BPH may include a catheter inserted into the urethra with electrodes extending into the surrounding tissue. In some embodiments, a fixation device may be provided to substantially block the flow of chemicals created by the electrolysis to structures adjacent to the urethra such as the outer sphincter. It is to be appreciated that such fixation device may be used in other applications for preventing flow of materials downstream. In the embodiment of FIG. 35, the catheter 860 includes balloons 864 as fixation devices. The catheter 860 is deployed in a tissue vessel 862. The balloons 864 are expanded and fluid 866 is contained along the catheter 860 between the balloons 864.

Accordingly, in some embodiments, the fixation device for preventing flow of materials comprises a balloon that substantially blocks a portion of a vessel in which it is deployed until fluids in the blocked portion of the vessel can be diluted such that they do not risk contaminating other areas of the vessel. In some embodiments, the balloon comprises silicone. Silicone is resistant to acid and base as well as the electrolysis process. Thus, in accordance with one embodiment, a silicone balloon is placed on the catheter between the treatment zone and the tissue to be protected (e.g., the outer sphincter). Inflating the balloon in the urethra substantially prevents excess acid and base from reaching the outer sphincter. While the balloon is inflated, a solution may be injected into the contained area (proximal of the balloon and generally in the treatment area) to dilute the acid or base in the contained area.

Returning to FIG. 35, first and second balloons 864 are provided on the catheter 860 to create a contained area therebetween. Fluid 866 in the contained area is substantially prevented from flowing past either balloon 864. The catheter may include at least one lumen 868 for transmitting a fluid (such as air or saline) from the proximal end of the catheter to the first and second balloons 866 (or lumen if only one is provided) to inflate the balloons. In some embodiments, the catheter 860 comprises a thin walled PEEK tube. The balloons 864 are sized for inflation within the vessel, are compatible with fluids naturally occurring in the vessel as well as by-products of the treatment, and are generally elastic to facilitate inflation. In one embodiment, the balloons 864 comprise a high durometer silicone rubber (e.g., 60 shore A durometer) with a thin wall (e.g., 0.25 mm). Fluid or other means may be transferred to the contained area to neutralize or decontaminate the fluid in the contained area. After neutralization or decontamination, the balloons may be deflated and fluid from the contained area permitted to pass. In one embodiment the distal balloon 864 is used for positioning of the catheter in the bladder neck.

In one specific embodiment, a system is provided for treating BPH and comprises a catheter and associated electrodes. The catheter is extended through the prostatic urethra to treat the prostate. Electrodes are deployed into the prostate. Treatment is done through the electrodes, with electrolysis producing acid and base. Where it is desired to prevent acid or base flow to other areas of the urethra, such as the outer sphincter, at least one balloon may be provided to block flow from the treatment area. Thus, a balloon is placed and inflated between the treatment area and the outer sphincter to contain the by-products of electrolysis for neutralization or decontamination. Once the process is completed and the fluid is neutralized, the balloon may be deflated and the catheter retracted.

Figure 36A:
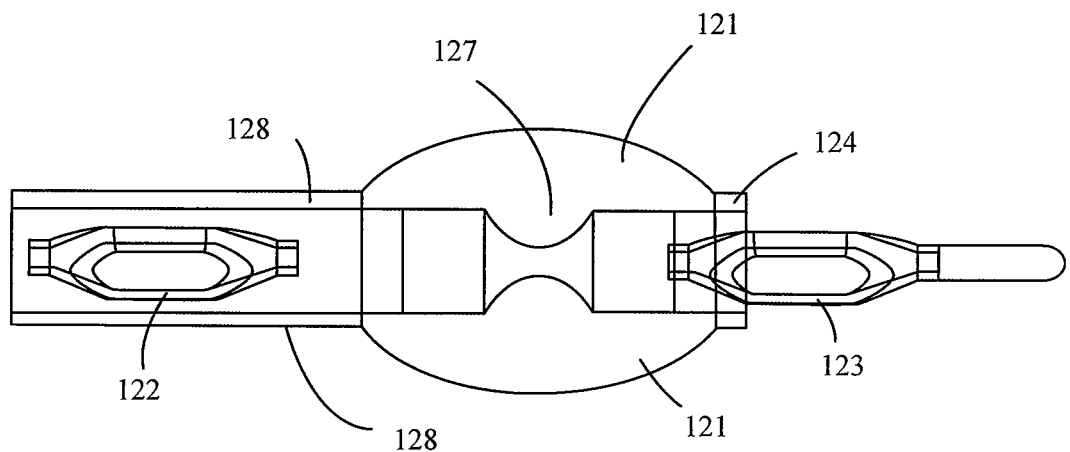
FIG. 36a illustrates a system including mechanical (airless) fixation anchors, with the anchors in a lengthened configuration, in accordance with one embodiment.
Figure 36B:
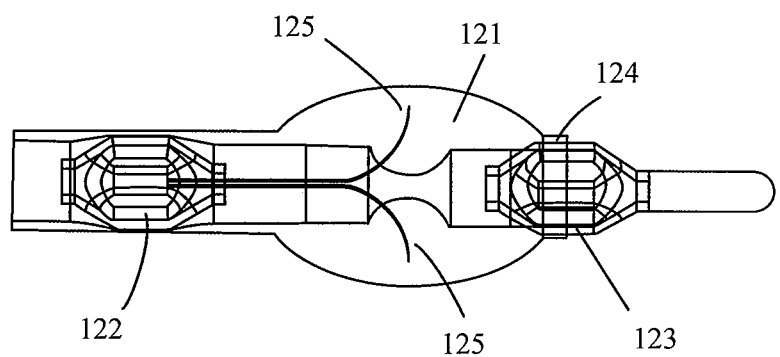
FIG. 36b illustrates the system of FIG. 36a with the anchors in an expanded configuration and the electrodes deployed.

In contrast to the embodiment of FIG. 35, FIGS. 36a and 36b illustrate a fixation device that permits fluid flow during treatment. FIG. 36a illustrates a side view with the fixation device in a lengthened configuration. FIG. 36b illustrates a side view with the fixation device in an expanded configuration. In the embodiment of FIGS. 36a and 36b, fixation devices (also referred to as mechanical anchors) 122 and 123 are provided for locking the catheter in place. The mechanical anchors may be referred to as airless anchors, indicating that they are not balloon anchors. FIGS. 36a and 36b illustrate anatomy of interest in treatment of BPH including lateral lobes 121 of the prostate, bladder neck 124, targeted treatment areas 127, and the urethra 128. FIGS. 36a and 36b further illustrate the first and second anchors 122 and 123, and the electrodes 125. The first and second anchors 122 and 123 expand and lock in place when shortened to anchor the catheter within the urethra, thus providing linear and rotational stability.

In one embodiment, the fixation device or anchor is a soft polymeric element. Generally, the fixation device may include channels in the expanded configuration that permit passage of fluid. As shown in FIG. 36a, the fixation device is provided distally of electrodes or other treatment mechanism. FIGS. 36a and 36b illustrates the fixation device having an extended length in the collapsed configuration. To expand the fixation device, the catheter portion may be slid forward, causing the fixation element to be compressed with a resulting larger diameter. This compression applies a retention force against the tissue in which the catheter is inserted. As shown in FIG. 36b, in one embodiment, in the expanded configuration, the fixation device includes first and second living hinges. The living hinges allow a fixation element to expand and contract freely as the proximal and distal ends of the fixation element are slid longitudinally along the catheter. The effect of this sliding is shown in FIG. 36a, in which the fixation element is forced into a smaller diameter cross-section by the movement of its ends. The smaller diameter facilitates implantation and extraction of the fixation element along with the catheter. In the embodiment shown, the fixation element comprises four anchor sections and four void channels permitting flow of fluids or gases. In alternative embodiments, more or fewer anchor sections and a corresponding number of void channels may be provided.

FIG. 36a shows components of the distal end of a catheter in a position adjacent to a prostate's lateral lobes 121. As shown, the targeted areas 127 of the prostate 121 have caused compression of the urethra 128. The first anchor 122 is positioned proximally on the catheter. The second anchor 123 is positioned distally on the catheter at the bladder neck 124. FIG. 36a illustrates the first and second anchors in a lengthened configuration.

FIG. 36b illustrates the first and second anchors 122 and 123 in an expanded configuration wherein their diameters have widened and their lengths have shortened. The electrodes 125 are deployed into the prostate 121. The first anchor 122 expands against the urethral wall to hold the catheter in place while the second anchor 123 maintains the distal tip of the catheter at the bladder neck 124. The first and second anchors 122, 123 are shortened and expanded via sleeves attached to the proximal end of the catheter. The electrodes 125 may be extended and retracted by any suitable means, for example using a set of internal sleeves attached to the proximal end of the electrode.

Figure 37:
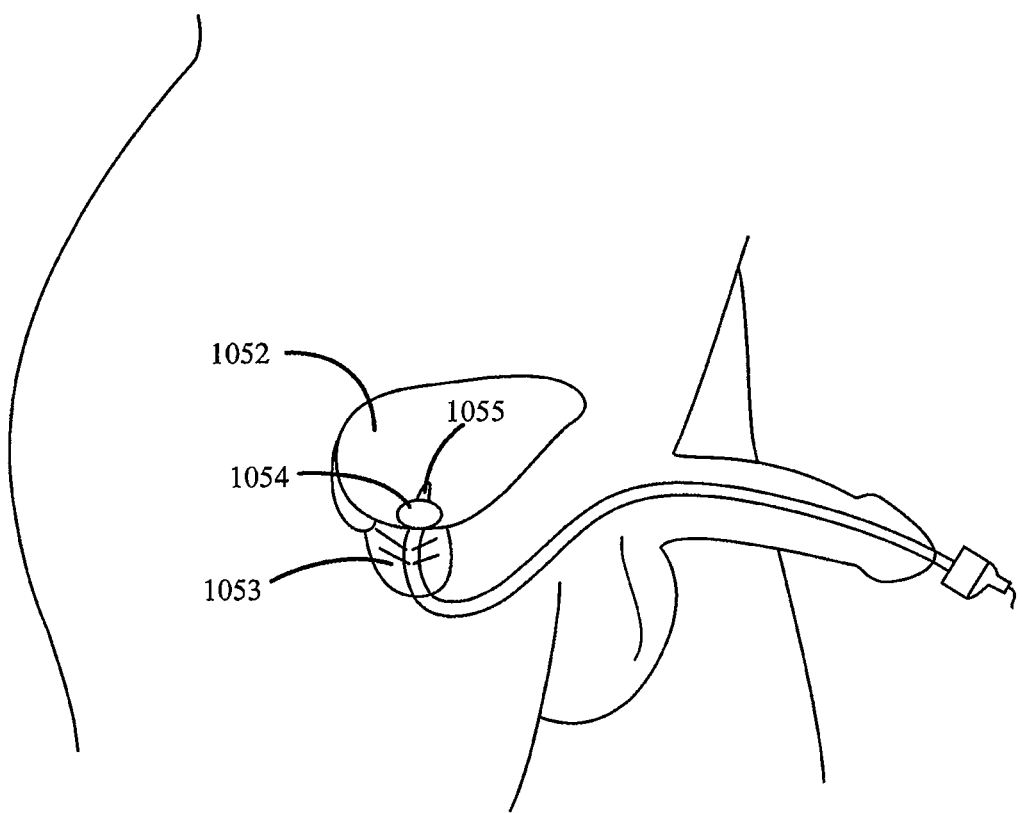
FIG. 37 illustrates a cross-section of the human male anatomy with a catheter in position with the fixation element activated and the electrodes deployed, in accordance with one embodiment.

FIG. 37 illustrates a cross-section of the human male anatomy with a catheter in position with a fixation element activated and the electrodes deployed, in accordance with one embodiment. The device is positioned using a distal balloon 1054 that is deployed from the distal tip 1055 and into the urinary bladder 1052 in FIG. 37. Once deployed to an appropriate size, the device is retracted until the balloon is seated in the neck of the bladder above the prostate 1053. In one embodiment, the distal balloon 1054 is silicone and has a low inflation pressure. Referring back to FIG. 33 when deflated, the distal balloon may have substantially the same shape as the tip and may be fit tightly to the tip. In one embodiment a small amount of silicone or fluoro-silicone mist or fluid may be placed on the inside surface of the balloon to keep the balloon from knitting together with the silicone tip. In the embodiment of FIG. 37, when the balloon 1054 is in a deflated state, the balloon 1054 covers only a portion of the tip 1055 and takes the same shape of the tip 1055 in the area that it covers.

As shown in FIG. 37, an air pressure pathway for inflation of the distal balloon 1054 may be provided through the center of the catheter. One embodiment of the pathway 1026 is shown in FIG. 24. Another embodiment has an air or fluid pathway to activate the fixation device along the inside wall of the inner sheath. One embodiment for the air or fluid pathway is a thin walled metal, titanium, or stainless steel tube. Another embodiment uses other semi rigid polymer materials such as PEEK or polycarbonate. Another embodiment uses a channel in a multiple channel polymer tube. Materials prone to kinking such as silicone or polyimide must be designed carefully to ensure that the fill tube does not kink during routing or electrode deployment.

While each of the balloons discussed herein is discussed with respect to air inflation of the balloon, it is to be appreciated that the balloon may alternatively be inflated using any fluid. For example, in an alternative embodiment a saline solution may be used to inflate the balloon. The balloon may be inflated with between 5 and 60 cc of fluid or air to ensure adequate anchoring in the bladder. One suitable volume of fluid is 15 cc of saline. If fluoroscopy or x-ray is used to image the position of the catheter in the body a radiopaque fluid may be used to fill the balloon. Any fluid in the balloon aids in the imaging of device position under ultrasound.

The balloon may be actively filled with fluid in any suitable manner. For example, the balloon may be filled with a syringe or bay attaching the line to a pneumatic or hydraulic pump. In some embodiments this pump is integrated into the DC ablation generator. The syringe or pump may be attached to the end of the fixation element fill line by the one way valve 1018, stop cock, or other valve as shown in FIG. 23. This allows fluid (saline or air) to be transported through the catheter and into the balloon to be filled.

Figure 38:
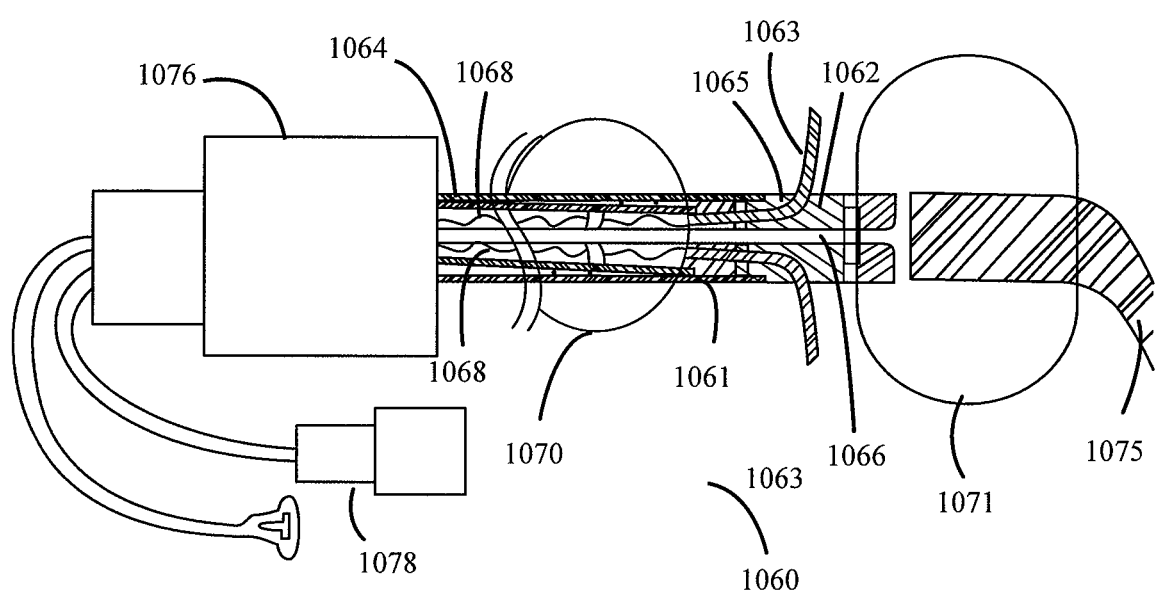
FIG. 38 illustrates a cross-section of a system showing detail of the distal end of a linear electrode deployment catheter, in accordance with one embodiment.

FIG. 38 illustrates an embodiment of a catheter 1060 with the proximal and distal balloons 1070 and 1071 inflated and the electrodes 1063 in a deployed configuration. The distal balloon 1071 is located proximate to the tip 1075 and is coupled to the tip 1075 of the catheter 1060. An electrical wire 1068 couples to each electrode and runs through the inner sheath 1064 and the handle 1076 of the catheter to the electrical connector 1078. The deflated proximal balloon 1070 is coupled to the outer sheath 1061 of the catheter 1060. The proximal balloon 1070 is positioned outside the proximal urinary sphincter and is of a greater length than the tip balloon 1071 so as to minimize any localized pain associated with its inflation.

The proximal balloon 1070 is coupled to the outer sheath 1061 of the catheter. In one embodiment, the proximal balloon 1070 may have a relatively long length to minimize patient discomfort associated with balloon inflation. For example, the proximal balloon 1070 may be approximately 5 cm long. Like the distal balloon 1071, the proximal balloon 1070 may comprise silicone and have a low inflation pressure. The positioning of the balloon is dependent on assuring that it is in the urethra but outside the external sphincter of the urethra. In one embodiment the catheter only has a distal balloon and the proximal balloon is omitted.

In some embodiments, the outer sheath comprises a flexible material capable of torque of, for example, approximately 11 Newton-meters (Nm). In a specific embodiment, the outer sheath comprises a composite material of a PTFE inner layer covered with a 0.13×0.25 mm 304 stainless steel wire braid, with a PEBAX outer coating. The PTFE provides an electrical insulator, a chemical barrier against by-products of ablation, and a low friction surface upon which the electrodes and O-rings can slide. In another embodiment, the outer sheath comprises a composite material of a PEBAX inner layer covered with a 0.05 mm diameter 304 stainless steel wire braid, with a PEBAX outer coating. The braid provides bi-directional torque-ability of the shaft. The PEBAX layer provides a good bonding surface, is resistant to the treatment byproducts, and provides a smooth surface interface with the tissue. The composite shaft thus may be flexible, bi-directionally torque-able, and chemically resistant. The outer sheath should have an outer diameter of 5.3 to 7.3 mm (16 to 22 Fr) for transurethral application such as ablating prostate tissue to treat BPH.

In some embodiments the outer sheath may have a lubricious coating (e.g. PTFE or other hydrophobic coating) over it to prevent trauma to the tissues during the insertion and removal of the catheter in the body's lumen. In some embodiments the outer sheath may have an aqueous antibiotic coating on it to prophylactically prevent an infection such as a urinary tract infection. In some embodiments the outer sheath may have an aqueous local analgesic coating (e.g. Lidocaine) to minimize discomfort or pain to patient during catheter insertion, removal, or placement in the body lumen (e.g. urethra).

FIGS. 39-42 illustrate portions of a handle for actuating the system for treating tissue. As may be appreciated, in a device, there are some parts of the device that directly control the activation, storage, orientation and deployment of the electrodes. Returning briefly to FIG. 38, the device includes electrodes 1063, a director 1062, inner sheath, 1064, an outer sheath 1061, a handle and the drive mechanism 1076.

The primary function of the electrodes 1063 is to make electrical contact with the tissue, and withstand the electrolysis process and its by-products. The function of the director 1062 is to assure the electrodes extend out from the device at the ideal location and direction. The outer 1061 and inner sheaths 1064 serve several functions. One of the functions is to control the movement of the electrodes 1063 in the director 1062, remotely from the handle 1076. Another function is to position the director 1062 at a pre-determined distance from the handle 1076 so that the electrodes have the capability of being placed in the right position. Another function is to control the rotational position of the director 1062 relative to the handle 1076. The outer and inner sheaths are conduits for electrical conductors 1068 and hydraulic/pneumatic lines 1066 between the handle 1076 and the director 1062, electrodes 1063, and fixation balloons 1070 and 1071. The outer sheath is generally smooth and shaped to assure patient comfort.

Figure 39:
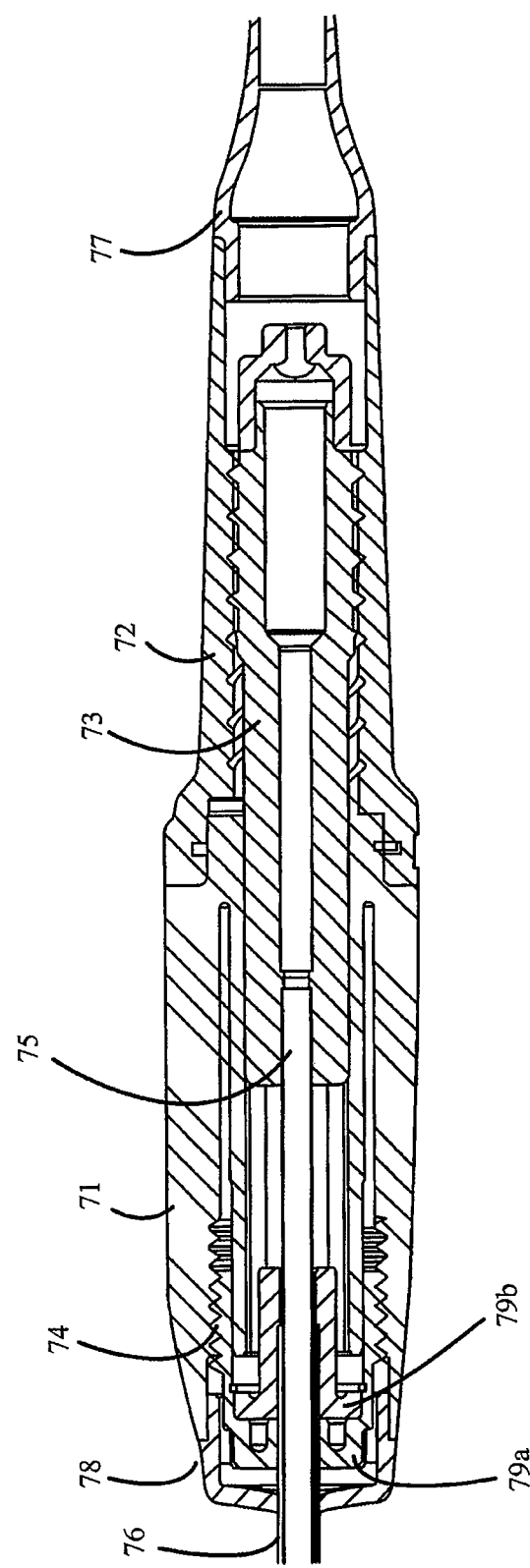
FIG. 39 illustrates a cross-section of a handle for linear deployment of electrodes, in accordance with one embodiment.

In one embodiment as shown in FIG. 39 the handle assembly 70 comprises of a handle dial 72 and handle grip 71 and serves as an anchor to the outer 76 and inner sheath 75. The relative and absolute movement of the outer and inner sheath is in relation to the movement of the handle pieces 72 and 71. In the embodiment shown, the outer sheath 76 is coupled directly to the handle grip 71. The inner sheath is coupled indirectly to the handle dial 72. If the handle dial 72 is rotated relative to the handle grip 71, then the inner sheath 75 moves axially within the outer sheath 76. The handle dial 72 is marked with indicators that indicate the length of extension of the electrodes, and the direction to rotate the dial to increase and decrease that extension. In one embodiment the handle grip 71 has a physical marker (e.g. marking or protrusion) that indicates the rotational position of the director.

In other embodiments the handle mechanism includes a lever, a trigger, or rotating part that causes the inner sheath 75 to move relative to the outer sheath 76 to deploy the electrodes. The handle mechanism provides the required mechanical advantage to deploy the electrodes with a low force that is easily able to be applied by the operator. If a rotary motion is required to deploy and retract the electrodes, or no mechanical advantage was required, then either a rotary or linear to rotary mechanism may be used. If a linear motion is required to deploy and retract the electrodes and no mechanical advantage was required, then a linear direct attachment slide may be used. If fine motion, accelerated motion, or mechanical advantage is required, then a rotary to linear mechanism may be used. The trigger mechanism can be a simple lever or a complicated, spring activated, lever or rotational to linear motion device. In another embodiment, there may be a mechanism for winding up a spring which deploys the electrodes at an accelerated rate when the spring is released using a trigger mechanism. In one embodiment the handle may be built around or integrated with the mechanism. If the mechanism uses a lever for activation, then a slot may be provided in the handle for accommodating the lever. If the mechanism uses a rotational to -linear motion, then a portion of the handle may be configured to rotate. In one embodiment of the handle, a linear piston is used to move the inner sheath axially within the outer sheath. In one embodiment of the handle, a gear that converts the rotational motion to linear motion is used to move the inner sheath within the outer sheath and provide mechanical advantage.

Devices that use a linear movement to activate the electrodes generally create a linear motion at the handle. In one embodiment, the linear motion may be provided with a direct attachment to the inner sheath. In one embodiment, the linear motion may be provided with a lever that is attached to the inner sheath and that can provide either a multiplication in speed or mechanical advantage to the movement of the electrodes. In one embodiment, the linear motion may be provided with a trigger mechanism. In one embodiment, the linear motion may be provided with a rotation to linear gearing mechanism. Other embodiments may use pneumatic or hydraulic fluids to actuate and move the inner sheath or the electrodes directly.

Figure 40:
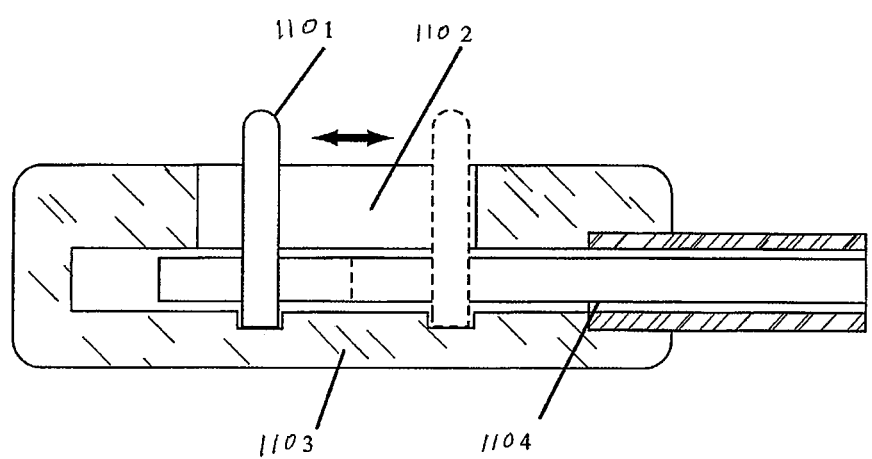
FIG. 40 illustrates a direct attachment mechanism of a handle for linear deployment of electrodes, in accordance with one embodiment.
Figure 41:
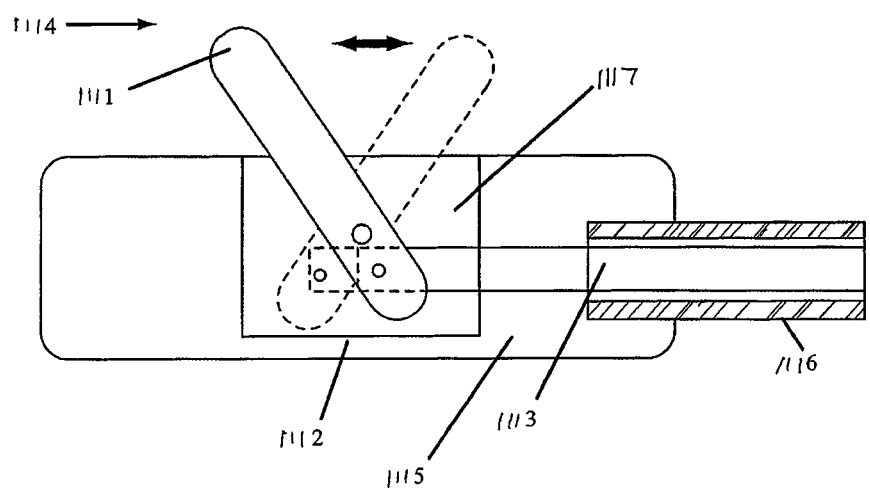
FIG. 41 illustrates a lever mechanism of a handle for linear deployment of electrodes, in accordance with one embodiment.

FIG. 40 illustrates a direct attachment mechanism of a handle for linear deployment of electrodes, in accordance with one embodiment. The linear motion can be provided with a direct attachment to the inner sheath. As shown in FIG. 40, a tab 1101 or part of the handle 1103 is directly coupled to the inner sheath 1104. The tab 1101 follows a groove 1102 in the handle 3 to prevent rotation of the inner sheath 4 during its activation. This is the simplest mechanism and works best for a device with a set deployment and retraction position. FIG. 41 illustrates a lever mechanism of a handle for linear deployment of electrodes, in accordance with one embodiment. As shown, the lever 1111 is attached to a fulcrum 1112. The lever may be any of the three basic types of levers (e.g. first class, second class, or third class). The level of mechanical advantage and rate of activation is determined by the position at which the fulcrum 1112 and inner sheath 1113 is attached to the lever 1111 and where the force 1114 is applied to the lever 1111. The activation of the lever 1111 within a cavity 1117 in the handle 1115 causes the inner sheath 1113 to move axially relative to the outer sheath 1116 and handle 1115. The difference between the lever and direct attachment methods is that the lever can provide either a multiplication in speed or mechanical advantage to the movement of the electrodes. This mechanism provides some advantage over the direct attachment, but still is best for a device with a set deployment or retraction position.

Figure 42:
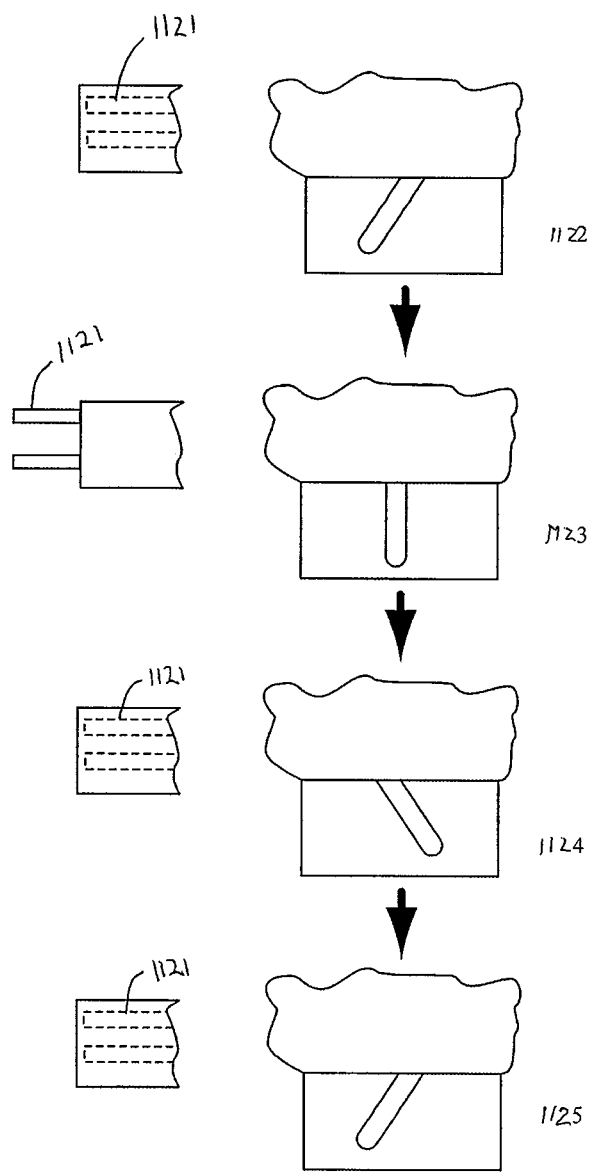
FIG. 42 illustrates an actuation sequence for a trigger mechanism of a handle for linear deployment of electrodes, in accordance with one embodiment.

FIG. 42 illustrates an actuation sequence for a trigger mechanism of a handle for linear deployment of electrodes, in accordance with one embodiment. As shown, the electrodes are deployed or retracted using a trigger mechanism. The trigger mechanism can be a lever as described in FIG. 42 or can be a more complicated mechanism that extends the electrodes 1121 when the trigger is pulled to one position 1123 and automatically resets the electrodes to a retracted position 1124 at the completion of the trigger motion 1125. In one embodiment there may be a positive, locking stop when the electrodes are extended to the desired extension. To finish the motion, the trigger may be unlocked and the trigger motion completed. This type of mechanism can have the advantage of faster deployment, some mechanical advantage, and automatic retraction of the electrodes.

Returning now to FIG. 39, discussion will be made of the rotation to linear gearing. In one embodiment as shown in FIG. 39 a rotation to linear gearing mechanism within the handle is used to deploy and retract the electrodes. The advantage of a rotation to linear gearing mechanism is that precise mechanical advantage can be achieved while making precision fine adjustment to electrode deployment length. In one embodiment, a threaded piece 73 is attached to the inner sheath 75. The threaded piece 73 is surrounded by the handle dial 72. The handle dial 72 has an internal thread to match and engage the thread of the threaded piece 73. The threaded piece 73 acts as a follower to the handle dial 72, moving axially within the handle dial 72 when it is rotated. The threaded piece is keyed to a feature in the handle grip 71 which it slides within to prevent the threaded piece 73 from rotating with the handle dial 72. Preventing the rotation of the threaded piece 73 is the key to the mechanism used in converting the rotational motion into axial motion. It also prevents the rotation of the inner sheath 75 and accordingly the electrodes within the distal tip. The handle dial 72 and grip 71 are held together and allowed to rotate relative to one another with a feature such as a retaining ring, snap fits, or pins. The thread pitch can be set to give the maximum linear motion required for a given amount of rotation. In one embodiment, the thread pitch allows 24.5 mm of travel for one rotation. Another embodiment of this mechanism is a set of "stop" features that create a positive stop for maximum deployment and for retraction of the electrodes. In one embodiment of the "stop" feature, the feature is made up of a radial groove that stops after 330 degrees of rotation and is located in one of the handle pieces. In one embodiment, the stop features and radial grove are in the handle dial 72. A follower, located in the handle grip 71, extends out from the handle surface with a matching length, diameter, and radius to the "stop groove". The follower allows the handle grip to rotate around the handle dial to a specific rotation and stop or vice versa. It is obvious that this set of "stop features" has to be aligned with the other features of the handles that are related to the rotation (location of the stop, location of different length indicators, and the direction of rotation. Without these positive stops, the operation of the device can over-stress joints leading to device failure.

Intermediate "stops" can be added to align with different extension indicators. In one embodiment the intermediate stops are added with the use of a spring plunger in the follower and dimples in the bottom of the "stop groove". As the follower revolves around the "stop groove", the plunger falls into a dimple, causing it to stop. As the handle is further rotated, the spring of the plunger allows the plunger to retract and the follower move to the next "stop" feature.

This embodiment of the stops is suitable when the thread pitch can be adjusted to give the required linear motion in less than one rotation (for instance 330 degrees of rotation). If more than one rotation is required then additional sets of "stop features" and parts can be added. Once the maximum rotation is reached on one "stop feature", another "stop feature" is engaged. This continues until the maximum rotation is achieved. Different spring plungers, each with higher spring forces, can be used in each new succeeding layer of "stop features". This forces the first stop feature to finish rotating before the second "stop feature" starts to rotate. This is only important if there are intermediate stops on one of the "stop feature" layers.

Another mechanism involves the use of pneumatic or hydraulic fluids to actuate and move the inner sheath or the electrodes directly. In this embodiment, a cylinder and plunger mechanism would move linearly through the use of pressurized pneumatic (air) or hydraulic fluids (water or other non-compressible fluid). The cylinder could be in the handle of the device, moving the inner sheath back and forth to deploy or retract the electrodes. The cylinder could be inside the distal end of the outer sheath, extending or retracting the electrodes from that position in the device. There could be individual cylinders for each electrode or for groups of electrodes. One advantage to this type of mechanism is that each electrode or sets of the electrodes could be individually controlled. Another advantage is that a large mechanical advantage can be achieved with pneumatic or hydraulic designs. Another advantage is that the increased speed of electrode deployment and retraction that can be achieved.

In other embodiments, rotational deployment of electrodes is used. Devices that use a rotational movement to activate the electrodes generally create a rotational motion at the handle. This rotational motion can be provided with a direct attachment to the inner sheath.

Figure 43:
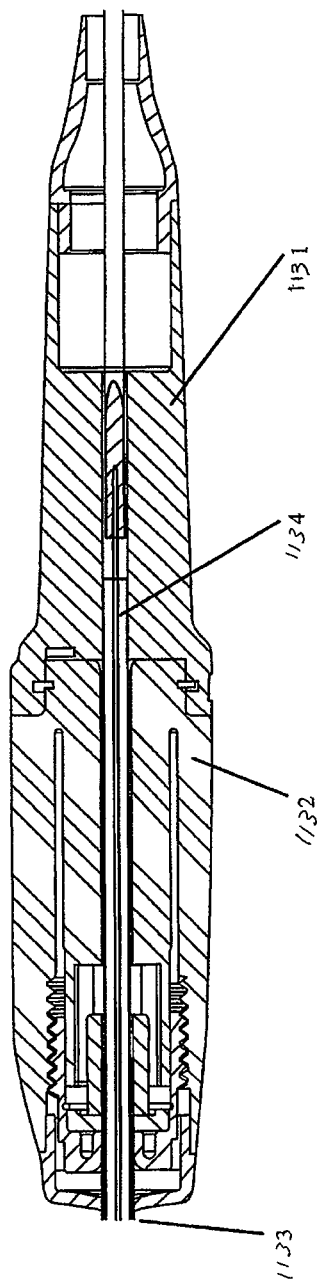
FIG. 43 illustrates a cross-section of a direct attachment mechanism of a handle for rotational deployment of electrodes, in accordance with one embodiment.

FIG. 43 illustrates a cross-section of a direct attachment mechanism of a handle for rotational deployment of electrodes, in accordance with one embodiment. As shown, rotational motion can be provided with a direct attachment of the handle dial 1131 to the inner sheath 1134. The handle grip 1132 would be attached to the outer sheath 1133. The handle dial 1131 would be attached to the handle grip 1132 by a feature such as a retaining ring or a snap feature that the two handle parts could not move linearly with respect to each other, but could rotate relative to each other. As in a lever, some mechanical advantage can be achieved by increasing the handle diameter. The greater the ratio between the handle dial diameter and the spool diameter, then the greater the mechanical advantage.

The same embodiment of a mechanism for a "stop" feature and intermediate stops in the rotational to linear gearing embodiment applies for the direct attachment rotational embodiment as shown in FIG. 43.

In further embodiments to the mechanisms discussed above, the mechanisms may be modified with a spring mechanism that is "cocked" or 'wound-up" and set. This mechanism may speed the deployment of the electrodes leading to a single fast "stick" instead of slow penetration. This single "stick" may provide more comfort to the patient during the deployment of the electrodes. This addition to one of the mechanisms may also make the insertion process easier and more complete, forcing the deployment to the stop.

In any of the systems described above, independent control of electrodes can be added allowing deployment of some electrodes and not others or deploying the electrodes to different, adjustable lengths. This is done by duplicating existing design components and giving them additional degrees of freedom of motion. The advantage of this is the ability to tailor the device treatment to the specific tissue configuration. The handle either is part of the mechanism or houses and interacts with portions of the mechanism. The handle is the interface between the operator (physician) and the mechanism. The material, shape, indicators, and labeling provide comfort in handling and operation, and intuitive instructions for use to the operator, often determining the success or failure of the product.

Figure 44:
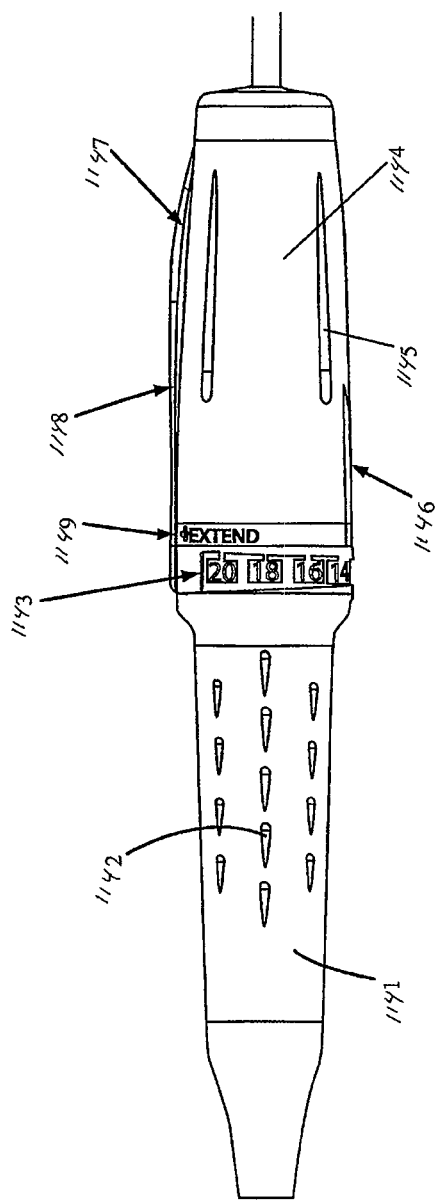
FIG. 44 illustrates external features of a catheter handle, in accordance with one embodiment.

In one embodiment as shown in FIG. 44, the handle dial 1141 (proximal end of the device) is tubular in shape and fits easily in a medium sized human hand. It has aesthetic features 1142 that also improve the handle ergonomics. The markings 1143 on the handle dial indicate the electrode deployment length and full retraction position. The handle is made from ABS, polycarbonate or similar type of plastic that is a general grade of medical device plastics. It has a relatively low coefficient of friction, but is relatively strong, bonds well with adhesives, can be easily colored, and is compatible with general surgical situations and chemicals.

Figure 45A:
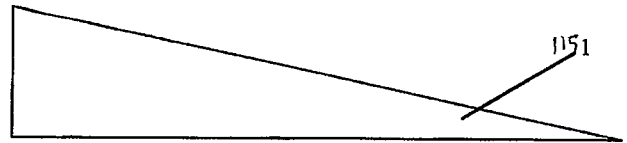
FIG. 45a illustrates a first embodiment of a visual line indicator for indicating the deployment length of the electrodes.
Figure 45B:
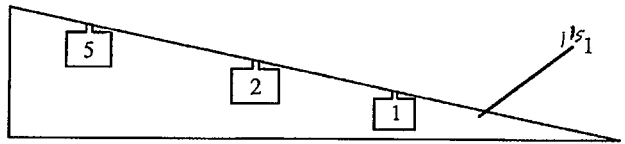
FIG. 45b illustrates a second embodiment of a visual line indicator for indicating the deployment length of the electrodes.
Figure 45C:
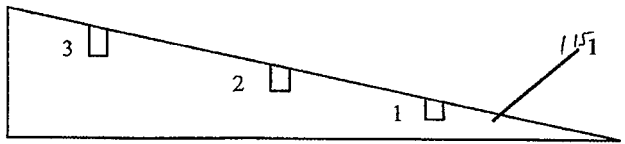
FIG. 45c illustrates a third embodiment of a visual line indicator for indicating the deployment length of the electrodes.

In the embodiment as shown in FIG. 44, the handle grip 1144 (distal end of the device) is tubular in shape and fits easily in a medium sized human hand. It has aesthetic features 1145 that also improve the handle ergonomics. It has a flat feature 1146 to prevent the device from rolling off a table. It has an extruded feature 1147 from the top which indicates the rotational top-center of the device and electrode deployment. In some embodiments the extruded feature 1147 also includes a printed marking 1148 to further indicate the top-center of the device. The markings 1149 on the handle grip 1144 indicate the direction of rotation to achieve deployment or retraction, a line on the top of the protrusion indicating the top center, and the device logo. FIGS. 45a-45c illustrate embodiments of a visual line indicator for indicating the deployment length of the electrodes.

As shown, the indicator 1151 for increasing the deployment length is a continuously enlarging line indicator. This gives the operator the impression of a continuously increasing deployment length instead of discrete steps of increasing length. The advantage of using this type of indicator is that it provides the operator with a different type of intuitive instruction for use.

An alternative to the use of the line and extrusion as the visual indicator for top-center is the use of a bubble level indicator located in their place or in addition to them. The bubble of the level indicator appears when the handle is rotated with the top-center up. This is a very good visual indicator. The bubble indicator may be placed on the top surface of the handle grip.

In one embodiment the catheter has the ability to be adjusted or calibrated to assure that the electrode deployment length was the same as what the dial mark on the device displayed. In one embodiment as shown in FIG. 39 the device can adjust the length of the outer sheath 76. The adjustment is done at the end of the assembly by rotating a threaded first adjuster piece 79a. In order for this adjuster piece to rotate freely without rotating the outer tube, a second adjuster piece 79b is added to the inside of the first adjuster piece. The second adjuster piece 79b is permanently bonded to the outer sheath 76 and has features that mate with the handle grip 71 to prevent the second adjuster piece 79b (and the outer sheath 76) from rotating. The second adjuster piece 79b is attached to the first adjuster piece 79a in a way that allows rotation, but retains the relative positioning. The retention method may include a retaining ring or snap features. As the first adjuster piece 79a is turned into the threads on the handle grip 71, the outer sheath 76 is effectively shortened, increasing the deployed electrode length. This feature can be fixed in place in any suitable manner such as using glue, thread-locker, or physical feature such as a set screw. The method of fixing its position generally may be reversible to facilitate the emergency field procedure for removing the electrodes after a handle or bond failure in the field.

In one embodiment, a unique wrench is provided to access the nut on the first adjuster piece 79a as shown in FIG. 39 and enable it to be unscrewed. The wrench features include a gap in the hex portion of the wrench to enable it to go over the outer sheath from the side, and a deep extension of the hex that allows it to reach down into the end of the handle grip 71 to enable adjusting the position of the first adjuster piece 79a.

In one embodiment, the handle incorporates lubrication between moving parts to prevent wear and ensure a smooth action of motion. In one embodiment, silicone based grease is used between moving parts. In another embodiment, a lubricous material such as Delrin or PTFE is used in the areas where moving parts are in contact. Another embodiment includes selectively coating the involved surfaces of the parts with a lubricous coating (PTFE or Parylene or a similar type material.). This allows the base parts to have low friction in the coated areas and good bonding properties in the uncoated areas. The method for selective coating includes masking the parts where the coating is not wanted. This can be done with masking tape or specific tooling. The coating is then applied as a plasma vapor in a plasma deposition chamber. The masking can then be removed.

The assembly of the device as shown in FIGS. 38 and 39 is simplified by assembling the inner core including the inner sheath 75 of FIG. 39, the Electrode-Driver Assembly of FIG. 38 (which includes electrodes 1067, the driver 1065, and electrical conductors 1078), Threaded Piece 73 of FIG. 39, Fill Tube Assembly 1066 of FIG. 38, and the electrical cable and connector 1078 of FIG. 38. This allows the core pieces of the device to be assembled, verified, and reworked if needed, prior to adding the handle pieces and outer sheath and adjuster pieces. To finish the assembly, the handle dial 72 of FIG. 39 is assembled onto the thread, the handle grip 71 is assembled over the threaded piece 73 end, and the two handle pieces are locked together using a retaining ring. The outer sheath 76 is bonded into the second adjuster 79b, and the second adjuster piece 79b is locked into the first adjuster piece 79a with a retaining ring. The outer sheath and adjuster pieces are assembled over the inner sheath 75, and onto the handle grip 71. The director 1062 of FIG. 38 is assembled onto the electrodes and bonded to the outer sheath 1061. The fill Tube end 1066 and the tip/balloon 1075 and 1071 are bonded onto the director 1066. The electrode deployment length is calibrated to the indicator, and the end caps 77 and 78 of FIG. 39 are put in place.

Other embodiments include using snap fits or other methods for joining pieces together in position, while allowing them to rotate freely. These would be used specifically in joining the handles, the adjuster pieces, and possibly the end caps.

In another embodiment the handle grip and dial can be molded as two pieces (split along the length) and assembled together using adhesive, screws, or snap fits over the end of the other handle piece to eliminate the use of that retaining ring or other joining method.

Figure 46A:
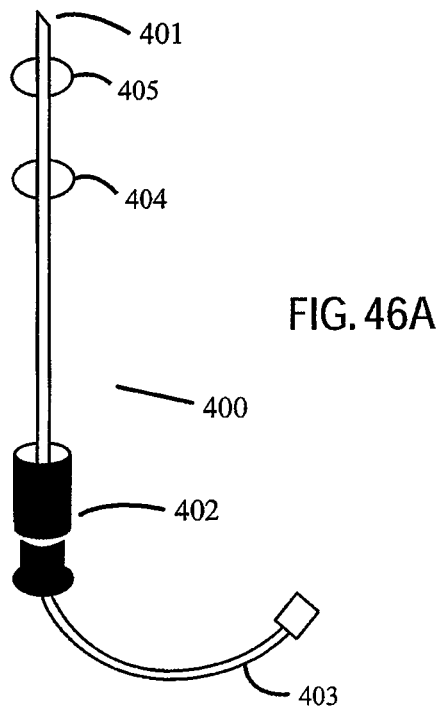
FIG. 46a illustrates a catheter with fixation balloon activated and electrodes retracted, in accordance with one embodiment.
Figure 46B:
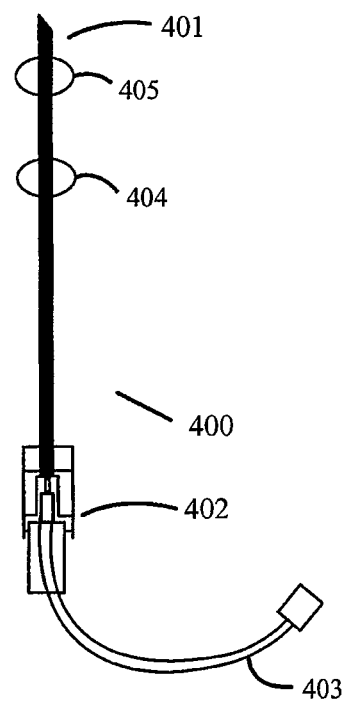
FIG. 46b illustrates a cross-section of a rotational electrode deployment catheter with the fixation balloons activated and the electrodes retracted, in accordance with one embodiment.

FIGS. 46a-46b illustrate yet a further embodiment of a system for treating tissue including a spool upon which the electrodes are wound for rotation deployment of the electrodes. The device for BPH treatment is designed to be inserted through the urethra until the distal end of the device is in the bladder. It is to be appreciated that modifications will be obvious to those skilled in the art to modify the embodiment of FIGS. 46a-46b for treatment of other tissues. In the embodiment shown, a distal balloon is inflated and the device is retracted into treatment position. A proximal balloon is inflated to hold the device in position and prevent the device from rotating while the electrodes are deployed. The electrodes are deployed by rotating an inner spool and unwinding the electrodes from the spool. As the spool is rotated, wires wrapped around the spool are deployed through routing holes in an outer sheath of the device. The ends of the electrodes may be un-insulated, may comprise a material resistant to electrochemical corrosion, and may have adjustable positions relative to the urethra, thus controlling the position and size of the treatment zone. When the treatment is completed, the electrodes are retracted by winding the electrodes onto the spool, the balloons deflated, and the device removed.

Figure 46C:
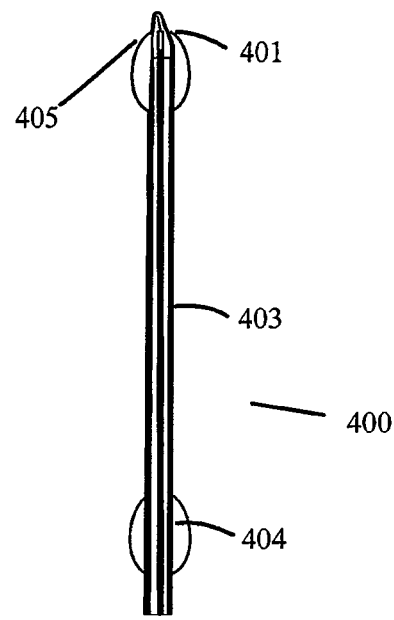
FIG. 46c illustrates a cross-section of a catheter with two fixation balloons activated, showing the fill tube that supplies fluid to activate and deactivate them, in accordance with one embodiment.
Figure 46D:
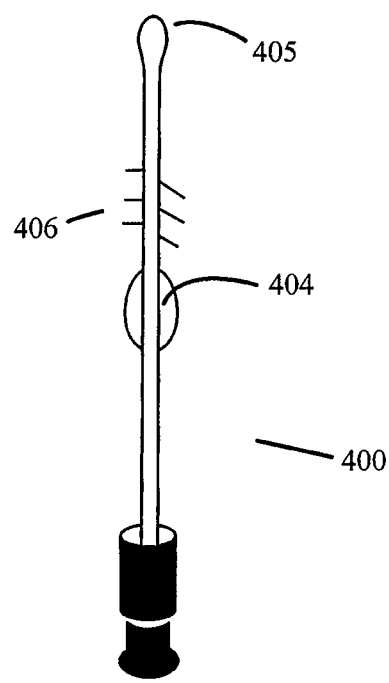
FIG. 46d illustrates a rotational electrode deployment catheter with the fixation balloons activated and the electrodes deployed, in accordance with one embodiment.
Figure 46E:
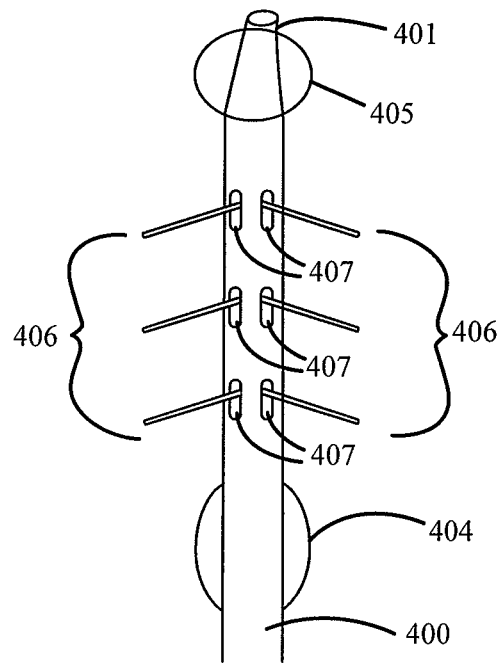
FIG. 46e illustrates the distal end of a rotational electrode deployment catheter with the fixation balloons activated and the electrodes deployed through director channels cut into the catheter wall, in accordance with one embodiment.
Figure 47:
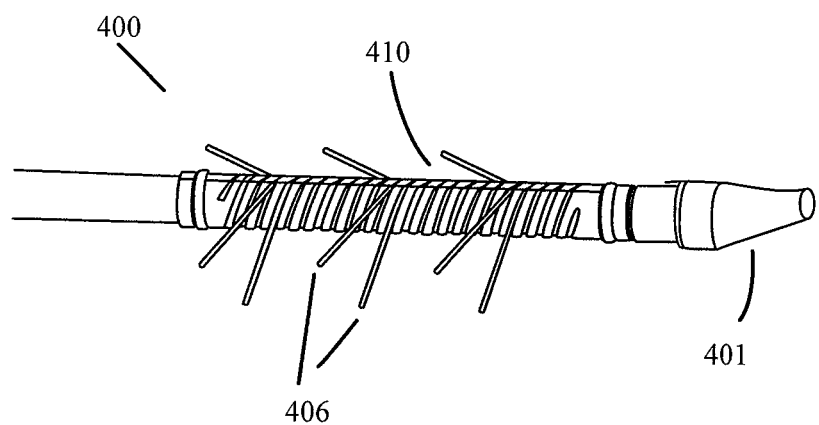
FIG. 47 illustrates the distal end of a rotational electrode catheter with the outer sheath removed and the electrodes deployed, in accordance with one embodiment.
Figure 48:
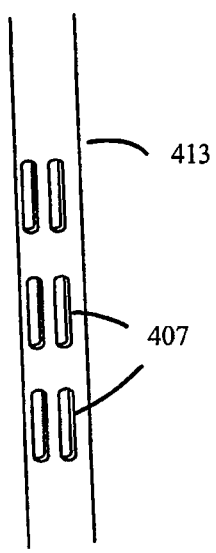
FIG. 48 illustrates a close-up of the distal end of the outer sheath of a rotational electrode catheter showing the director holes cut in the sheath, in accordance with one embodiment.
Figure 49:
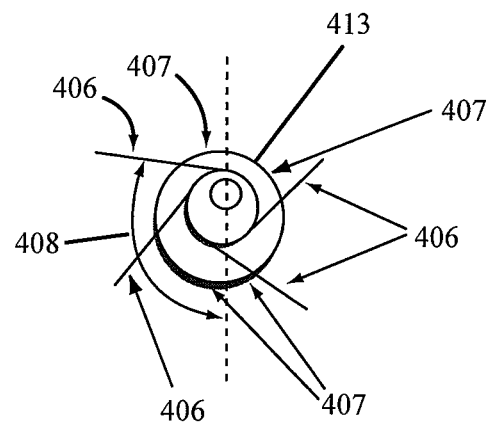
FIG. 49 illustrates an end view of a rotational electrode deployment catheter with the electrodes deployed, in accordance with one embodiment.
Figure 50:
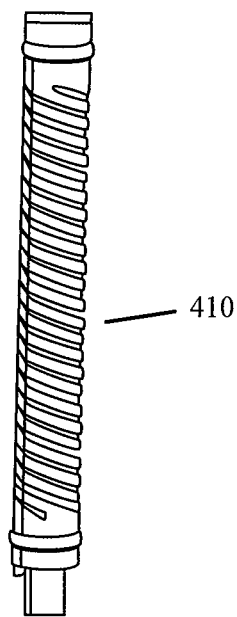
FIG. 50 illustrates the spool of a rotational electrode deployment catheter assembled with o-rings, one on each end, in accordance with one embodiment.
Figure 51A:
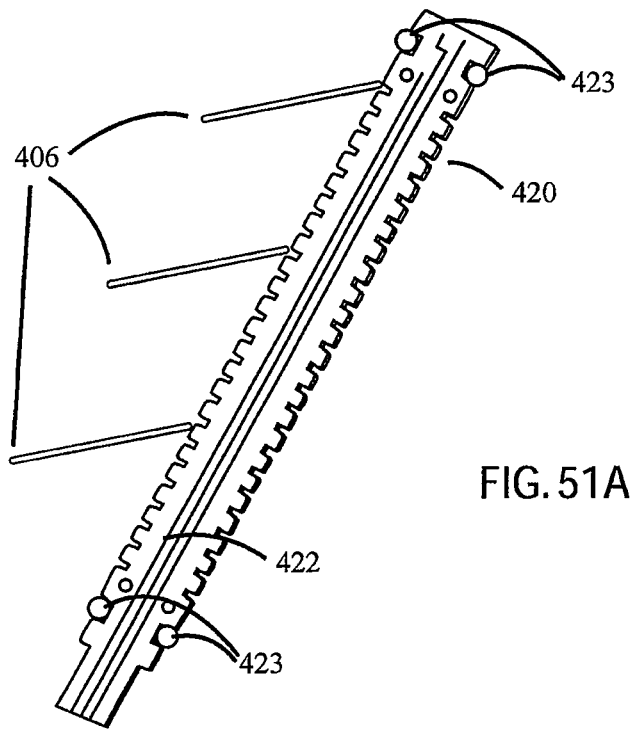
FIG. 51a illustrates a half of a rotational electrode deployment catheter spool, in accordance with one embodiment.
Figure 51B:
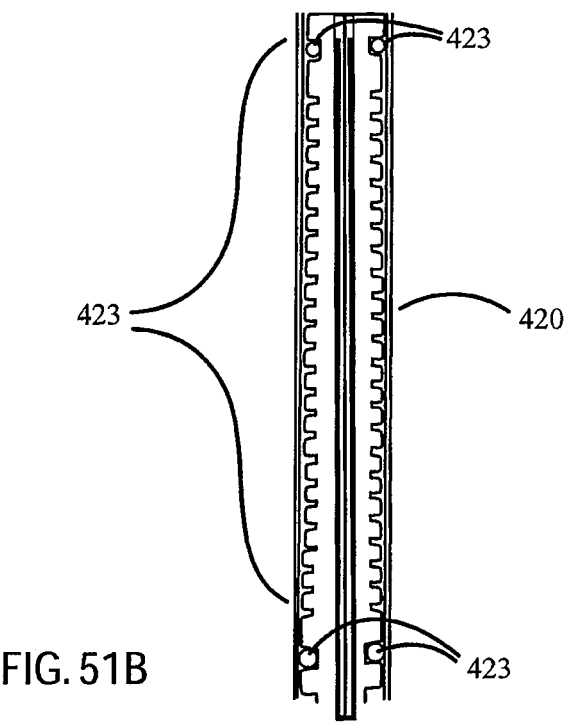
Figure 52:
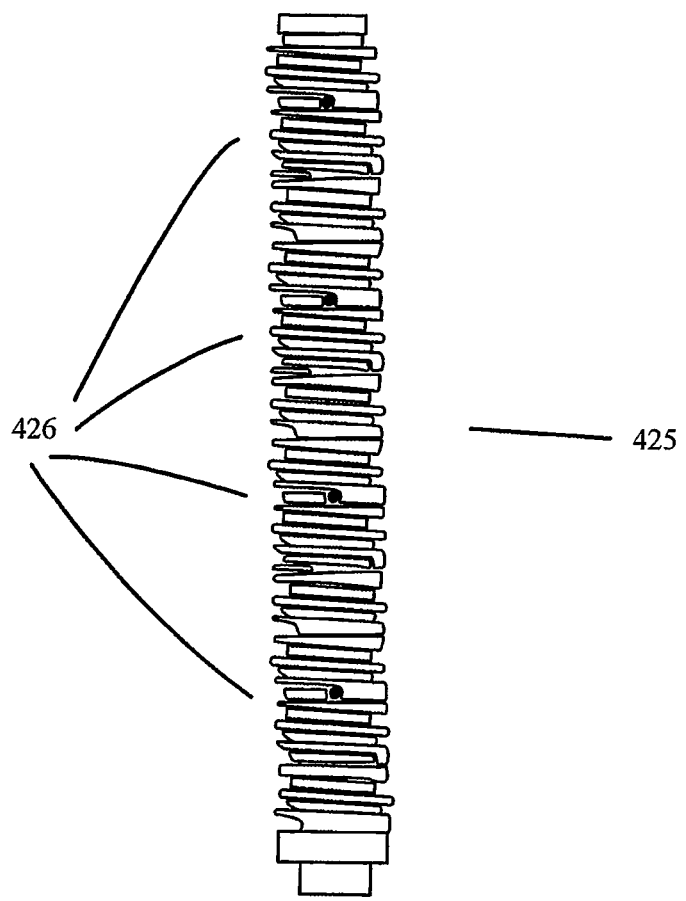
FIG. 52 illustrates another embodiment of a rotational electrode deployment catheter spool having a single start helix for each of the 12 individual spools that comprise the whole spool.
Figure 53:
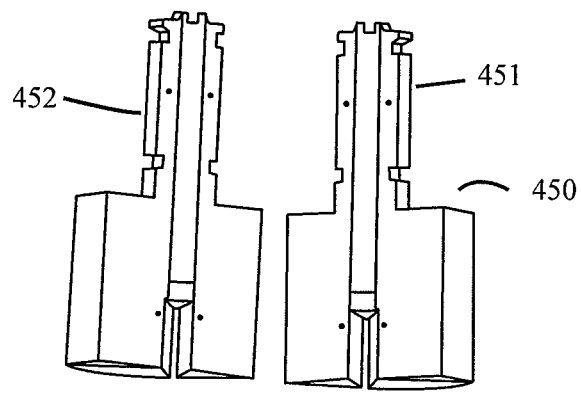
FIG. 53 illustrates two halves of a spool winding tool for a rotational electrode deployment catheter, in accordance with one embodiment.
Figure 54:
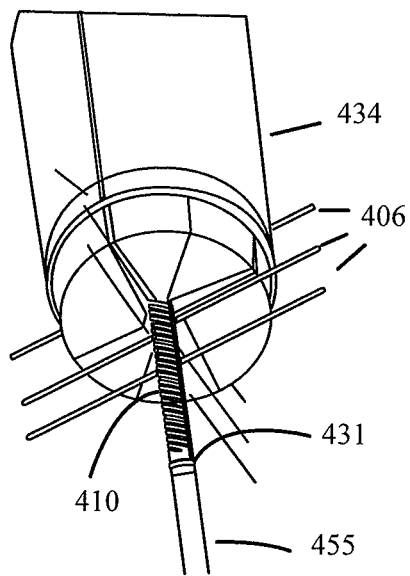
FIG. 54 illustrates a view of the assembled winding tool of FIG. 53 winding electrodes onto a spool, in accordance with one embodiment.
Figure 55:
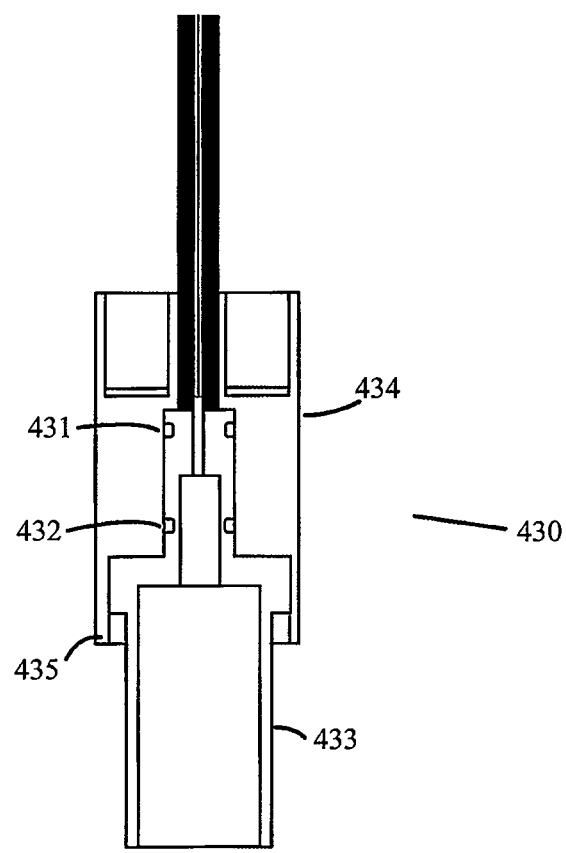
FIG. 55 illustrates another embodiment of a handle assembly for the rotational electrode deployment catheter.
Figure 56A:
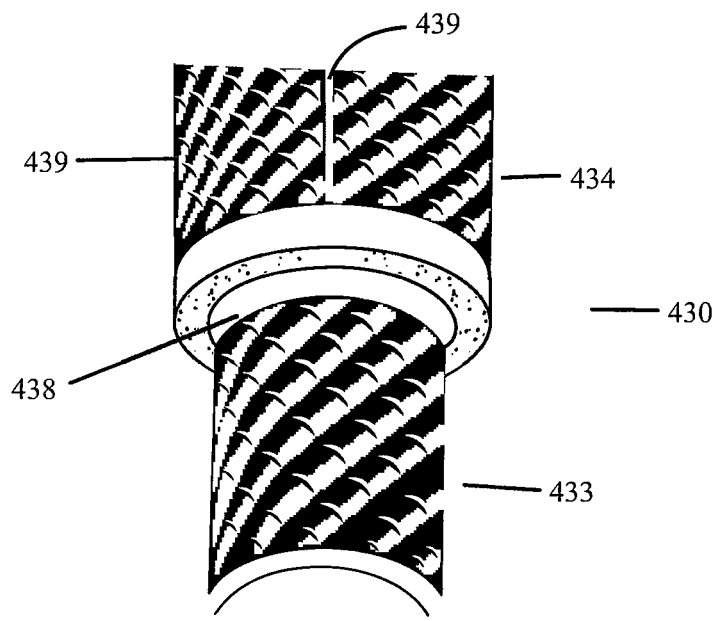
FIG. 56a illustrates a dial indicator on a handle dial and a rotational indicator line on a grip, in accordance with one embodiment.
Figure 56B:
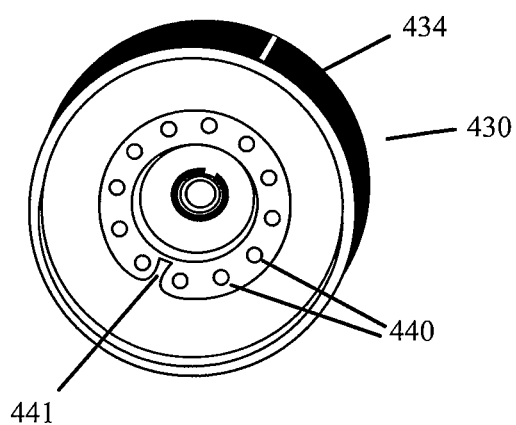
FIG. 56b illustrates a groove in which the stop extension of the handle dial rotates, and in which there are absolute stops and dimples for intermediate stops, in accordance with one embodiment.

FIGS. 46a-46b illustrate a catheter 400 having a tip 401 and a handle 402. FIGS. 46a and 46b illustrate the device generally. The distal end of the catheter 400, including a distal balloon 405, electrical wire 403, and proximal balloon 404, is shown in FIG. 46c. FIGS. 46d and 46e illustrate electrodes 406 and positioning holes 407. FIG. 47 illustrates a spool 410 with the electrodes 406 wrapped there around. Element number 410 is used to refer to a generic spool, regardless of configuration. FIG. 48 illustrates routing holes 407 in an outer sheath 413. FIG. 49 illustrates an end view of the device. FIGS. 50, 51a, and 51b illustrate alternative spool embodiments. FIG. 50 illustrates an exemplary spool 410. FIGS. 51a and 51b illustrate a cross section of the spool 420, electrodes 406, conducting wire 422, and o-ring seals 423. FIG. 52 illustrates a composite spool 425 comprising a plurality of individual spools 426. FIG. 53 illustrates a winding tool 450 comprising two parts 451 and 452 for wrapping electrodes around a spool 410 of FIG. 54. FIG. 54 illustrates the use of the winding tool 434 for winding the multitude of electrodes 406 onto the spool 410 of an assembly 455. FIG. 55 illustrates a handle 430 comprising o-ring seals 431, 432, an inner handle (also referred to as inner hub) 433, an outer handle (also referred to as outer hub) 434, and a retaining ring 435. FIG. 56a illustrates the inner handle 433 and outer handle 434 as well as indicator ring 438, indicating the length of electrode extension, and cursor 439. FIG. 56b illustrates an end view of the outer handle 434 of 430, showing intermediate stops (depressions) 440, and the stops 441 for maximum extension and retraction.

In some embodiments, the tip 401 as shown in FIG. 46e may have a tapered shape and seals to create an O-ring seal on the outer sleeve of the catheter body used for conducting pressure from the inside of an inner shaft of the catheter 400 to the distal balloon 405. The tapered tip is thus attached to the outer sheath and an inner fill tube. This attachment substantially prevents rotation of the tip relative to the outer sheath and airflow from the inner fill tube. The inner fill tube may be, in some embodiments, stainless steel, and is provided within the inner sheath. The O-ring blocks air flow between the tip and the channel between the inner and outer sheaths. The distal tip is made of a low durometer silicone (30 to 80 Shore A durometer) and tapered and may include an upward curve to mimic a Coude tip for easy access along the urethra.

As shown in FIG. 46e, the distal balloon 405 inflates and is then used for locating the device in the bladder neck. The proximal balloon 404 inflates to approximately the size of the urethra to hold the linear and rotational position of the device in the urethra. The electrodes 406 extend through positioning holes 407 that direct the electrodes at a desired angle. In one embodiment 3 or 4 rings of 4 electrodes each are provided. The electrodes may be typically spaced, for example, 1 centimeter apart with one row angled up to both sides at a 15° angle to the horizontal (assuming positioning line is up). Further, one row may be angled down at 40° on both sides. An exemplary embodiment has the anterior electrodes 8 mm apart with the electrodes at 0 degree angle to the horizon and the posterior row angled down at 35 degrees into both lobes of the prostate.

FIG. 47 illustrates the spool 410 with the electrodes 406 wrapped there around. As may be appreciated from FIG. 48, the holes 407 in the outer sheath 413 are positioned to provide a desired angle of electrode extension relative to the steering handle alignment line. FIG. 49 illustrates the outer sheath 413 with the electrodes 406 extending out of the routing holes 407. The electrodes 406 extend at a 90° angle 408 to the outside diameter of the spool.

During the deployment of the electrodes, the outer sheath is stationary, while the inner spool or sheath rotates and the electrodes are directed out of the routing holes in the outer sheath. Generally the catheter comprises an outer sheath and an inner sheath. Each of the inner and outer sheaths may be configured to be flexible and also to be resistant to bi-directional torque. Additionally, at least for the outer sheath, it may be desirable that the sheath be chemically resistant. Various embodiments of catheters are shown and described in copending U.S. patent Ser. No. 12/544,134, herein incorporated by reference in its entirety.

As shown and discussed with respect to FIG. 49, the outer sheath 413 is provided with routing holes 407 for each electrode. The routing holes 407 may be provided in the outer sheath 413 in any suitable manner. For example, the routing holes 407 may be LASER cut or etched in the outer sheath 413. The position of each hole 407 along the length of the outer sheath 413 may be determined by the length of the electrode, the spacing between the rings of the electrodes, and the final relative position of the spool within the outer sheath 413. Each hole 407 comprises a length and a width. The length of each hole 407 may be determined by the maximum exposed length of the electrode. The width of each hole may be calculated by the desired angle of the electrode as it exits tangent to the outer edge of the spool 410. The angular position of each row of holes may be determined by determining a desired angle of deployment and rotating that angle approximately 90° in the opposite direction from the deployment rotation. The electrodes deploy tangent to the spool. Accordingly, the angular position of each row of holes 417 may be determined by deciding the desired angle of deployment and rotating that angle 90° opposite deployment rotation.

In one embodiment, three bands of electrodes are provided in four rows, with deployment length of the electrodes being 10-14 mm, and deployment rotation being clockwise. FIG. 48 illustrates two rows of each of the three bands. The bands of electrodes are spaced one centimeter apart. The needles deploy upwardly approximately 15° into the upper left and upper right quadrants, and downwardly approximately 40° into the lower left and right quadrants. The routing holes are thus positioned rotated to the counterclockwise 90°. Each hole is approximately 5.1 mm long and approximately 0.18 mm wide, with length and width being from a center line. Total width thus is approximately 0.7 mm. It is to be appreciated that this embodiment is provided for illustrative purposes only and is not intended to be limiting.

As previously discussed, an inner sheath may be provided. In some embodiments, the inner sheath may comprise a flexible material capable of significant torque (for example, approximately 0.11 N-m). In one embodiment, the inner sheath comprises a composite material of a PEBAX inner layer, covered with a 0.13 mm×0.26 mm 304 stainless steel wire braid, with a PEBAX outer coating. The braid provides bi-directional torqueability of the shaft. The PEBAX layers provide good bonding surfaces and structure for the braid. The composite shaft thus may be flexible, bi-directionally torque-able, and chemically resistant.

The spool may be provided in any suitable manner. FIGS. 50, 51a, and 51b illustrate an embodiment comprising a continuous spool with electrodes wrapped generally from end to end on the spool. FIG. 52 illustrates an embodiment comprising a plurality of individual spools attached to one another. These spools may be oriented so that the electrodes on each spool are equal distances from the routing holes. In this embodiment, each electrode is spaced slightly below the previous electrode and the electrodes thus generally emerge as bands of one electrode, not in bands of multiple electrodes.

FIG. 50 illustrates a spool 410 without electrodes wound about it. The spool provides column strength and support to the electrodes, allowing them to be pushed by the spool out of the outer sheath. The configuration of the spool 410 in FIG. 50 permits the electrodes to emerge as uniform bands. Electrodes may generally be wrapped around the spool from end to end on the spool. The number of electrodes in each band is related to the number of continuous winds around the diameter of the spool. The number of continuous winds and the material thickness requirements between the winds determine the minimum pitch required for the winds. The pitch and the length of each electrode wound on the spool determine the minimum allowable spacing between rings of needles/electrodes. The spacing between rings of electrodes typically is a whole number times the pitch. The pitch of the wind and the length of the deployed needle/electrode determine the minimum length and the position of the direction holes (on the outer sheath). There also may be some translation of the electrode during its deployment due to the pitch of the wind on the spool.

The electrodes may be coupled to the spool by placing the spool in the outer sheath 413 and inserting the wire into a hole in the spool (that makes electrical contact with a wire running the length of the spool). When all of the wires are so attached, the wires are wound onto the spool. In one embodiment, the spool may be split, the electrodes (with the electrical conductors already connected) may be placed inside of the spool and adhered in place, and the spool put together. FIG. 51a shows half of a split spool 420 along with electrodes 406. The electrodes 406 are made in rows with a single wire coupled to them. The end of the single wire is coupled to a conducting wire 422 that runs to the handle. The spool is split so that the electrodes 406 can be adhered to the inside of the spool. The spool halves 420 are adhered together after the electrodes 406 are in place. Generally, each ring of wires is wound onto the spool before the spool can be inserted into the outer sheath. A tool can be used to accomplish this. Notches on the winding tool catch all the electrodes of a single band and hold them during the winding process, moving the spool inside the sheath as the wires are wound on the spool. This requires that the direction of the wind be so that it is directed proximately (as the spool is wound). Once all the wires are wound onto the spool and the spool is inside the outer sheath, the spool is advanced to the distal end of the outer sheath rotating the spool in the direction of the wind. At this time the winding can be removed by splitting it in half and cutting the o-rings helping to hold it together. FIG. 51b shows half of the spool 420 with O-ring seals 423 on both ends.

FIG. 52 illustrates a spool 425 wherein each electrode is wound on an individual spool 426. Using this design, each electrode is separated from another by at least the length of an individual spool 426. Each electrode is deployed generally perpendicular to the spool. Further, each of the individual spools 426 can be oriented. In one embodiment, the electrodes may be coupled to each spool using a wire running the length of the composite spool. Individual electrodes are inserted into a hole perpendicular to the wire, mechanically interfering with the wire and coupling the electrode to the composite spool. The wire makes electrical contact with the electrode and holds the electrode in place. Accordingly, the electrodes may be applied to the device after the device is assembled.

FIGS. 53 and 54 illustrate a winding tool 450 that may be used to wind the electrodes on the spool 410. In the embodiment shown in FIG. 53, the winding tool 450 comprises two parts 451 and 452 to allow easy removal from assembly once the electrodes are wound onto the spool 410 of the inner assembly (comprising, at least, the inner sheath). FIG. 54 shows the assembled winding tool 434 and inner device assembly 455 with the electrodes being wound on spool 410.

FIG. 55 illustrates a handle for an operating device for BPH treatment including a spool. The handle 430 may be designed to be lightweight, to be stiff, and to provide an adequate grip for the physician. The handle 430 comprises two parts, an inner handle 433, and an outer handle 434. As shown, the embodiment of FIGS. 51b and 55 includes three sets of O-ring seals. The first set comprises O-rings 423 on the ends of the spool 420, as shown in FIGS. 51b. These support the spool 420 and prevent contaminating fluids from entering the distal or proximal cavities of the device. The proximal O-ring also acts as a seal for air pressure in the cavity between the inner and outer device shafts. This cavity may be used for conducting the air pressure from the handle to the proximal balloon that is used for stabilizing the device during the insertion of the needles/electrodes. As shown in FIG. 55, the second set of O-ring seals 431, 432 may be positioned between two parts of the handle 430. These are the proximal seals for the air pressure between the shafts. The second set of O-ring seals 431, 432 also support the inner handle 433 as it turns within the outer handle 434. The O-ring seals 431, 432 allow the cavity between the inner shaft and the outer shaft to be pressurized to inflate a proximal balloon. The inner handle 433 may be coupled to the steering handle with a retaining ring 435. The third set of o-ring seals may be provided in the distal tip. A tube attached to the spool rides within the seals. The seals prevent air leakage from the air conduit between the handle and the distal balloon, yet allow the spool to turn within the outer sheath attached to the rubber tip.

FIGS. 56a and 56b illustrate aspects of a handle 430 that may be used to align the device with the urethra (and prostate) and for deploying the needles/electrodes at discrete depths into the prostate based upon the length, width, and depth of the prostate (as determined during assessment of the tissue), and a predetermined chart. An indicator ring 438, shown in FIG. 56a, may be used to indicate electrode extension distances. FIG. 56b illustrate the inner handle 433 and outer handle 434 of the handle 430. A spring plunger is used to create discrete steps in the extension of the electrodes as well as stops for electrode extension and retraction. The setting on the electrode extension indicator 438 may be selected via a cursor 439. FIG. 56b is an end view of the handle 430 and shows depressions 440 for creating discrete steps for the electrode extension with the spring plunger. A set of stops 441 is provided across the path of the spring plunger to form stops for the electrode extension and retraction.

Figure 57:
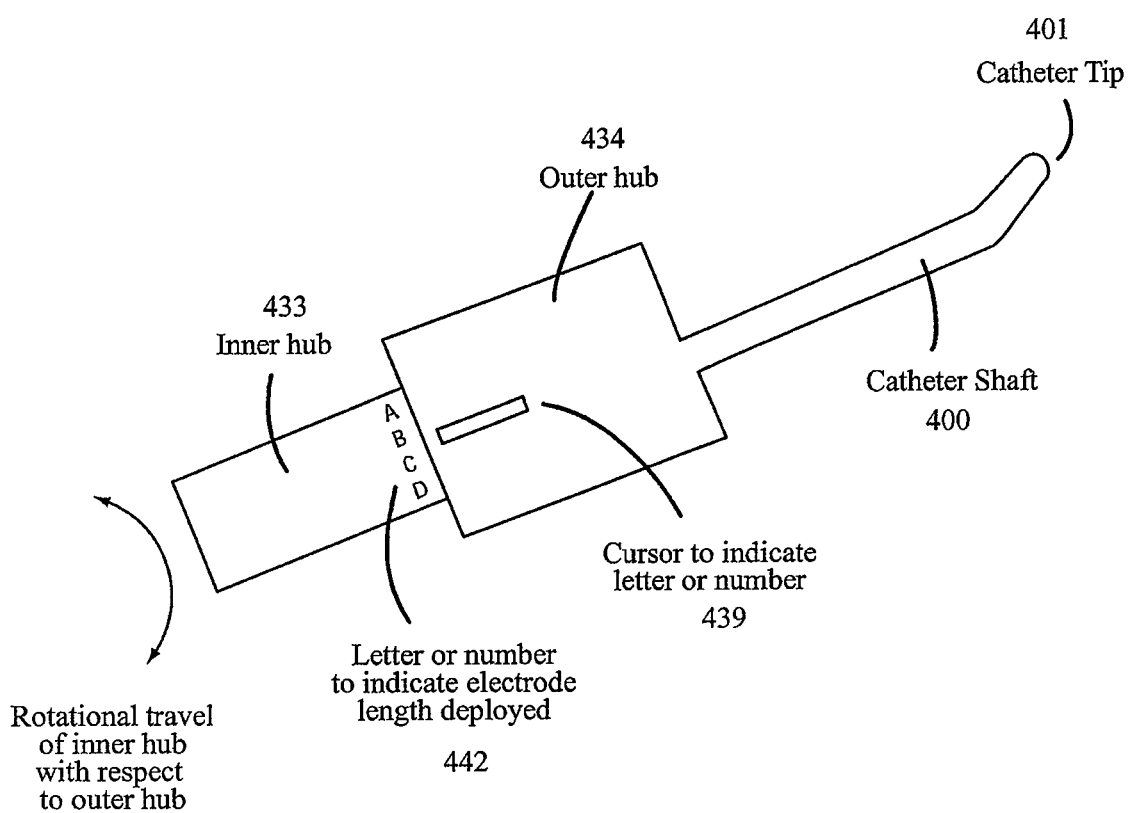
FIG. 57 illustrates visual and physical indicators on a catheter including a rotational indicator on a handle grip and an electrode deployment position indicator on a handle dial, in accordance with one embodiment.

FIG. 57 illustrates the overall system including a catheter 400 having a tip 401, a handle having an outer hub 434 and a cursor 439 to indicate letter or number, and an inner hub 433 (shown exploded from the outer hub) with a letter or number or other designation 442 to indicate electrode length deployed. In some embodiments, indication may be audible. The inner hub 433 may be rotated relative the outer hub 434 to deploy electrodes through the catheter shaft.

Figure 58:
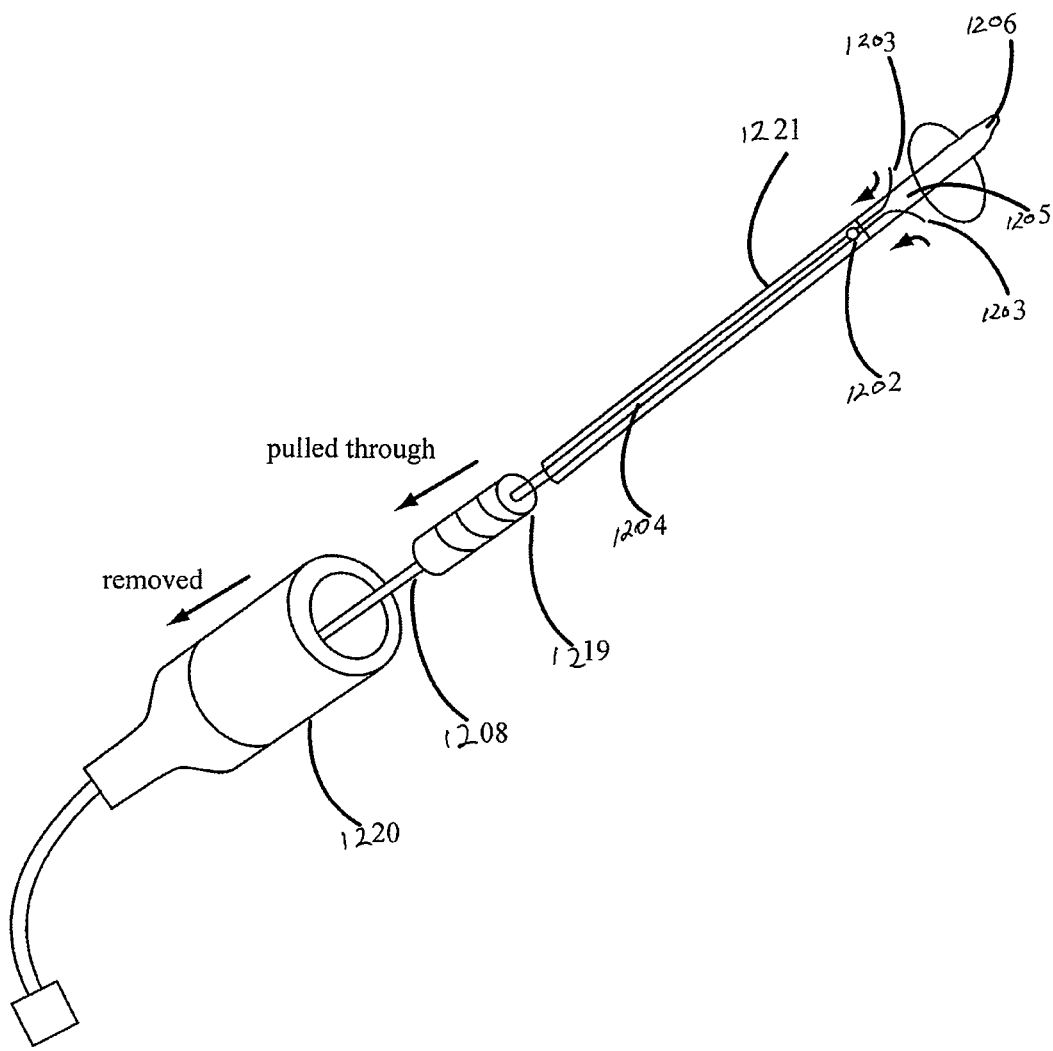
FIG. 58 illustrates an emergency escape mechanism for disassembling the catheter so the electrodes can be removed from the body, in accordance with one embodiment.

In some embodiments, a removal mechanism may be provided for emergency removal of electrodes in the event that normal retraction of the deployed electrodes fails. Such removal mechanism may comprise an outer tube for placement over the deployed catheter and electrodes. In some embodiments, the outer tube may be placed separately from the system for BPH treatment and may only be placed upon failure of the electrode retraction. In other embodiments, the outer tube may be part of the system for BPH treatment as deployed. In one embodiment as shown in FIG. 58, the outer sheath adjuster 1219 and outer sheath 1221 are removed from the handle grip 1220. When the outer sheath adjuster 1219 is removed from the handle grip 1220, the inner sheath 1204, the driver 1202, the electrical conductors 1208, and the electrodes 1203 can be removed from the outer sheath 1221, director 1205, and tip 1206. This causes the electrodes to be pulled back through the director and back into the inner lumen of the outer catheter. At this point the entire catheter can safely be removed. In some embodiments the system provides a custom wrench to remove the handle assembly from the inner catheter assembly. In some embodiments the mechanism for releasing the inner catheter from the outer catheter is covered by a cosmetic cap.

Various catheter configurations are suitable for use with a DC ablation system and method as discussed herein. The catheters may comprise different materials and different configurations. Generally, the catheter is provided as a semi-flexible tube. A flexible catheter is generally more comfortable for patients. A rigid catheter, however, is generally easier for electrode deployment. Catheters as provided herein have a balance of flexibility and rigidity to maximize comfort while facilitating electrode deployment.

Generally, flexible catheters reduce tissue trauma during the treatment procedures, particularly in the urethra. Particularly for transurethral insertion, it can be difficult to navigate past the veromontanum in the prostate, where the urethra takes an approximately 30 degree angle. However, rigidity is desirable for precise and consistent electrode deployment. Further, in a specific embodiment routing holes may be cut into the catheter for facilitating electrode extension therethrough. The routing holes may compromise torque resistance. In embodiments wherein the electrodes are extended by rotation, that rotation exerts torque on the shaft. If the shaft does not resist the torque, the electrodes may not fully deploy and/or may not deploy in the intended direction. Accordingly, catheters for use with systems for treatment of tissue as described herein balance the desirability of flexibility and rigidity. A 4 Newton force results in approximately 60 to 80 mm of lateral deflection for an approximately 300 mm catheter shaft that contains an outer and inner sheath. The shaft may be configured to withstand an approximately 40-80 Newton axial force with less than approximately 1% of strain over 300 mm length. This combination of lateral flexibility and axial stiffness facilitates electrode deployment while allowing the patient to be treated comfortably during a 20-45 minute procedure.

The material chosen for the catheter thus may be one having some degree of flexibility and also some degree of rigidity. Chemically resistant materials useful for the catheter include, for example, PEEK, PEBAX, polyimide, silicone, platinum iridium, and Nitinol. In the body of the catheter, wire braid covered by 63 D PEBAX can provide a structurally stable tube that provides good torsion and longitudinal stiffness, yet resists kinking, and allows the tube to bend through tortuous delivery paths. In another embodiment the PEBAX has a range of durometer of 50 D to 75 D. In a specific embodiment routing holes may be drilled through the braiding; however, this may compromise the braid properties. Accordingly, in areas that require routing holes, PEEK tubing may be used in place of the metal braiding. An approximately 0.3 to 0.4 mm wall PEEK tube is torsionally stiff over an approximately 350-360 mm length, and is relatively stiff to bend. In further embodiments, described below, the PEEK tubing may be combined with a metal braiding and PEBAX to provide a bendable, kink resistant tube that has a short, non-braided section that can be laser drilled or machined to include routing holes. The layers may be optimized to provided bendability and torque-ability to meet the needs of specific applications. A tapered tip may be provided to substantially prevent perforation when inserting the device. In some embodiments, the tip may be approximately 20-40 mm in length and made from silicone rubber.

In some embodiments, the material of the catheter thus may be a composite material. In one embodiment, the catheter is formed from a thermoplastic such as PEEK, which provides high torque resistance even with holes cut therethrough. PEEK is biocompatible and resistant to chemicals and processes such as electrolysis. PEEK can be heat shaped and, thus, may be thermoformed to substantially match the area into which it is to sit during treatment, making placement of the catheter and retention of the catheter during treatment easier.

Figure 59A:
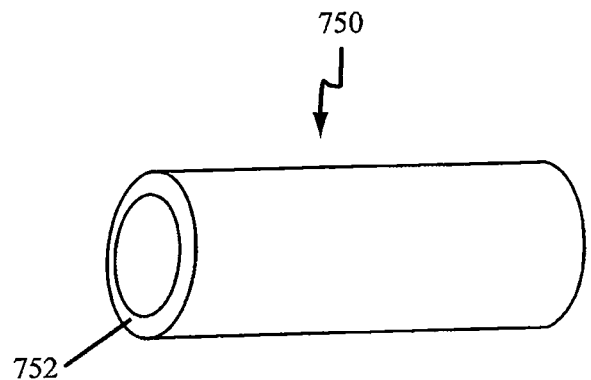
FIG. 59a illustrates a PEEK tube for an outer or inner sleeve, in accordance with one embodiment.
Figure 59B:
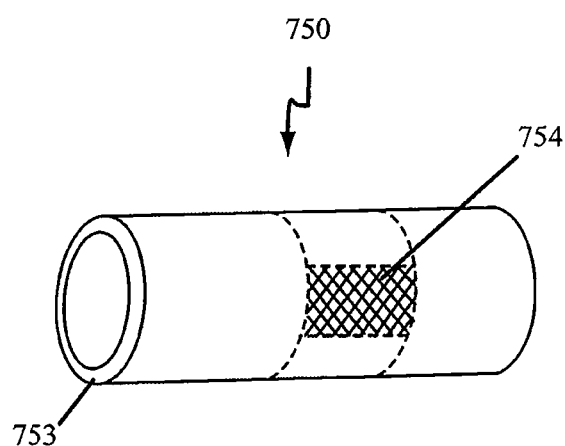
FIG. 59b illustrates a PEEK tube and an inner core, with metal braiding on the outside of the PEEK, and a PEBAX layer over the metal braiding, in accordance with one embodiment.

FIGS. 59a and 59b illustrate various catheter embodiments. In one embodiment of a PEEK catheter, shown in FIG. 5 切, the catheter 750 comprises a PEEK tube 752 having an approximately 0.3 to 0.4 mm wall. Tube thickness may be adjusted for specific applications. In another embodiment of a PEEK catheter, shown in FIG. 59b, the catheter 750 comprises a PEEK tube 753 with stainless steel braiding 754 and PEBAX. The PEEK tube 753 with braiding 754 has torque resistance similar to the PEEK tube 752 alone but has increased flexibility. In some embodiments, the catheter 750, and the tapered tip of the catheter, may be shaped to match the veromontanum area.

The catheter may be shaped to match anatomy in which it is to be placed. Thus, for example, in embodiments for BPH treatment, the catheter is intended for transurethral insertion through the male anatomy. Accordingly, in a further embodiment, shown in FIG. 60 the catheter 750 comprises a bend 756 matching the bend in male anatomy wherein the device sits during treatment. The bend facilitates easier insertion with less trauma through the male urethra, enables the catheter to remain in place with less force and more comfortably during treatment, and reduces trauma in catheter removal. In a specific iteration of the embodiment of FIG. 60, the catheter 750 may have a length of approximately 200 mm along the shaft 758 and a length of approximately 100 mm along the bend portion 760. The bend portion 760 may have a traveled length 762 of approximately 40 mm.

Figure 60:
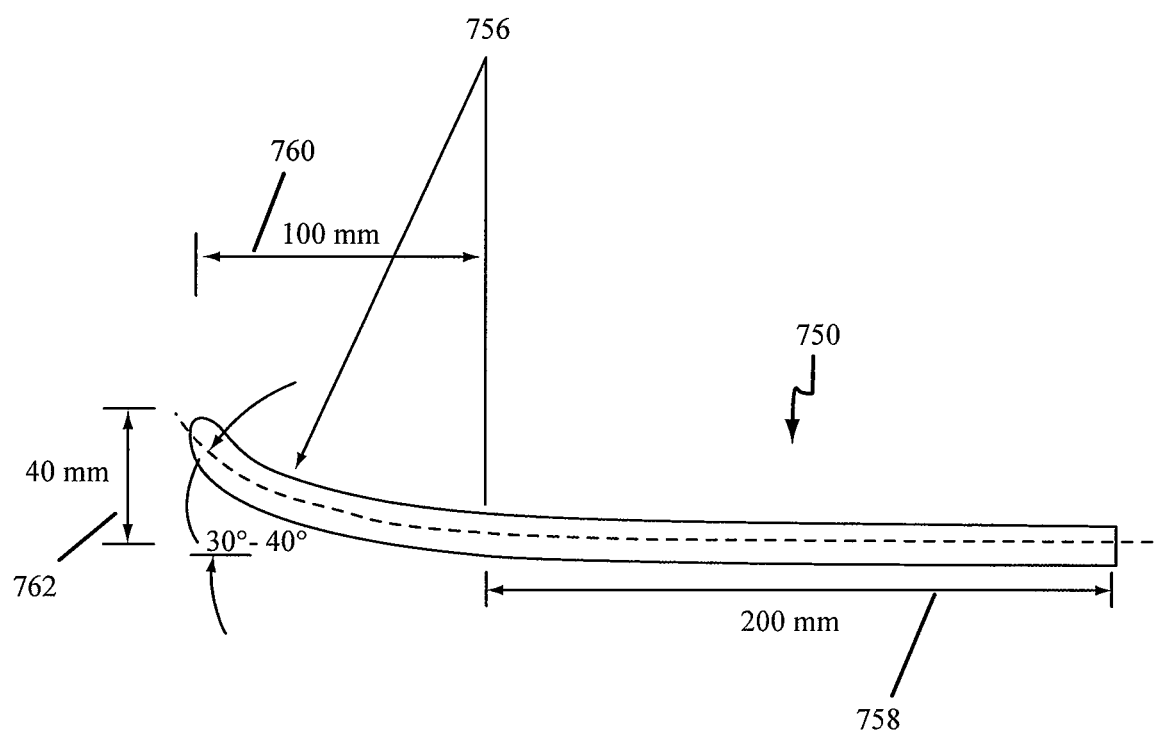
FIG. 60 illustrates one embodiment of a curvature in a catheter for ease of insertion and comfort during the treatment.

To form the catheter of FIG. 60, a straight tube made of a flexible material, such as PEEK is heat set to a prescribed radius and dimension. The tube may be of uniform diameter and wall thickness for uniform tube flexibility. In alternative embodiments, the tube may be of changing diameter and wall thickness to increase or soften the tube flexibility moving from a first (or distal) end to a second (or proximal) end. The tube is formed with an angle approximately 30 degrees, substantially matching the angle of the prostatic urethra from the veromontanum to the bladder. The tip of the tube at its distal end may be flexible and angled at approximately 30 degrees to facilitate tracking of the tube through the prostatic urethra.

Figure 61:
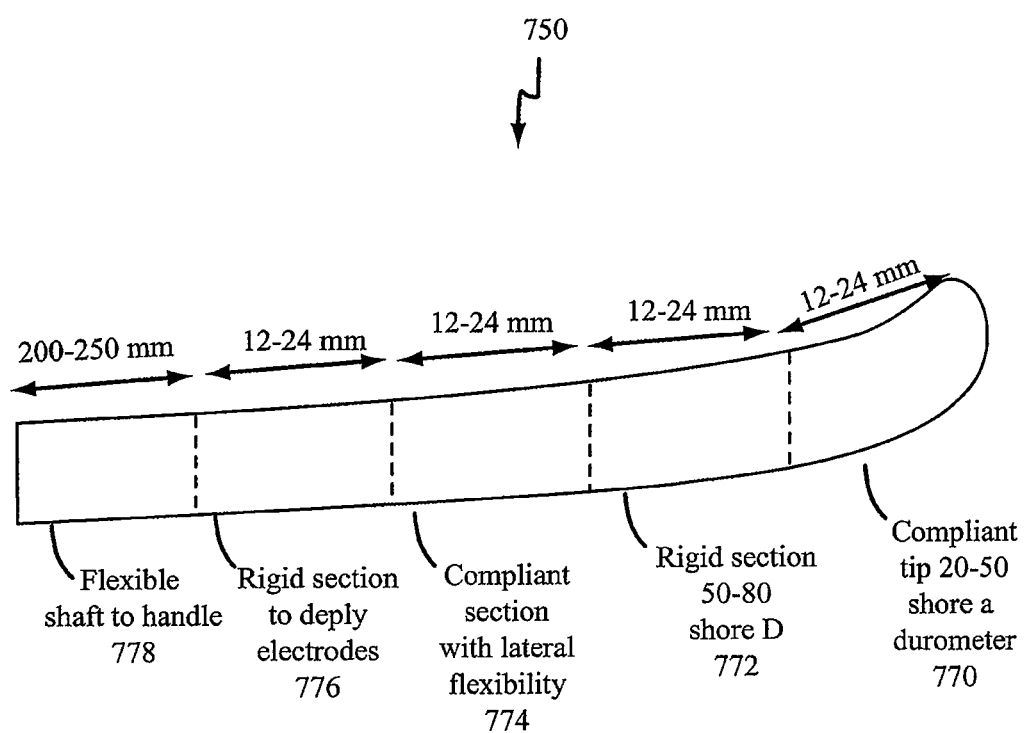
FIG. 61 illustrates a catheter with different sections of differing durometer and so flexibility, in accordance with one embodiment.

FIG. 61 illustrates a catheter 750 comprising alternating flexible and rigid sections. Generally, a catheter having localized rigidity and compliance facilitates comfortable placement and precise placement of treatment electrodes. In the embodiment of FIG. 61, each section may range, for example, between approximately 12 mm and approximately 24 mm in length. The rigid sections enable catheter/electrode placement force to advance the treatment section. The compliant sections facilitate steering of the tip through the urethra (or other structure). The embodiment of FIG. 61 illustrates a compliant tip 770 comprising an approximately 20-50 Shore A durometer. The catheter, from distal to proximal, includes compliant tip 770, rigid section 772, compliant section 774, rigid section 776, and a flexible shaft 778 to handle. The rigid section 772 may comprise an approximately 50-80 Shore D durometer. The compliant section 774 has lateral flexibility. The rigid section 776 facilitates electrode deployment. Each of sections 770-776 may have lengths of approximately 12 to approximately 24 mm. The flexible shaft 778 may have a length of approximately 200-250 mm.

Figure 62A:
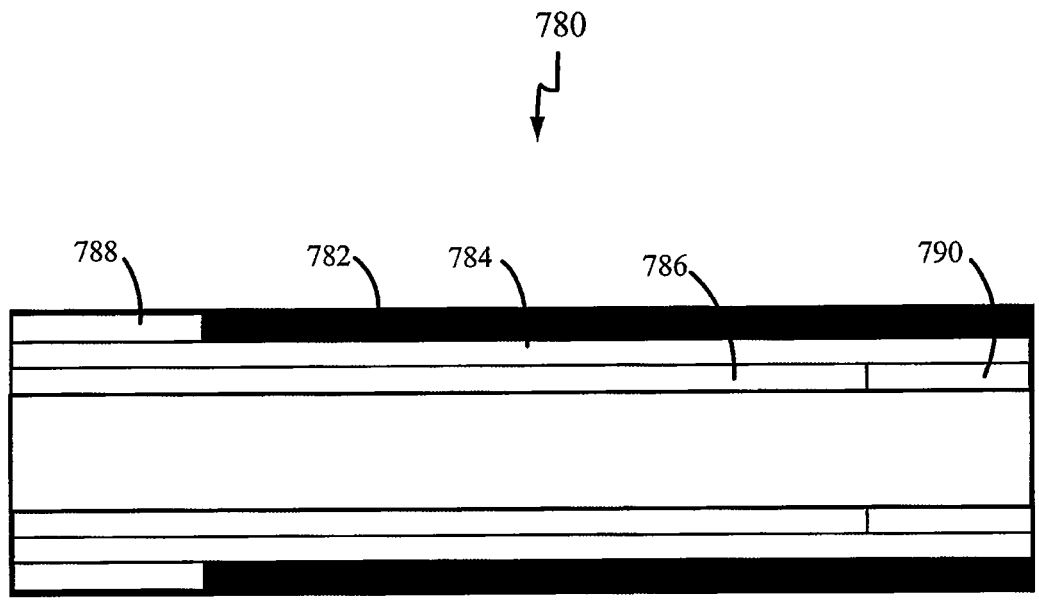
FIG. 62a illustrates a cross-section of a catheter with an outer layer, a metal braid layer, and an inner layer, and a ring electrode on the outside of the catheter body that is attached to the metal braid, in accordance with one embodiment.
Figure 62B:
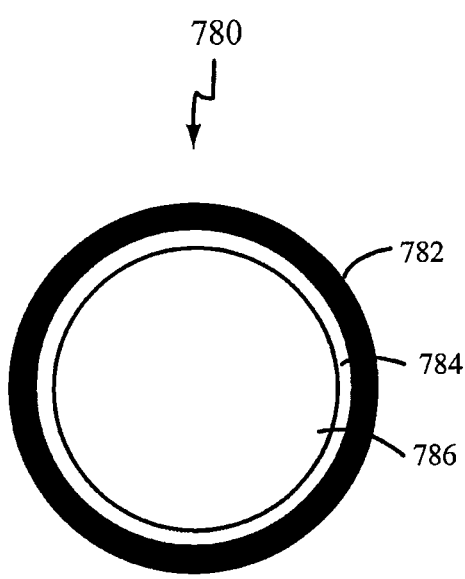
FIG. 62b illustrates a cross-sectional end view of a catheter with an outer layer, a metal braid layer, and an inner layer, in accordance with one embodiment.

FIGS. 62a and 62b illustrate an example composite material catheter 780. As shown, the composite material comprises a plastic outer layer (PEBAX) 782, a reinforcing middle layer 784, and a plastic inner layer (PEBAX and/or PTFE) 786. The layers may be bonded or adhered to one another or may be coupled substantially only through contact. Such composite is flexible yet is resistant to bi-directional torque, for example torque of approximately 1 inch-pound. In one embodiment, the reinforcing middle layer 784 may comprise a metal braid such as a 0.13 to 0.26 mm stainless steel wire braid In the embodiment of FIGS. 62a and 62b, the inner layer may be PEBAX or may be PTFE. For an inner sheath, the inner layer 786 may be PEBAX to facilitate adhesion to the attaching parts and the PEBAX outer surface provides adhesion capabilities. In contrast, for the outer sheath, the inner layer 786 may be PTFE for chemical resistance and low friction. The PTFE provides an electrical insulator, a chemical barrier against by-products of the treatment, and a low friction surface upon which the needles/electrodes and o-rings can slide. For an outer shaft, the PEBAX outer layer 782 provides a good bonding surface, is resistant to the treatment by-products, and provides a smooth surface interface with the tissue.

Reference was made above to the use of braid in the catheter. The metal braid is woven over an inner liner and mandrel in the process of making a torque-able catheter shaft. This is for mechanical stability in pushing, pulling, and rotating the catheter during its use. This is covered with an outer plastic jacket to reduce friction and provide mechanical and chemical stability. By adding a ring to each end of the catheter and attaching rings to the braid the braid becomes a multi-filar conductor with electrically insulating surfaces surrounding the conductor.

Returning to FIGS. 62a and 62b, FIG. 62a shows a side view and FIG. 62b shows an end view of a catheter shaft 780. Both views include the inner insulation layer 786, the middle metal braid layer 784, and the outer insulation layer 782. The side view also shows the outer conduction ring 788 at one end of the shaft which is electrically attached to the middle metal braid layer and the inner conduction ring 790 at the opposite end which is also electrically attached to the middle metal braid layer. Braiding in the outer 20 Fr tube to get this combination of lateral flexibility and axial and torsional stiffness can be achieved by stainless steel braid with 50-80 PPI (picks per inch) and wire cross section round or flat 0.13 mm to 0.26 mm.

The catheter may be made up of one or more layers of braid, with insulating layers inside, outside and between braid layers. The ring or contact surface may be used for making electrical contact with the ends of the catheter. These variations may save space inside the catheter, allowing the catheter/device to be smaller. In some embodiments, two or more electrically independent conducting braids may be woven together and separated by an insulating jacket. Provided the flexibility of the overall braided assembly is maintained, this permits the use of multiple conductors with very little increase in catheter diameter.

In its manufacture, a mandrel may be used to hold the inside diameter consistent and provide support during the construction of the catheter. It is removed after the catheter construction is complete. First, a plastic insulating layer is placed over a mandrel. If conduction rings are desired on the inside of the catheter, the rings are placed on the mandrel next to the ends of the inner insulation. The braid is formed over the inner insulation layer (and conduction rings if present). If the rings are desired on the outside of the catheter, the rings are placed over the braided conductor. The rings are attached to the braid. This may be accomplished through silver soldering, laser welding, crimping, or swaging. The braid may also be formed into a ring itself by welding or soldering the wires together. An insulating, durable layer is extruded or heat shrunk over the braid and rings on the end of the braid. The entire process is repeated for the desired number of conductors. A bonding process such as thermo-bonding may be used to bond all the layers into one structure.

Figure 63:
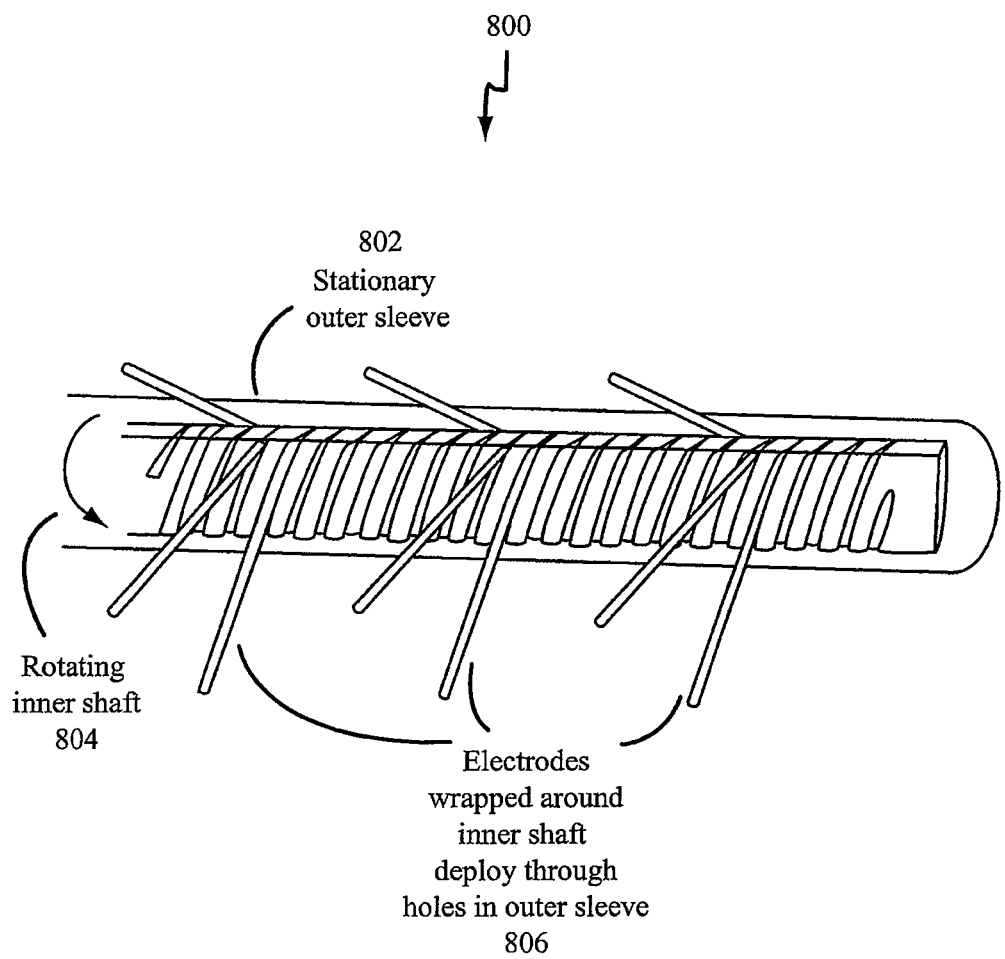
FIG. 63 illustrates a cross sectional view of the distal end of a radially deployed electrode catheter, in accordance with one embodiment.
Figure 64:
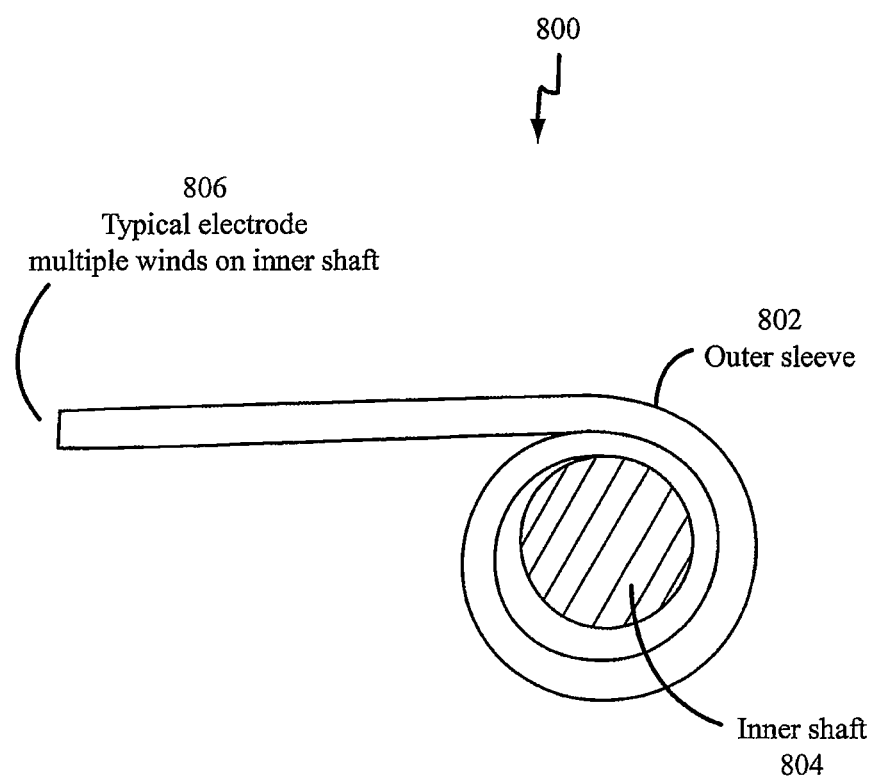
FIG. 64 illustrates an end view of a single electrode being wrapped on a spool in a radially deployed electrode catheter, in accordance with one embodiment.

Catheters for use with the system and method for tissue treatment as discussed herein may further be customized for specific uses. FIGS. 63 and 64 illustrate a rotary catheter for prostate ablation, such as may be suitable with systems having radial electrode deployment. FIG. 63 illustrates a side view and FIG. 64 illustrates an end or cross-sectional view. The rotary catheter 800 comprises an outer sleeve 802 and a mandrel 804 (also referred to as an inner sleeve or inner shaft). Electrodes 806 are coupled to the mandrel 804 and extend through the outer sleeve 802. The size of the mandrel 804 may be chosen based on associated wrapping of the electrodes 806. More specifically, a mandrel 804 having a larger diameter uses fewer rotations of the electrodes 806 therearound to achieve the same penetration length. In the embodiment of FIG. 64 the electrode 806 wraps around the mandrel 804 with 2¼ wraps. As the center mandrel 804 (or inner tube) is rotated, the electrodes 806 rotate and unwrap from the catheter 800.

In some embodiments, a catheter assembly may be provided comprising an outer guide catheter or sheath and an inner activation catheter or inner sheath. The outer catheter guides the system into treatment position. The inner catheter provides the movement for the activation of the electrodes. The catheter body may be optimized for the treatment site and path, using any of the embodiments described above. In one embodiment, the outer catheter comprises PEEK covered with braiding and a PEBAX exterior. The PEEK, braiding wire size, and braiding configuration control the flexibility and torque-ability of the catheter. A distal portion of the catheter may not include a braid section to facilitate routing holes therethrough. PEEK thickness may be chosen based on the length of the unbraided section, flexibility requirements, and kink-resistance requirements. Other factors affecting the thickness of the PEEK include the resistance the PEEK wall can provide to the electrode penetration as the electrodes are retracted and extended through the outer catheter. In one embodiment, the PEEK wall is approximately 0.38 mm with a 0.15 mm 304 stainless steel wire braid with a 50 ppi configuration and a 0.18 mm wall PEBAX cover. A 2-4 mm diameter PEEK pushrod inside of 5-7 mm diameter braided outer tube can be used to balance lateral flexibility with torsional and axial rigidity.

Figure 65A:
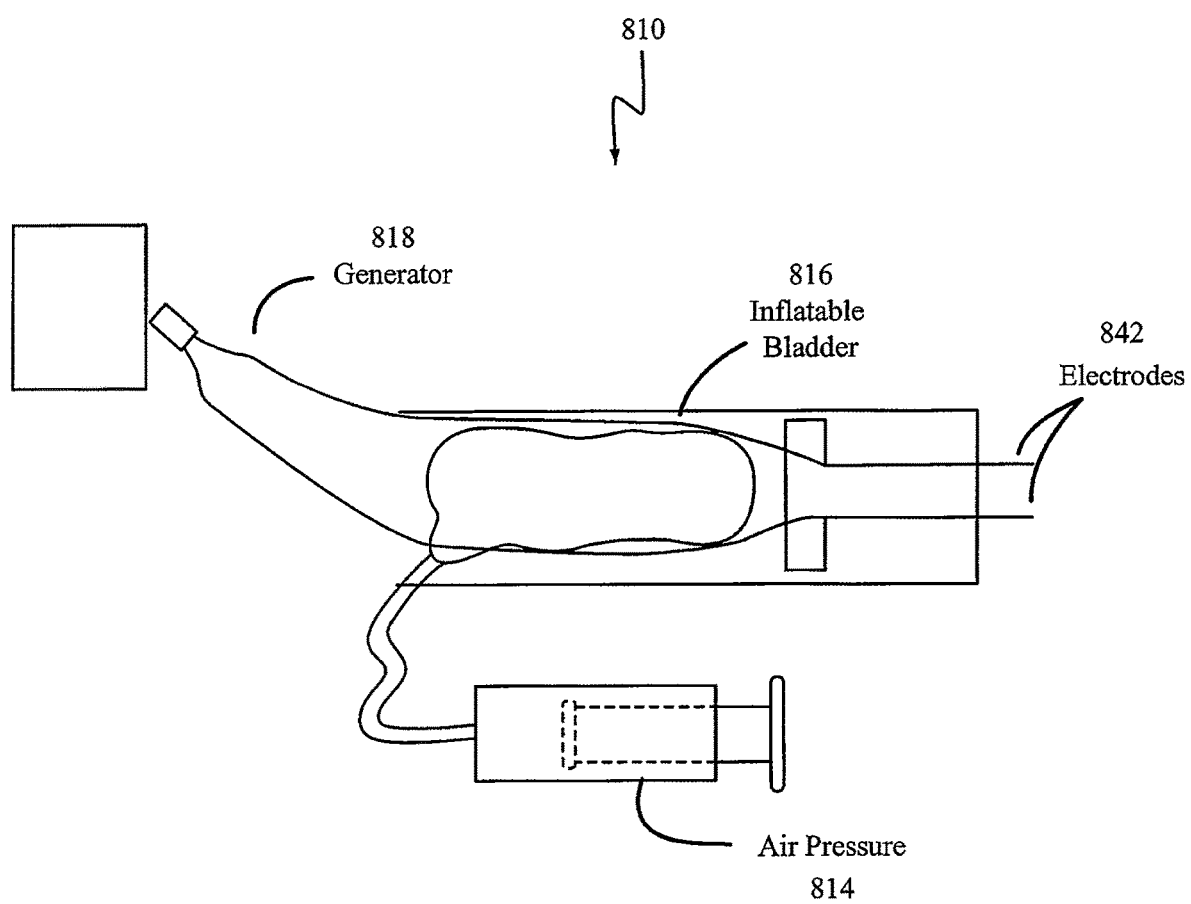
FIG. 65a illustrates a system including a pneumatic deploying electrode catheter, in accordance with one embodiment.
Figure 65B:
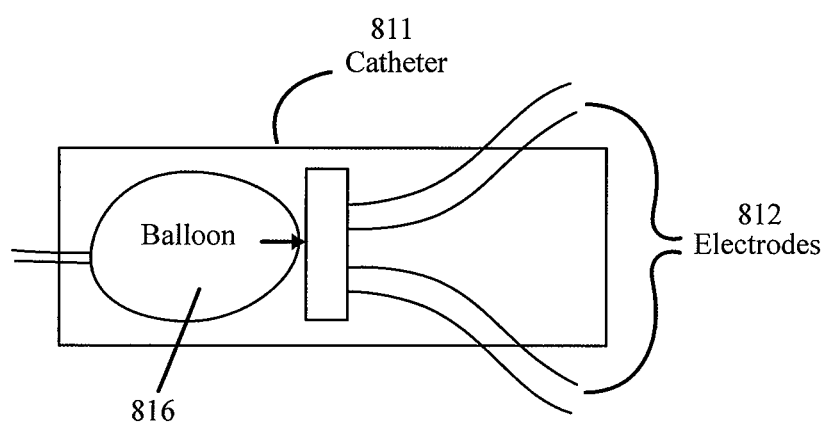

FIGS. 65*a* and 65*b* illustrate a pneumatic catheter for use with systems and methods for tissue treatment as discussed herein. The pneumatic catheter 810 and 811 can reduce the catheter diameter and facilitate rapid electrode advancement if necessary for penetration. The catheter 810 and 811 may further be used for transvenous applications where the length of the catheter can make mechanical means for insertion more difficult or where catheter diameter must be minimized. Catheter 810 shows one embodiment where the electrodes are deployed out the distal end of the catheter and catheter 811 shows one embodiment where the electrodes are deployed out laterally from the catheter. Generally, transurethral catheters may be between approximately 14 and approximately 22 French (for example, between 17 and 20 French) but transvenous catheters are generally between approximately 4 and approximately 12 French. In the embodiment of FIG. 65*a*, the catheter 810 has electrodes 812 cooperating therewith and is coupled to an air pressure system 814. The catheter 810 includes an inflatable bladder or balloon 816 that may be expanded or inflated using the air pressure system 814. The catheter 810 further is associated with an electrical generator 818 that delivers the therapy once the electrodes have been deployed into tissue. The electrodes 812 may be deployed by inflating the bladder or balloon 816. The air pressure system 814 may comprise a piston that is, for example, pneumatically actuated to inflate the bladder or balloon 816. In another embodiment, the air pressure system 814 may be associated with a pushrod in the catheter such that the air pressure system actuates the pushrod.

A further embodiment comprises a vibrating catheter and electrode system. Systems for treating tissue using DC ablation may result in high impedance due to formation of bubbles during electrolysis. The combination of oxygen at the anode and hydrogen at the cathode leads to impedance increases, which in turn increases therapy time because the current must be lowered or paused. A vibration mechanism is coupled to or incorporated within the catheter. For example, a suitable vibrating mechanism comprises a DC motor with an eccentric weight.

Figure 66A:
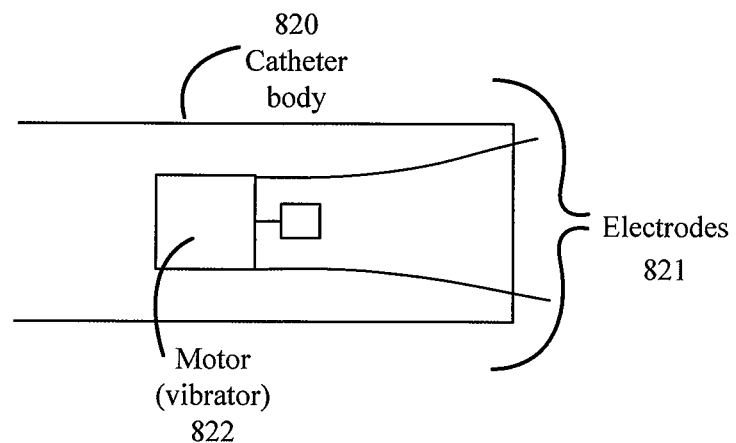
FIG. 66a illustrates an electric vibrator attached to the electrodes for improving contact of the electrodes with the tissue and to remove gases, in accordance with one embodiment.
Figure 66B:
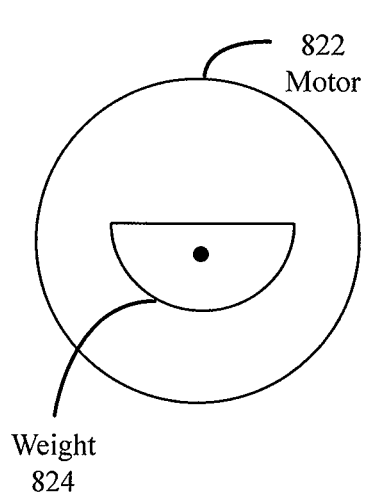
FIG. 66b illustrates an eccentric weight on a motor shaft as one embodiment for vibrating the electrodes or catheter.
Figure 66C:
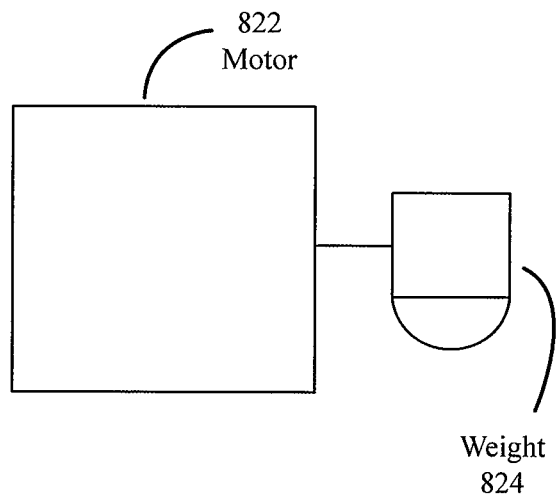
FIG. 66c illustrates a weight offset from the shaft of the motor to produce vibration, in accordance with one embodiment.

FIG. 66*a* illustrates a catheter 820 embodiment including electrodes 821 and a motor vibrating mechanism 822 mounted thereon. As shown, the vibrating mechanism 822 may be placed near a proximate end of the catheter 820. In alternative embodiments, the vibrating mechanism 822 may be placed at or near the handle, in the catheter, or at alternative suitable position. The vibrating mechanism 822 may be actuated to cause vibration of the catheter 820 thereby breaking up the gas bubbles and lowering impedance between the treated tissue and the electrode 821. Suitable frequencies for impedance reduction may range from approximately a few hertz to a few kilohertz. In further embodiments, the vibrating mechanism may be optimized to aid in tissue penetration or removal from the tissue. Frequencies for aiding in tissue penetration may range from, for example, several hundred hertz to approximately 30 kilohertz. FIG. 66*b* illustrates an end view of a weighted motor suitable for use with a vibrating catheter as described herein. As shown, the motor or vibrating mechanism 822 includes a weight 824. FIG. 66*c* illustrates a side view of a weighted motor, including a motor or vibrating mechanism 822 and a weight 824, suitable for use with a vibrating catheter as described herein.

In one embodiment the catheter assembly has a drainage conduit from the tip of the catheter out to the back of the handle. This allows the bladder to be drained during treatment and minimize any urinary urgency during treatment. The drained fluid may be allowed to free fall from the catheter or be connected to a collecting bag with a connector on the catheter. A vacuum may be added to further facilitate bladder drainage.

In one embodiment a conduit is provided within the catheter to supply saline or other buffering solution to the lumen or urethra in which the catheter is placed. This allows additional protection of the inner tissues of the lumen from the high and low pH created by treatment. This fluid may be injected intermittently or continuously supplied from a fluid bag hung above the patient. The fluid maybe introduced into the urethra from the ports at which the electrodes exit the catheter or ancillary ports in proximity to the anticipated treatment zone.

When treating the prostate for BPH it may be advantageous to compress the tissues during or immediately after treatment to acutely reduce urinary blockage. The treatment softens the tissues and by compressing them it acutely opens that passageway until the treatment permanently removes the pressure on the urethra by debulking the prostate. In one embodiment the catheter has a small inflatable balloon adjacent to the area of treatment. This balloon can be inflated with 3 to 15 cc of saline to put pressure on the treatment during or immediately after treatment. In another embodiment the catheter is repositioned after treatment and the distal fixation balloon is inflated in the urethra adjacent to the treatment zones to compress the tissue.

In some embodiments the catheter may be hooked up to a vacuum pump that puts negative pressure within the body of the catheter and at holes in the catheter which are in proximity to the treatment zone or electrode insertion points. This allows the tissue to be held tightly to the catheter during the insertion of the electrodes and prevents the tissue from tenting around each of the electrodes. This increases the precision of electrode placement in the tissue. These vacuum ports in the catheter may also be used to suction the gas generated in the treatment zones to prevent gas build up at the electrodes or from gas to transport a high or low pH solution down the lumen or urethra. In some embodiments the vacuum ports in the catheter are the same holes from which the electrodes extend. In another embodiment the vacuum ports are dedicated. In some embodiments the ports may be used to put a positive pressure on the lumen or urethra prior to electrode insertion to facilitate precision electrode positioning in the tissue. In some embodiments the vacuum pump is integrated with the DC ablation generator.

In some embodiments, the catheter may be configured as a single-use disposable device. The system may prevent more than one use of the catheter by disabling the catheter after completion of one therapy session. In one embodiment, the catheter may include a non-volatile memory. Before starting treatment, the generator checks the data in the memory and only starts treatment if the data indicates that the catheter has not been previously used. When the generator determines that treatment has been completed, the generator writes data to the catheter memory to indicate that the catheter has been used, disabling the catheter for future use in the system.

The memory may be accessed via wires or wireless, for example an RFID (radio frequency identification) device. In another embodiment, the catheter may include a fuse. Before starting treatment, the generator checks whether the fuse is intact and only starts treatment if the fuse is intact. When the generator determines that treatment has been completed, the generator may output a high level of current to cause the fuse in the catheter to open, disabling the catheter for future use in the system.

The deployed electrode length may be measured and indicated by using electronics in the catheter. The deployed electrode length could be determined based on the rotational position of the handle or based on the linear position of a shaft that controls deployed electrode length. A circuit incorporating a switch or multiple switches may be used to detect the rotary position of the handle or linear position of a shaft in the catheter and to indicate the corresponding deployed electrode lengths. A circuit incorporating a rotary switch or potentiometer may be used to determine the rotational position of the handle and indicate the corresponding deployed electrode length. A circuit incorporating a slide switch or potentiometer may be used to determine the linear position of a shaft in the catheter and indicate the corresponding deployed electrode length. The deployed electrode length may be indicated using LED's or a display on the catheter or using the display on the generator. In one embodiment a safety light or audible alert indicates that the electrodes have been completely retracted and the catheter is safe to remove from the body.

Figure 67A:
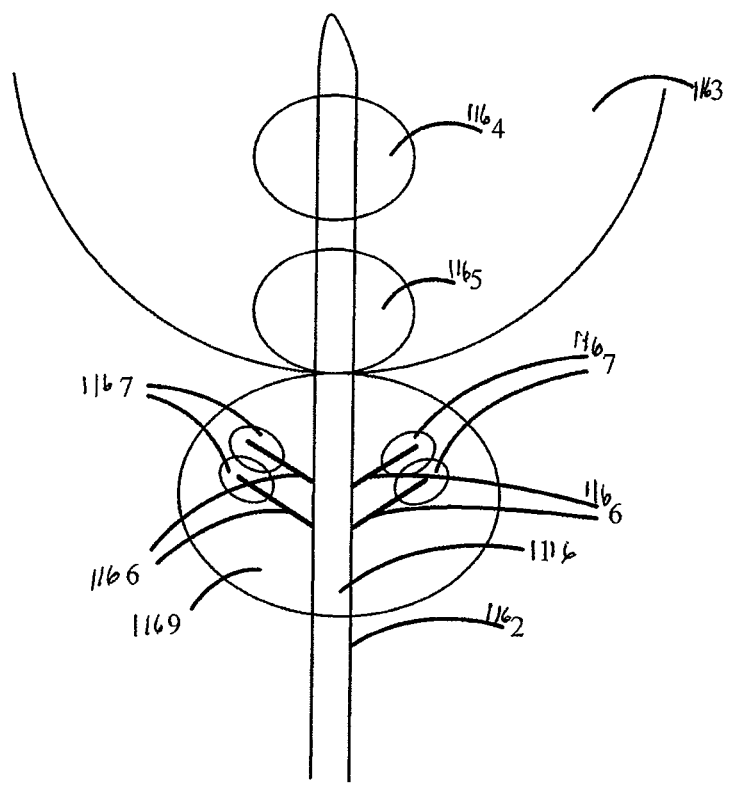
FIG. 67a illustrates the human male anatomy with a catheter with multiple balloons for customizing the position of electrodes inserted into the tissue, in accordance with one embodiment.
Figure 67B:
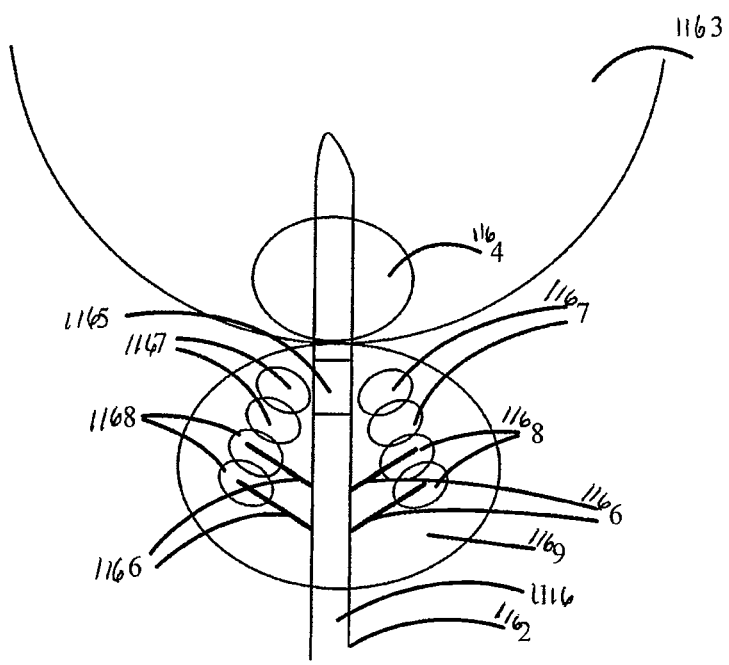
FIG. 67b illustrates the human male anatomy with a catheter of FIG. 67a having a new position after one of the balloons having been deflated and the electrodes repositioned to create new treatment areas.

In one embodiment as illustrated in FIGS. 67a and 67b a transurethral catheter 1161 is placed in the urethra 1162 and advanced to the bladder 1163. Two balloons 1164 and 1165 are inflated in the bladder. The balloons may be inflated together or independently. One balloon 1164 is more distal and than the balloon 1165 in its position in the bladder. The proximal balloon 1165 is seated in the bladder neck and electrodes 1166 deployed into the prostate 1169. DC ablation is performed and treatment zones 1167 are formed around the electrodes 1166 as shown in FIG. 67a. In larger prostates where more treatment zones are required to complete the overall treatment, the electrodes 1166 can be retracted back into the catheter 1161, and the proximal balloon 1165 deflated. As shown in FIG. 67b the proximal balloon 1165 has been deflated and the catheter repositioned such that the distal balloon 1164 now is seated in the bladder neck. Electrodes 1166 can now deployed into the prostate in a new area proximal of the first treatment zones 1167 and new treatment zones created 1168. After the second treatment is completed the distal balloon 1164 is deflated, electrodes retracted and catheter removed. This treatment utilizing multiple balloons to use as a fixation element can be used when a single catheter is insufficient for treating larger prostates. In some embodiments the catheter 1161 may have 2, 4, 6, or 8 electrodes. With two positions and treatments these yield 4, 8, 12, and 16 treatment zones to maximize the amount of tissue necrosis created within the prostate.

Figure 68:
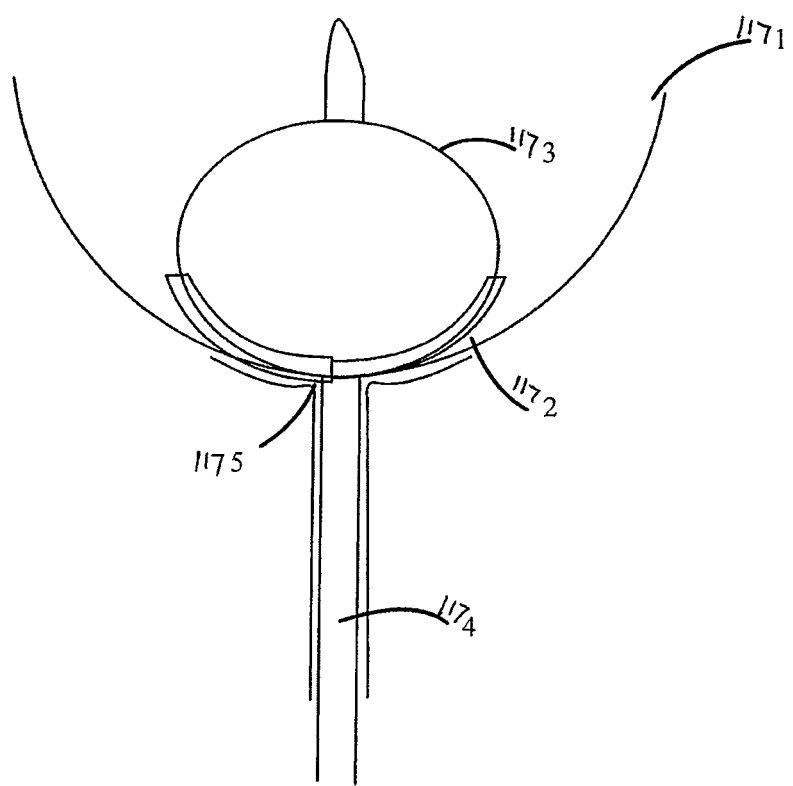
FIG. 68 illustrates a balloon made from multiple layers to selectively make the side toward the bladder neck stiffer and seat better in the bladder neck, and leave the single layered portion directed toward the bladder.

In one embodiment as shown in FIG. 68 an inflatable silicone balloon 1 has dissimilar stiffness or durometer from the proximal 1172 to distal half 1173. The proximal half has a higher stiffness or durometer than the distal half. This can be accomplished by knitting multiple layers of silicone on the proximal half or using two different durometers of material. This will allow greater expansion of the distal half of the balloon than in the proximal half. This will shape the proximal edge of the balloon to be flatter and more accurate in seating a catheter 1174 in annular orifices such as the bladder neck 1175. This will result in the ability to more accurately place electrodes in tissues such as the prostate.

Each of the embodiments of the system for treating tissue comprises catheters and electrodes as described above and further comprises an electronic control system or generator.

EXAMPLES

The following examples are for illustrative purposes only and are not intended to be limiting.

Example 1

A study was performed to evaluate the chronic effects of DC ablation in canine prostates. Eight chronic canine subjects were treated to evaluate the healing cascade, dose response, prostate shrinkage, and the duration of time before necrotic tissues were reabsorbed into the body.

Treatment was performed on the subjects by performing a laparotomy and inserting electrodes through the prostate capsule. Treatment was performed at 40 mA and with a dose of between 4 and 70 C. The subjects' blood, urine, general health, and behavior patterns were monitored before sacrificing them at time intervals of 1, 3, 20, 40, and 60 days after treatment. The prostate and surrounding tissues were dissected and examined after sacrifice. Ultrasound and CT scans were used throughout the study to identify the necrotic lesions and identify any changes that took place to the lesion.

Figure 69A:
FIG. 69a illustrates a slice of prostate 20 days after treatment.
Figure 69B:
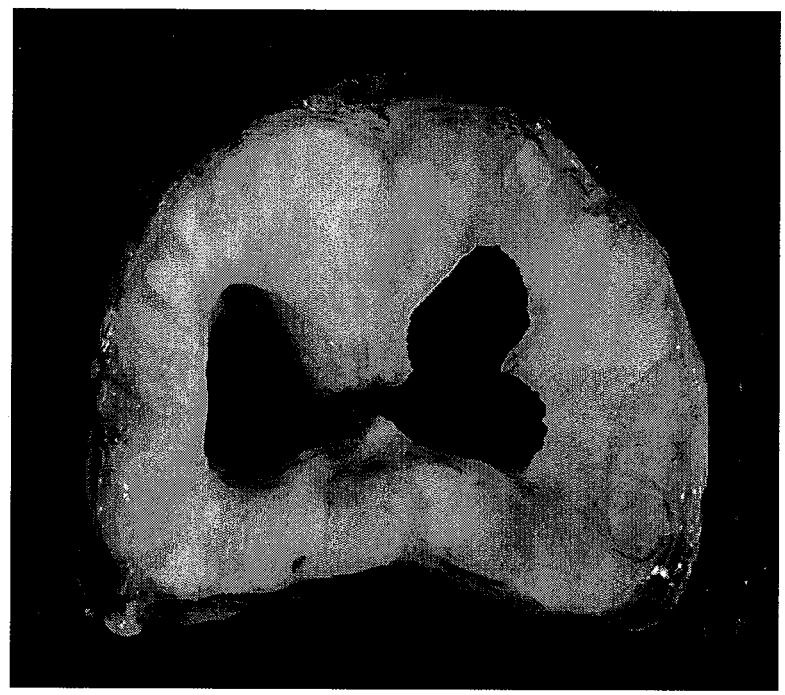
FIG. 69b illustrates a slide of prostate 40 days after treatment.

Ultrasound, CT imaging, and visual verification during histology showed that voids or cavities were created in the prostate tissue in the necrotic areas induced by DC ablation. FIGS. 69a and 69b illustrate slices of prostate at 2 times of sacrifice through the center of treatment zones. FIG. 69a illustrates a slice of prostate 20 days after treatment. FIG. 69b illustrates a slice of prostate 40 days after treatment. The necrotic tissue was substantially absorbed into the body by the first screening date, 20 days after treatment. Re-absorption resulted in voids, shown in FIGS. 31a and 31b.

The voiding within the prostates caused the overall shape and size of the prostate to shrink. In one subject the prostate had a measured width of 40 mm prior to treatment. Twenty days after treatment, the prostate had a measured width of 28 mm.

The results of Example 1 show substantially complete absorption of the necrotic tissue with little or no fibrotic scarring. The tissue around the voids created by DC ablation remains soft and pliable without forming surrounding hardened scar tissue.

Sacrifice of the subjects and examination of the prostate showed that the necrotic tissue was contained within the capsule and all tissues in the pelvic cavity remained healthy. Within the prostate itself, tissue immediately adjacent to the necrotic zones remained healthy, illustrating a sharp diffusion gradient. The size of the voids created coincided with dose response algorithms previously developed. The studies thus confirmed that the treatment has a sharp diffusion gradient and a predictable dose response All subjects remained healthy throughout the study and maintained normal urination and defecation patterns without signs of straining or discomfort.

Histology Results: Following treatment, all animals were terminated and subjected to necropsy examinations. Representative prostate samples fixed in 10% neutral buffered formalin were trimmed in the coronal plane perpendicular to the urethra, and 1.5 to 2.5 mm sequential slices were photographed.

Bilateral coagulation to liquefaction necrosis was observed in both acute animals (Animals 7C161 and 7C163). There was minimal associated inflammation and mild hemorrhage. Bilateral multifocal to coalescing inflammation was observed in the subcapsular parenchyma in all six chronic animals (Animals 7C201, 7C206, 7C197, 7C199, 7C202 and 7C204). There were cellular infiltrates (primarily lymphocytes and macrophages) expanding the interacinar mesenchyme. Moderate reaction was observed in Animal 7C202 while the response was minimal to mild in the multiple sections from the remaining animals from the three chronic observation periods.

Acinar atrophy characterized by reduction of lobular and sublobular clusters of glands with reduction of lumen and lining with attenuated cells was a consistent finding in all chronic animals. The intensity ranged from minimal to moderate. Moderate acinar atrophy was observed in multiple sections of all chronic animals except Animal 7C204 from the 60 day group, in which the reaction was minimal in four of the five sections studied.

Bilateral loss of parenchyma leading to formation of cavities was present in multiple sections from all six chronic prostate samples. These cavities were variable in size and often coalesced with the adjacent urethra. In most sections, a unilateral cavity merged with the urethra. In a few sections the urethra merged with bilateral cavities on either side of the prostate. The cavities often were lined by urothelium, possibly a regenerative and reparative response from the communicating urethral epithelium. Presence of cavities that represented loss of tissue mass from the electrical devices in all the specimens from three treatment groups suggest the lasting effect of reducing prostate mass by the devices over a period of 60 days. Also, there was no significant inflammatory reaction in the tissue surrounding the cavities, suggesting such union of necrotic tissue cavity and urethra either did not incite inflammatory response or the inflammation had receded and resolved completely at the time points of observation. Additionally, the urethra had one or many of the changes that included epithelial discontinuity in the form of erosion and ulceration, focal subepithelial inflammation and minimal hemorrhage, intracytoplasmic vacuolation of urothelium over a segment of urethra, focal aggregate of luminal necrotic cellular debris, patchy granulation tissue in the adjacent stroma and a marginal increase in periurethral mesenchyme.

Cystic dilation of glandular acini of variable degrees, ranging from isolated focal area to a substantial proportion of the remaining prostate gland, was observed in all the animals. These changes were present in multiple sections in the same animal. The changes were minimal in Animal 7C202. The dilated acini were lined by cuboidal to attenuated cells and occasionally contained sloughed cells, cellular debris and secretory product. Within the atrophic acini, multifocal expanding islands of regenerating glands were observed in a few animals. The foci of regeneration impinged the adjoining atrophic gland and were comprised of arborizing acini lined by tall columnar cells with abundant eosinophilic cytoplasm, vesicular nuclei with rare mitotic figures.

The study showed a reduction in the prostatic tissue mass using DC ablation as evidenced by loss of tissue surrounding the electrode insertion sites and atrophic changes incited elsewhere within the gland. The effects were persistent and observed in multiple sections of prostates at 20, 40 and 60 days following the treatment procedure. The merging of device-induced cavities and the urethra is likely a portal of drainage for the necrotic tissue mass contributing to the minimization of the inflammatory reaction in the remaining tissue.

Example 2

A study was performed to determine comparative size of the treatment region of a volume of tissue treated with a cathode and a volume of tissue treated with an anode. Beef round samples and in-vitro canine prostates were treated.

The following protocol was used to examine the amount of treated volume in beef round samples and in prostate at both the anode and the cathode:

1a. Treat beef samples with the following currents: 20, 40, and 60 mA.

1b. Treatment of in-vitro prostates with 40 mA of current.

2a. Treat beef samples with the following doses: 36, 72, 108, and 144 C.

2b. Treat in-vitro prostates with 4 and 13 C of dose.

3. Soak samples in formalin solution for a minimum of approximately 48 hours.

4. Slice samples with meat cutter into approximately 3 mm slices.

5. Measure thickness of each sample at anode and cathode treatment.

6. Photograph each slice.

7. Measure area of treatment in each sample using Microsoft Visio software.

8. Calculate volume treated (post-fixation) for anode and cathode.

9. Compare data.

Beef round samples were tested with 12 mm simple Pt/Ir pin electrodes. Prostate samples were tested with various pin and coil sizes. Results are shown in Tables 7 and 8, below.

TABLE 7

Beef Round Results

| Dose (C) | Current (mA) | Cathode Volume (cc) | Cathode Std Dev (cc) | N (Samples Tested) | Anode Volume (cc) | Anode Std Dev (cc) | N (Samples Tested) |
|---|---|---|---|---|---|---|---|
| 4 | 20 to 60 | 0.22 | 0.04 | 3 | 0.15 | 0.00 | 3 |
| 36 | 20 to 60 | 1.18 | 0.26 | 9 | 1.24 | 0.18 | 9 |
| 72 | 20 to 60 | 2.45 | 0.47 | 9 | 2.33 | 0.23 | 9 |
| 108 | 20 to 60 | 3.09 | 0.64 | 22 | 3.23 | 0.93 | 22 |
| 144 | 20 to 60 | 3.95 | 0.29 | 9 | 4.23 | 0.66 | 9 |

TABLE 8

| Dose (C) | Current (mA) | Cathode Volume (cc) | Cathode Std Dev (cc) | N (Samples Tested) | Anode Volume (cc) | Anode Std Dev (cc) | N (Samples Tested) |
|---|---|---|---|---|---|---|---|
| 4 | 40 | 0.29 | 0.24 | 3 | 0.24 | 0.06 | 3 |
| 13 | 40 | 0.76 | 0.17 | 3 | 0.86 | 0.19 | 3 |

Figure 70:
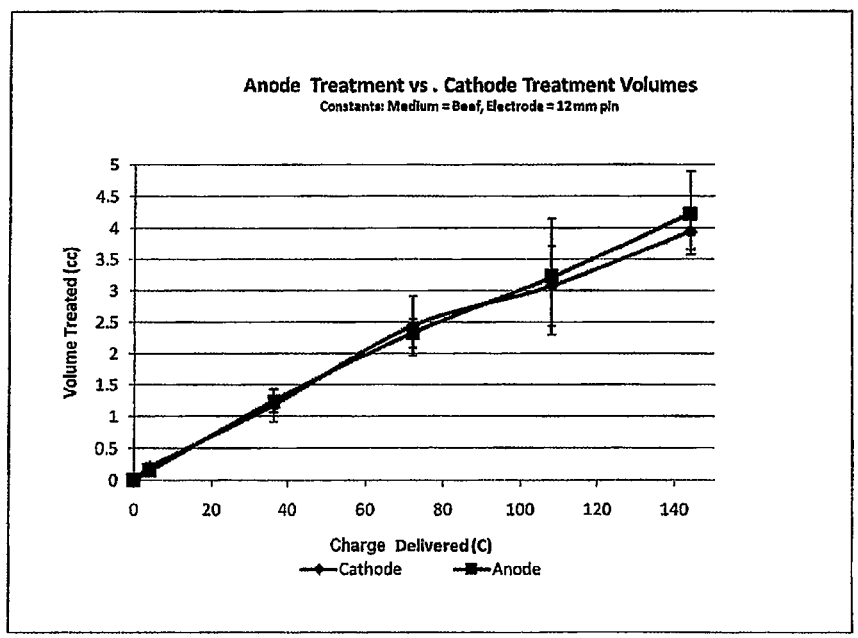
FIG. 70 illustrates treatment volume against charge delivered for anode treatment and cathode treatment for beef rounds.

FIG. 70 illustrates treatment volume against dose delivered for both anode treatment and cathode treatment for beef rounds. As shown in FIGS. 70 there is no significant difference in treatment volumes between the anode and the cathode.

Example 3

A study was performed to determine the effects of delivering a dose at different currents on the amount of treated volume. Beef round samples were treated. Protocol used for Example 3 followed the protocol of Example 2 for beef round samples.

The results of the study indicated that in the range of current between 20 and 60 mA, there is substantially no appreciable difference in the results of treatment.

Results are shown in Tables 9 and 10, below.

TABLE 9

Cathode Results

| Dose (C) | Current (mA) | Cathode Volume (cc) | Cathode Std Dev (cc) | N (Samples Tested) |
|---|---|---|---|---|
| 4 | 40 | 0.22 | 0.04 | 3 |
| 36 | 20 | 1.04 | 0.22 | 2 |
| 36 | 40 | 1.08 | 0.15 | 4 |
| 36 | 60 | 1.40 | 0.33 | 3 |
| 72 | 20 | 2.33 | 0.13 | 2 |
| 72 | 40 | 2.36 | 0.42 | 4 |
| 72 | 60 | 2.65 | 0.73 | 3 |
| 108 | 20 | 2.50 | 0.37 | 3 |
| 108 | 40 | 3.27 | 0.62 | 15 |
| 108 | 60 | 2.85 | 0.62 | 4 |
| 144 | 20 | 3.98 | 0.24 | 2 |
| 144 | 40 | 3.86 | 0.33 | 4 |
| 144 | 60 | 4.05 | 0.33 | 3 |

TABLE 10

Anode results

| Dose (C) | Current (mA) | Anode Volume (cc) | Anode Std Dev (cc) | N (Samples Tested) |
|---|---|---|---|---|
| 0 | | 0 | 0 | 0 |
| 4 | 40 | 0.15 | 0.00 | 3 |
| 36 | 20 | 1.23 | 0.01 | 2 |
| 36 | 40 | 1.32 | 0.21 | 4 |
| 36 | 60 | 1.15 | 0.18 | 3 |
| 72 | 20 | 2.08 | 0.00 | 2 |
| 72 | 40 | 2.53 | 0.17 | 4 |
| 72 | 60 | 2.23 | 0.11 | 3 |
| 108 | 20 | 3.03 | 0.95 | 3 |
| 108 | 40 | 3.31 | 0.92 | 15 |
| 108 | 60 | 3.04 | 1.15 | 4 |
| 144 | 20 | 4.10 | 0.13 | 2 |
| 144 | 40 | 4.49 | 0.42 | 4 |
| 144 | 60 | 3.97 | 1.09 | 3 |

Figure 71:
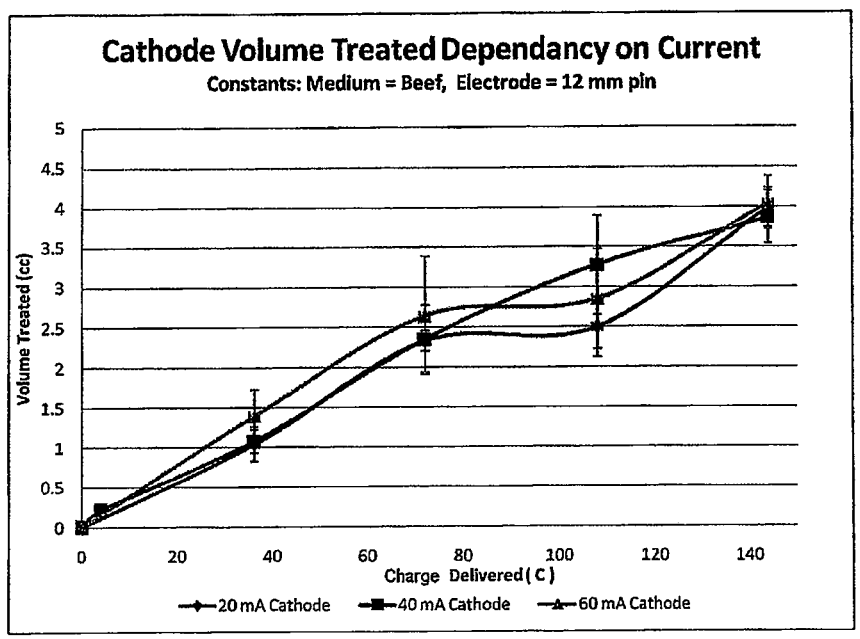
FIG. 71 illustrates anode results for treatment volume against charge delivered for a 20 mA cathode, a 40 mA cathode, and a 60 mA cathode.

FIG. 71 illustrate tables of the data. FIG. 71 illustrates cathode results for treatment volume against dose delivered for a 20 mA cathode, a 40 mA cathode, and a 60 mA cathode.

As shown in FIGS. 71 the dose to volume relationship is not influenced by the amount of current delivered to the electrodes up to 144C and with a current between 20 and 60 mA. The relationship between dose and volume treated is linear. The variation between dose and volume increases with dose, presumable due to the sensitivity of the radius of treatment zone on the volume.

Example 4

A study was performed to determine the margin of safety that the capsule provides from causing damage external to the prostate. Canine subjects were treated.

Two canines were treated with doses that were expected to interact with the capsule. The following parameters were looked at to determine whether the dose delivered caused harm to the patient by causing necrosis to tissues outside of the capsule:

1. Comparison of the ratio between actual treatment and the expected efficacious treatment.
2. Visual observation of blackened tissue outside of the capsule due to treatment.

3. Visual observation of blackened tissue visible on the capsule.
4. Histological evidence of capsule remaining.

The two canines had transverse widths of approximately 33 mm and 20 mm respectively and were treated with 16 mm coil electrodes. Using these transverse widths and assumptions listed below, a Targeted Prescribed Dose was determined for each prostate.

Assumptions:
  a. Treatment diffuses equally from electrode.
  b. Tissue dose response is in the range of 18 to 30 C/cc for canine prostatic tissue.
  c. Targeted Prescribed Dose incorporates a 10% radius safety margin to the capsule while preserving a 6 mm diameter in the center of the prostate for the urethra.
  d. Targeted Prescribed Dose is the midpoint between the dose resulting in a treatment radius following the above assumptions.

Targeted and Actual Doses delivered to the two subjects are shown in Table 11, below.

Resulting Target and Actual Doses Delivered to the Two Subjects in this Study

TABLE 11

| Subject | Targeted Prescribed Dose | Actual Delivered Dose | Over Dose |
|---|---|---|---|
| Subject 1 | 64 C# | 70 C | 1.1:1 |
|  | 42 C## |  | 1.6:1 |
| Subject 2 | 16 C# | 24 C | 1.5:1* |
|  | 16 C# |  | 1.5:1* |

*Indicates a dose was delivered that was 50% over recommended aggressive dosing.
Indicates dosing if placement of electrode is absolute with a 10% safety margin from interaction with capsule tissues
Indicates dosing if placement error of electrode is known and no safety margin accounted for in dosing The treatment zone was visually verified to be contained within the capsule in Subject 1. In subject 2 the treatment zone penetrated through the capsule and affected tissues outside of the prostate.

Tissues adjacent to the prostate were affected at the right caudal end. This lobe was treated by the anode. Based on the position and length of the anode electrode, and taper of this prostate anatomy, it was determined that the electrode was no further than approximately 2 mm from the capsule. If it is assumed that the electrode is 2.5 mm from the capsule, the predicted target dose may be about 9C. This calculates to a 2.6 to 1 Over Dose ratio in the right caudal portion of this prostate with 16 mm electrodes.

After treatment in both subjects, a blackened treatment zone was visible on the left lateral side of the prostate in Subject 1. Tissue adjacent to this zone appeared healthy. This illustrates that the treatment zone did diffuse far enough that it interacted with the capsule. The fact that no necrotic tissues were observed in adjacent tissue indicates that the hydrogen and hydroxyl ions were contained within the capsule.

The capsule of Subject 2 saw extensive treated tissue up to the capsule boundary at the cathode, presumably due to both the overtreatment of the capsule and the electrodes being placed closer to the outer capsule than the urethra. This biased the treatment towards the capsule more than would be expected with a 10% overdose. The overdose ratio was recalculated using the actual distance from the capsule and it was found that the cathode in Subject 2 was overdosed by 60%.

Examining the histology in areas where the treatment visually was adjacent to the capsule was not definitively conclusive due to the fact that the slide preparation process can be destructive to these boundary tissues. Histological evidence and the pathologist's conclusions indicated that the cellular structures making up the capsule showed necrosis but the capsule's structural integrity was maintained. This assessment agrees with the visual observations seen during the procedure and necropsy with the exception of the right caudal portion of the prostate of Subject 2.

In this acute animal study, prostates were nominally overdosed by 50 to 60%. No treatment was observed outside of the prostate capsule except in the localized area where the electrode was very close to the capsule. The estimated overdosing in this localized area was 160%. This indicates that, in a small sample size, the canine prostate capsule allows overdosing somewhere between 50% and 160% without allowing the treatment to affect adjacent tissues outside of the capsule. Anecdotal evidence indicates that the human capsule is more substantial than the canine capsule.

Example 5

A study was performed to assess various impedance parameters including dose to failure, effect of length, effect of electrode type, effect of electrode diameter, effect of pin diameter, effect of insulation, effect of current and parallel paths, The Dose to Failure evaluation showed that dose to failure is inversely proportional to length and diameter of the electrode and is proportional to the amount of venting. The following equation was determined:

$$DTF = (Gas\ Formation - Venting) * current$$

$$DTF = (1/(d*L) - (n^2 * \Delta p/l)) * I$$

where:
  DTF=Dose Time to Failure
  d=diameter of electrode
  L=length of electrode
  n=number of electrodes
  $\Delta p$=pressure drop across vent
  l=length of insulation
  I=current at electrode Through empirical testing it was shown that as pin length and diameter increases the impedance stability of the system increases. Furthermore as the electrode surface area of the active section increases the impedance stability increases. With a constant electrode surface area of the active sections impedance stability increases with a lower magnitude of direct current or running multiple electrodes in parallel. With a constant current and electrode surface area of the active section the impedance stability increases by decreasing the insulation length from the active area back to catheter by allowing the gases to vent out of the active area.

Example 6

A study was performed to assess the corrosive properties of Nitinol and platinum-iridium-coated Nitinol wires. The study further observed the effects of Parylene-coated electrodes on electrode corrosion and tissue treatment zones.

Nitinol is commonly used in medicine and is known to corrode at the anode with applied direct current. Platinum is resistant to corrosion. Accordingly, for testing the invention disclosed herein, platinum iridium coated Nitinol wires have been employed.

Parylene-C coating has high electro-resistivity, is corrosion resistant, has high electrical impedance, and is impermeable to moisture. In this study, Parylene-C coating was applied to both Nitinol and platinum iridium electrodes.

Two tests were performed. One test used Nitinol wires for both cathode and anode. The other test used platinum iridium-coated Nitinol wires for both cathode and anode. The electrodes were inserted into two separate gels and run for 120 coulombs at 25 mA. To confirm no corrosion of the platinum iridium-coated Nitinol electrodes, a further test was performed that was run for 500 coulombs at 25 mA. Pictures of each electrode were taken before and after the tests in order to see changes in the appearance of the electrodes. Observations and results were documented.

Figure 72A:
FIG. 72a illustrates a Nitinol anode before starting a test.
Figure 72B:

FIGS. 72a and 72b illustrate the Nitinol anode before starting the test and after the test was stopped, respectively. The tests were to carry on for 120 coulombs at 25 mA. After approximately 20 minutes, the current for the Nitinol electrodes dropped to 0 (zero). This was presumably due to corrosion of the anode, as illustrated in FIG. 73c.

The Nitinol cathode had no apparent corrosion, nor did the platinum iridium-coated electrodes. The confirmation test of 500 coulombs at 25 mA also resulted in no observable corrosion of either the anode of the cathode.

The Parylene-C coating also was found to be a dependable insulator. The portions of the electrodes that were coated with Parylene C were not active. No ion exchange occurred in these regions. This was observed at the start of the tests when the treatment sizes were not so big that they overlapped the coated regions. This coating also appeared to have a positive effect on impedance. It appeared that the microscopic insulation facilitated gas escape, resulting in a lower impedance.

The results showed that the Nitinol anode had significant corrosion but the cathode did not. The platinum/iridium-coated Nitinol wires had no corrosion, even after further testing with 500 coulombs.

Example 7

A study was performed to determine the relationship between ease of insertion and diameter in a prostate through the urethra from the capsule. Pig prostates were used.

Two pig prostates and urethras were inserted with various diameter pin electrodes. The resulting ease of insertion to pierce through the capsule and into the urethra was subjectively judged by the individuals inserting the pins into the urethras. Pins were approximately 8 mm in length. Other methods of introducing the pin into the tissue were tried and judged relative to the initial insertion method. These methods include using a 0.5 mm diameter needle to pierce through the capsule and into the swine urethra and using a pair of tweezers to pierce and pull the tissues apart. The ease of insertion was then subjectively ranked by two individuals, each of whom did the trials independently, with a rank of 10 being the easiest to insert and a rank of 1 indicating nearly impossible to insert.

Results are shown in Table 12, below.

TABLE 12

| Insertion Method | 0.5 mm Pt/Ir Pin | 0.8 mm Pt/Ir Pin | 0.3 mm Pt/Ir Coated NiTi |
|---|---|---|---|
| Normal | 6, 8 | 4, 6 | 1, 1 |
| Needle Pierced | 8, 7 | 6, 6 | 8, 1 |
| Tweezers | 8, 9 | 8, 9 | 2, 7 |

Test Subject: Subject 1 (First Number); Subject 2 (Second Number)

Both subjects ranked the diameter of electrodes in the following order: Best—0.5 mm Pt/Ir Pin, 0.8 mm Pt/Ir Pin, Worst—0.3 mm Pt/Ir coated pin.

The 0.5 mm diameter pin provided substantial stiffness such that the electrode did not buckle. The 0.8 mm pin did not insert as easily as the 0.5 mm pin, presumably because the created hole is larger. It is hypothesized that if the tip of the 0.8 mm pin was sharpened or tapered, it could perform as well as the 0.5 mm pin. The 0.3 mm pin provided very little stiffness or mechanical advantage and buckled. This pin was unable to be inserted.

Using a needle or tweezers to create a pilot hole was only incrementally better as it was difficult to find the hole.

Although the invention has been described with reference to specific embodiments, persons skilled in the art will recognize that changes may be made in form and detail without departing from the spirit and scope of the invention.

Example 8

Initial human feasibility studies using DC ablation in the prostate with the Neuflo System have been conducted in Santiago, Chile. A summary of the studies conducted is given in Table 13.

TABLE 13

Human Feasibility Studies Summary

| Study | Objectives | Subjects | Method | Findings |
|---|---|---|---|---|
| Stage 1: Ex Vivo post Radical Prostatectomy (RP) study of electrodes | 1. Validate tissue response in human prostate tissue. | 3 Prostates | Treat with DC ablation using pin electrodes inserted through the capsule immediately post RP | 1. Histological evidence of liquifactive and coagulative necrosis 2. Obtained a initial charge setting |
| Stage 2: In Vivo study of electrodes during RP | 1. Evaluate Treatment charge setting 2. Evaluate Impedance | 5 Subjects with Prostate Cancer | Treat with DC ablation using pin electrodes inserted through the capsule during RP | 1. Histological evidence of liquifactive and coagulative necrosis 2. Necrosis stayed within the capsule 3. Verified acceptable impedance |

TABLE 13-continued

Human Feasibility Studies Summary

| Study | Objectives | Subjects | Method | Findings |
|---|---|---|---|---|
| Stage 3: Transurethral Ex Vivo study of DC Ablation post RP | 1. Verify electrode placement and urethral puncture with Neuflo catheter 2. Determine optimal prostate size | 4 Prostates | Treat with TU Catheter immediately post RP | 1. Histological evidence of liquifactive and coagulative necrosis 2. Urethral puncture method was successful 3. Prostate size 30-65 cm$^3$ and sizing inc/exc criteria |
| Stage 4: Transurethral acute study of DC Ablation during RP | 1. Verify electrode placement and urethral puncture with Neuflo catheter 2. Determine optimal prostate size | 3 Prostate Cancer Subjects | Treat with TU Catheter during RP | 1. Histological evidence of liquifactive and coagulative necrosis 2. Urethral puncture method was successful 3. Prostate size 30-65 cm$^3$ and sizing inc/exc criteria |
| Feasibility Study of the TU DC Ablation System in BPH subjects | 1. Optimize treatment parameters 2. Obtain preliminary safety and efficacy data 3. Assess Discomfort | Up to 25 BPH subjects | Treat BPH with TU Catheter. Follow subjects for 1 year | 1. Obtained treatment parameters for US study 2. Obtained preliminary safety and efficacy data to utilized for hypothesis tests for the US study 3. Procedure was well tolerated |

Stage 1 of the DC Ablation human studies involved treating three (3) human prostates with pin electrodes immediately post-radical prostatectomy (RP) for prostate cancer. Results showed the ability of DC ablation to induce consistent necrotic lesions within both malignant and benign prostate tissue.

Stage 2 of the human studies (in vivo) was conducted by treating patients prior to radical prostatectomy with pin electrodes to examine tissue response in living human prostate tissue. Immediately following DC ablation treatment, the prostates were removed as RP commenced following treatment completion.

Figure 73:
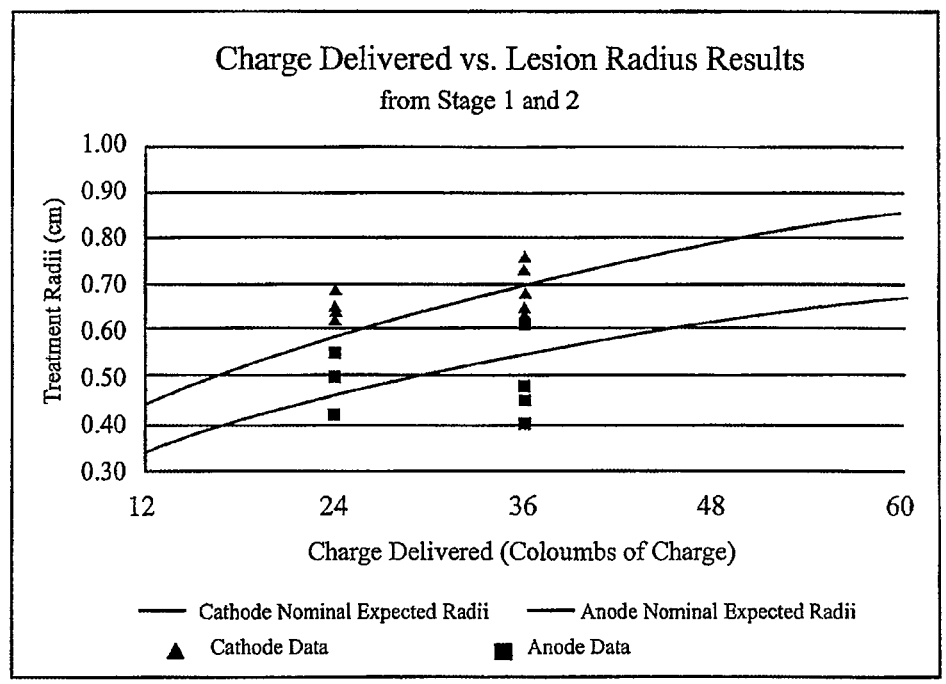

Results from the first two stages of human prostate tissue study are shown in FIG. 73.

Human prostates were treated ex vivo (Stage 3) and in vivo during radical prostatectomy (Stage 4) with a Transurethral DC Ablation Catheter to more accurately represent future treatments; and to optimize electrode placement and monitor the safety of the placement of needles near the bladder and urethra.

Figure 74:
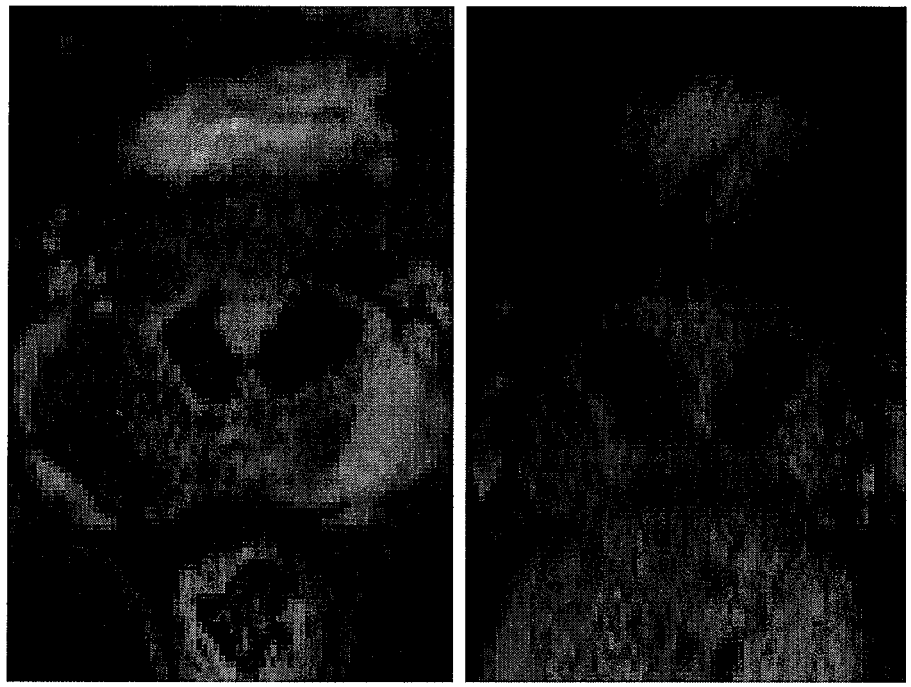

FIG. 74 is an in vivo image illustrating the necrosis volume achieved by the transurethrally ablating tissue with DC ablation.

Sixteen BPH patients were treated with a transurethral DC ablation system to investigate the safety and efficacy of using a TU DC ablation system as a treatment for BPH. Prostate sizes ranged from 30 to 90 cm$^3$. The procedure was administered in an office setting using a topical Lidocaine gel in the urethra. No oral sedative or local nerve block was required. Patients reported mild to no pain during the treatment.

Preliminary symptomatic relief data, as shown in Table 14, suggests that patients experienced symptomatic relief one week after treatment.

TABLE 14

BPH Feasibility Study Initial Efficacy Data
(Treatment Rate = 25 mA)

| Parameter | Baseline (n = 13) Mean ± SD | 1 week (n = 13) Mean ± SD (Paired % improvement) | 1 month (n = 10) Mean ± SD (Paired % improvement) | 3 month (n = 3) Mean ± SD (Paired % improvement) |
|---|---|---|---|---|
| AUA Symptom Score | 24.1 ± 4.8 | 14.3 ± 5.6 (38%) | 14.3 ± 5.6 (37%) | 7.7 ± 5.0 (65%) |
| QOL | 5.0 ± 0.8 | 2.8 ± 1.5 (44%) | 2.3 ± 1.7 (54%) | 0.7 ± 0.6 (86%) |
| Qmax | 9.6 ± 3.5 | 12.1 ± 2.5 (26%) | 13.7 ± 4.3 (43%) | 9.7 ± 5.0 (1%) |

In addition, 3 subjects were treated within the OUS study in which the treatment rate was 40 mA (Table 7). Based on the subject's transient (1 week) increase in symptoms, quality of life and their diminished ability to urinate, a decision was made to utilize a treatment rate of 25 mA. Initial safety data revealed no severe adverse events in the first 16 patients. Urological adverse events are listed in the Table 15.

TABLE 15

Urological Adverse Event Frequency
(Treatment Rate = 25 mA and 40 mA)

| | Timepoints* | | |
|---|---|---|---|
| Adverse Event | 1 week (n = 12) (mild/mod/severe) | 1 month (n = 12) (mild/mod/severe) | 3 month (n = 6) (mild/mod/severe) |
| Hematuria | 17%/0%/0% | 0%/0%/0% | 0%/0%/0% |
| Dysuria | 55%/23%/8% | 40%/20%/8% | 17%/0%/0% |
| Pelvic Pain | 31%/0%/0% | 20%/0%/0% | 0%/0%/0% |
| Bladder Spasms | 23%/23%/0% | 0%/0%/0% | 0%/0%/0% |
| Urgency Incontinence | 8%/15%/0% | 8%/0%/8% | 17%/0%/0% |
| Incontinence | 0%/0%/0% | 0%/0%/0% | 0%/0%/0% |
| Urinary Infection | 0%/0%/0% | 0%/0%/0% | 0%/0%/0% |
| Acute Retention | 0% | 0% | 0% |

*includes monitored data only

What is claimed is:

1. A catheter for use in a system for treating tissue in a body using direct current ablation comprising:
    a tubular body having a proximal end and a distal end and being semi-flexible, bi-directionally torqueable, and chemically resistant, the tubular body including:
        a tip positioned at the distal end;
        a plurality of electrodes routed therethrough;
        a composite non-threaded inner sheath generally at an interior portion thereof;
        a chemically resistant non-threaded outer sheath generally at an exterior portion thereof, the outer sheath comprising a plurality of routing holes provided between the proximal end and the distal end, wherein each of the plurality of routing holes is formed proximate the tip and defines a radiused channel of a shape and an orientation configured to direct a corresponding one of the plurality of electrodes from the tubular body into the tissue at a pre-determined angle;
        a fixation element operably coupled thereof, wherein the fixation element is configured to fix the catheter in place in the body during treatment of the tissue; and
        an electrode driver mechanically coupled to the inner sheath, wherein each of the plurality of electrodes is fixed to the electrode driver, and wherein the electrode driver includes an open aperture configured for a fluid to flow therethrough from the proximal end toward the distal end thereof,
    wherein the catheter is configured for linear electrode deployment such that the plurality of electrodes are configured to be deployed through the plurality of routing holes and into the tissue via relative longitudinal movement between the inner sheath and the outer sheath;
    wherein the tubular body has a flex modulus of between about 0.5 and 3 Gpa and is configured to withstand an axial force of approximately 40-80 Newtons with a strain of less than approximately 1% over 300 mm length.

2. The catheter of claim 1, wherein the tubular body is configured to withstand a torque of approximately 1 inch-pound.

3. The catheter of claim 1, wherein the inner sheath comprises a PEEK tube and the outer sheath comprises a braided outer tube.

4. The catheter of claim 1, wherein the inner sheath is formed of at least two layers, and the at least two layers comprise an inner layer, a reinforcing layer, and an outer layer.

5. The catheter of claim 4, wherein the inner layer is FTFE, the reinforcing layer is a stainless steel wire braid, and the outer layer comprises a PEBAX coating.

6. The catheter of claim 5, wherein a section of the stainless steel wire braid includes a non-braided section and wherein the routing holes are provided in the non-braided section.

7. The catheter of claim 4, wherein the inner layer is PEBAX, the reinforcing layer is a stainless steel wire braid, and the outer layer comprises a PEBAX coating.

8. The catheter of claim 1, wherein the outer sheath is chemically resistant to strong acids and strong bases.

9. The catheter of claim 1, wherein the routing holes are provided along a distal portion of the tubular body proximate the distal end.

10. The catheter of claim 1, wherein the routing holes further operate as vacuum ports.

11. The catheter of claim 10, further comprising a vacuum connector proximate the proximal end of the tubular body.

12. The catheter of claim 1, comprising 3 bands of routing holes in 4 rows.

13. The catheter of claim 12, wherein the bands are spaced 2 cm apart.

14. The catheter of claim 1, wherein the tip has a Coude shape.

15. The catheter of claim 1, wherein the tip comprises silicone rubber.

16. The catheter of claim 1, wherein the tip is flexible and wherein the pre-determined angle is at approximately 30 degrees.

17. The catheter of claim 1, further comprising a radiopaque marking along the tubular body.

18. The catheter of claim 1, further comprising an outer tube for placement over the outer sheath after the plurality of electrodes have been deployed for removal of the catheter.

19. The catheter of claim 1, wherein the tubular body is preformed to match a shape of the area of the body to be treated.

20. The catheter of claim 19, wherein the tubular body is preformed to match a verumontanum area.

21. The catheter of claim 20, wherein the tubular body comprises alternating rigid sections and flexible sections.

22. The catheter of claim 1, wherein the fixation element is an inflatable balloon configured for inflation by the fluid that flows through the open aperture of the electrode driver.

23. The catheter of claim 1, further comprising a vibrating mechanism associated with the tubular body for vibrating the tubular body.

24. The catheter of claim 23, wherein the vibrating mechanism is provided proximate the proximal end of the tubular body.

25. A catheter for use in a system having a plurality of electrodes for treating tissue in a body using direct current ablation comprising:

a tubular body having a proximal end and a distal end and being semi-flexible, bi-directionally torqueable with a flex modulus of between about 0.5 and about 3 GPa and chemically resistant, the tubular body including:

a tip positioned at the distal end;

a composite non-threaded inner sheath generally at an interior portion thereof;

a non-threaded outer sheath generally at an exterior portion thereof and being chemically resistant to high pH and low pH, the outer sheath defining a plurality of routing holes provided between the proximal end and the distal end, each of the plurality of routing holes defining a radiused channel of a shape and an orientation configured to direct a corresponding one of the plurality of electrodes from the tubular body into the tissue at a pre-determined angle;

a first fixation element operably coupled thereto, wherein the fixation element is configured to fix the catheter in place in the body during treatment of the tissue; and an electrode driver mechanically coupled to the inner sheath and fixed to the electrodes, wherein the catheter is configured for linear electrode deployment such that the plurality of electrodes are configured to be deployed through the plurality of routing holes and into the tissue by the electrode driver via relative longitudinal movement between the inner sheath and the outer sheath, and wherein the electrode driver includes an open aperture configured for a fluid to flow therethrough from the proximal end toward the distal end thereof.

26. The catheter of claim 25, wherein the first fixation element is provided at the distal end of the tubular body.

27. The catheter of claim 26, wherein the first fixation element comprises a balloon having a shape similar to a shape of the tip.

28. The catheter of claim 25, wherein the first fixation element is provided at a location proximal of the distal end of the tubular body.

29. The catheter of claim 28, wherein the first fixation element has a length of approximately 5 cm.

30. The catheter of claim 25, wherein the first fixation element is an elastomeric balloon.

31. The catheter of claim 30, wherein the balloon comprises silicone rubber.

32. The catheter of claim 30, wherein the first fixation element is configured for inflation by air.

33. The catheter of claim 30, wherein the first fixation element is configured for inflation by saline.

34. The catheter of claim 25, wherein the first fixation element comprises a balloon and is configured and positioned to substantially block the flow of chemicals created by electrolysis to other structures of the body.

35. The catheter of claim 34, further comprising a second fixation element comprising a balloon configured and positioned such that the first fixation element and second fixation element may together form a contained area.

36. The catheter of claim 25, further comprising a second fixation element comprising electrodes.

37. The catheter of claim 25, wherein the first fixation element is provided on the tubular body between the proximal end and the distal end and wherein the first fixation element is configured to permit fluid flow thereacross.

38. The catheter of claim 37, wherein the first fixation element comprises a polymeric element including channels for fluid flow.

* * * * *